US012049634B2

(12) United States Patent
Khan et al.

(10) Patent No.: US 12,049,634 B2
(45) Date of Patent: Jul. 30, 2024

(54) METHODS OF SUGARCANE TRANSFORMATION USING MORPHOGENES

(71) Applicants: CENTRO DE TECNOLOGIA CANAVIEIRA S.A., São Paulo (BR); CTC GENOMICS, LLC, St. Louis, MO (US)

(72) Inventors: Tanveer Khan, São Paulo (BR); Valter Miotto Alessio, São Paulo (BR); Joao Paulo de Oliveira Correa, São Paulo (BR); Carlos Manuel Hernandez Garcia, St. Louis, MO (US); Viktoriya Coneva, St. Louis, MO (US); Chuanmei Zhu, St. Louis, MO (US)

(73) Assignees: CENTRO DE TECNOLOGIA CANAVIEIRA S.A., São Paulo (BR); CTC GENOMICS, LLC, St. Louis, MO (US)

( * ) Notice: Subject to any disclaimer, the term of this patent is extended or adjusted under 35 U.S.C. 154(b) by 0 days.

(21) Appl. No.: 17/504,264

(22) Filed: Oct. 18, 2021

(65) Prior Publication Data
US 2022/0135990 A1    May 5, 2022

Related U.S. Application Data

(60) Provisional application No. 63/092,950, filed on Oct. 16, 2020.

(51) Int. Cl.
*C12N 15/82* (2006.01)
(52) U.S. Cl.
CPC ............... *C12N 15/8205* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| EP | 116718 A1 | 8/1984 |
| EP | 242246 A1 | 10/1987 |
| EP | 270822 A1 | 6/1988 |

(Continued)

OTHER PUBLICATIONS

Lowe et al. "Rapid genotype BindependentΛ Zea mays L. (maize) transformation via direct somatic embryogenesis" 2018 In Vitro Cells & Developmental Biology—Plant 54:240-252 (Year: 2018).*

(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

Aspects of the present disclosure relate to methods and compositions for sugarcane transformation using morphogenic genes. In particular, the present disclosure relates to the use of morphogenic sequences that improve the efficiency of sugarcane cell or tissue transformation and genomic modification. The present disclosure further relates to genetically altered sugarcane cells, tissues, and plants produced using these methods and compositions.

4 Claims, 9 Drawing Sheets
Specification includes a Sequence Listing.

No morphogene (- control)    ZmWUS (+ control)    PhRKD4

(56) References Cited

U.S. PATENT DOCUMENTS

| | | | |
|---|---|---|---|
| 4,800,159 | A | 1/1989 | Mullis et al. |
| 2017/0121722 | A1 | 5/2017 | Anand et al. |

FOREIGN PATENT DOCUMENTS

| | | |
|---|---|---|
| WO | WO-1984002913 A1 | 8/1984 |
| WO | WO-1996006932 A1 | 3/1996 |
| WO | WO-1997048819 A1 | 12/1997 |

OTHER PUBLICATIONS

Hoerster et al. "Use of non-integrating Zm-Wus2 vectors to enhance maize transformation" Jan. 2, 2020 In Vitro Cellular & Developmental Biology—Plant 56:265-279 (Year: 2020).*

UniProtKB Accession A0A2T8ILJ3 entitled "RWP-RK domain-containing protein", versioon 9 dated Jul. 31, 2019 (1 total page). (Year: 2019).*

DAFNY-YELIN and TZFIRA "Delivery of Multiple Transgenes to Plant Cells" 2007 Plant Physiology 145:1118-1128. Specification at ¶59 at pp. 47-47. (Year: 2007).*

Altschul et al., (1990). "Basic local alignment search tool," J. Mol. Biol., 215:403-410.

Altschul et al., (1997). "Gapped BLAST and PSI-BLAST: a new generation of protein database search programs," Nucl. Acids. Res., 25:3389-3402.

An et al., (1996). "Strong, constitutive expression of the *Arabidopsis* ACT2/ACT8 actin subclass in vegetative tissues," The Plant J, 10(1): 107-121.

Boutilier et al., (2002). "Ectopic Expression of BABY BOOM Triggers a Conversion from Vegetative to Embryonic Growth," Plant Cell, 14(8):1737-1749.

Brand et al., (2019). "*Arabidopsis* LEC1 and LEC2 Orthologous Genes Are Key Regulators of Somatic Embryogenesis in Cassava," Front Plant Sci, 10:673, 14 pages.

Chardin et al., (2014). "The plant RWP-RK transcription factors: key regulators of nitrogen responses and of gametophyte development," Journal of Experimental Botany, 65(19):5577-5587.

Cona et al., (2003). "Polyamine Oxidase, a Hydrogen Peroxide-Producing Enzyme, Is Up-Regulated by Light and Down-Regulated by Auxin in the Outer Tissues of the Maize Mesocotyl," Plant Physiology, 133:803-816.

Coussens et al., (2012). "Brachypodium distachyon promoters as efficient building blocks for transgenic research in maize," Journal of experimental botany, 63(11): 4263-4273.

De Pater et al., (1992). "The promoter of the rice gene GOS2 is active in various different monocot tissues and binds rice nuclear factor ASF-1," The Plant J, 2(6):837-844.

Franck et al., (1980). "Nucleotide sequence of cauliflower mosaic virus DNA," Cell, 21(1):285-294.

Gardner et al., (1981). "The complete nucleotide sequence of an infectious clone of cauliflower mosaic virus by M13mp7 shotgun sequencing," Nucleic Acids Res, 9(12):2871-2888.

Gielen et al., (1984). "The complete nucleotide sequence of the TL-DNA of the Agrobacterium tumefaciens plasmid pTiAch5," EMBO J, 3:835-845.

Hecht et al., (2001). "The *Arabidopsis* Somatic Embryogenesis Receptor Kinase 1 Gene Is Expressed in Developing Ovules and Embryos and Enhances Embryogenic Competence in Culture," Plant Physiol., 127:803-816.

Horstman et al., (2017). "The BABY BOOM Transcription Factor Activates the LEC1-ABI3-FUS3-LEC2 Network to Induce Somatic Embryogenesis," Plant Physiology, 175(2):848-857.

Iwase et al., (2011). "WIND1 A key molecular switch for plant cell dedifferentiation," Plant Signaling and Behavior, 6(12):1943-1945.

Iwase et al., (2017). "WIND1 Promotes Shoot Regeneration through Transcriptional Activation of Enhancer of Shoot Regeneration1 in *Arabidopsis*," Plant Cell, 29:54-69.

Karlin et al., (1990). "Methods for assessing the statistical significance of molecular sequence features by using general scoring schemes" PNAS USA, 87:2264-2268.

Karlin et al., (1993). "Applications and statistics for multiple high-scoring segments in molecular sequences," PNAS USA, 90:5873-5877.

Last et al., (1990). "pEmu: an improved promoter for gene expression in cereal cells," Theor Appl Genet, 81:581-588.

Lowe et al., (2016). "Morphogenic Regulators Baby boom and Wuschel Improve Monocot Transformation," Plant Cell, 28(9):1998-2015.

Nozaki et al., (2010). "an3-Mediated Compensation Is Dependent on a Cell-Autonomous Mechanism in Leaf Epidermal Tissue," Plant and Cell Phys, 61(6):1181-1190.

Ouakfaoui et al., (2010). "Control of somatic embryogenesis and embryo development by AP2 transcription factors," Plant Molecular Biology, 74(4-5):313-326.

Saiki et al., (1985). "Enzymatic Amplification of ß-Globin Genomic Sequences and Restriction Site Analysis for Diagnosis of Sickle Cell Anemia," Science, 230:1350-1354.

Sinha et al., (1993). "Overexpression of the maize homeo box gene, KNOTTED-1, causes a switch from determinate to indeterminate cell fates," Genes Fev., 7:787-795.

Su et al., (2009). "Auxin-induced WUS expression is essential for embryonic stem cell renewal during somatic embryogenesis in *Arabidopsis*," Plant Journal, 59(3):448-460.

Szczygiel-Sommer et al., (2019). "The miR396-GRF Regulatory Module Controls the Embryogenic Response in *Arabidopsis* via an Auxin-Related Pathway," Int J Mol Sci, 20(20):5221, 18 pages.

Thakare et al., (2008). "The MADS-Domain Transcriptional Regulator AGAMOUS-LIKE15 Promotes Somatic Embryo Development in *Arabidopsis* and Soybean," Plant Physiology, 146:1663-1672.

Velten et al., (1984). "Isolation of a dual plant promoter fragment from the Ti plasmid of Agrobacterium tumefaciens," EMBO J, 3(12):2723-2730.

Velten et al., (1985). "Selection-expression plasmid vectors for use in genetic transformation of higher plants," Nucleic Acids Res, 13(19):6981-6998.

Verdaguer et al., (1998). "Functional organization of the cassava vein mosaic virus (CsVMV) promoter," Plant Mol Biol, 37:1055-1067.

Waki et al., (2011). "The *Arabidopsis* RWP-RK protein RKD4 triggers gene expression and pattern formation in early embryogenesis," Curr Biol., 21(15):1277-1281.

Zhang et al., (1991). "Analysis of rice Act1 5' region activity in transgenic rice plants," The Plant Cell, 3:1155-1165.

Zuo et al., (2002). "The WUSCHEL gene promotes vegetative-to-embryonic transition in *Arabidopsis*," Plant Journal, 30(3):349-359.

Christensen et al., (1992). "Maize polyubiquitin genes: structure, thermal perturbation of expression and transcript splicing, and promoter activity following transfer to protoplasts by electroporation," Plant Mol Biol, 18(4): 675-689.

Depicker et al., (1982). "Nopaline synthase: Transcript mapping and DNA sequence," J. Molec Appl Gen, 1:561-573.

Hull et al., (1978). "Structure of the cauliflower mosaic virus genome II. Variation in DNA structure and sequence between isolates," Virology, 86(2):482-493.

Liu et al., (2018). "Overexpression of the CsFUS3 gene encoding a B3 transcription factor promotes somatic embryogenesis in Citrus" Plant Sci, 277:121-131.

Schunmann et al., (2003). "A suite of novel promoters and terminators for plant biotechnology. II. The pPLEX series for use in monocots," Plant Funct Biol, 30:453-460.

Tsuwamoto et al., (2010). "*Arabidopsis* EMBRYOMAKER encoding an AP2 domain transcription factor plays a key role in developmental change from vegetative to embryonic phase," Plant Molecular Biology, 73(4-5):481-492.

* cited by examiner

METHODS OF SUGARCANE TRANSFORMATION USING MORPHOGENES

CROSS-REFERENCE TO RELATED APPLICATION

This application claims the benefit of U.S. Provisional Application No. 63/092,950, filed Oct. 16, 2020, which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 207422000100SEQLIST.TXT, date recorded: Sep. 20, 2021, size: 99,705 bytes).

TECHNICAL FIELD

Aspects of the present disclosure relate to methods and compositions for sugarcane transformation using morphogenic genes. In particular, the present disclosure relates to the use of morphogenic sequences that improve the efficiency of sugarcane cell or tissue transformation and genomic modification. The present disclosure further relates to genetically altered sugarcane cells, tissues, and plants produced using these methods and compositions.

BACKGROUND

The complexity of the allopolyploid sugarcane genome has presented technical challenges in developing commercial cultivars using traditional breeding methods. Commercial sugarcane cultivars containing *Saccharum officinarum* and *S. spontaneum* genomes have over 100 chromosomes. Plant biotechnology and, more recently, genome editing, have presented opportunities to overcome these obstacles. However, even these more modern techniques present their own set of challenges.

Sugarcane is a vegetatively propagated crop that has a complex genome. Unlike in other row crops such as maize and soybean, the introduction (e.g., of transgenes) or alteration of genes (e.g., gene editing) cannot be done once in donor germplasm and then back-crossed into elite germplasm. Instead, elite sugarcane germplasm cells must be transformed or modified in order to develop new commercial cultivars, and transformation is required for both transgene and genome editing technology. Although the development of commercial sugarcane cultivars requires transformation, current transformation methods are not optimized for sugarcane. Further, as in other crop species, recalcitrance to tissue culture and transformation is observed in sugarcane, especially in elite varieties. In addition, recalcitrance to either genetic transformation and/or tissue culture and regeneration is highly genotype dependent.

There exists a clear need to develop an efficient method of sugarcane cell transformation and genomic modification and to decrease negative genotype-dependent effects on the process. There also exists a need to improve the efficiency of sugarcane genome modification. In order to satisfy the needs of a high-throughput commercial sugarcane biotechnology pipeline, new transformation and genomic modification methods and approaches are needed.

BRIEF SUMMARY

In order to meet these needs, the present disclosure provides methods and compositions for sugarcane transformation and genomic modification using morphogenic genes optimal for sugarcane. In particular, the present disclosure relates to the use of morphogenic sequences that improve the efficiency of sugarcane cell transformation and genomic modification. The present disclosure further relates to genetically altered sugarcane cells, tissues, and plants produced using these methods and compositions. The methods of the present disclosure reduces genotype dependence of transformation process, providing robust transformation and genomic modification protocols. Further, the methods of the present disclosure improve the number and quality of independent transgenic events per variety.

An aspect of the disclosure includes methods of producing a genetically altered sugarcane plant, including: (a) providing sugarcane cells or tissue; (b) introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 and at least one transgene nucleotide sequence to produce transgenic sugarcane cells; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. Some embodiments of this aspect further include screening the sugarcane cells between steps (b) and (c), screening the sugarcane cells during step (c), or screening the sugarcane cells after step (c), and optionally further selecting the transgenic sugarcane cells between steps (b) and (c), or selecting the transgenic sugarcane cells after step (c), optionally by using selectable markers. In some embodiments of this aspect, step (b) is achieved through *Agrobacterium* transformation, microprojectile bombardments, nanoparticle delivery, viral delivery, or a combination thereof. In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one morphogene nucleotide sequence is introduced with a first vector and the at least one transgene nucleotide sequence is introduced with a second vector. In some embodiments of this aspect, the first vector includes a first promoter operably linked to the at least one morphogene nucleotide sequence, and the second vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene nucleotide sequence is introduced before the at least one transgene nucleotide sequence. In some embodiments of this aspect, the at least one morphogene nucleotide sequence is introduced at the same time as the at least one transgene nucleotide sequence. In some embodiments of this aspect, the at least one morphogene nucleotide sequence and the at least one transgene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the introduction of the at least one morphogene nucleotide sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox. In some embodiments of this aspect, the method improves the number and quality of independent transgenic events per variety.

An additional aspect of the disclosure includes methods of producing a genetically altered sugarcane plant, including: (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 and at least one transgene nucleotide sequence to produce transgenic sugarcane cells; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further selecting the transgenic sugarcane cells between steps (b) and (c), or selecting the transgenic sugarcane cells after step (c), optionally by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, a combination of morphogene proteins is used. In some embodiments, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene protein sequence is introduced through microprojectile bombardments or nanoparticle delivery. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the introduction of the at least one morphogene protein sequence is transient. In some embodiments of this aspect, the genetically altered plant of step (d) does not include the at least one morphogene protein sequence. In some embodiments of this aspect, the method improves the number and quality of independent transgenic events per variety.

In some aspects, the present disclosure relates to a seed, plant part, or plant tissue from the genetically altered sugarcane plant of any of the above embodiments.

A further aspect of the disclosure includes methods of modifying the genome of a sugarcane cell, including (a) providing a sugarcane cell or tissue; (b) introducing a genome editing component, wherein the genome editing component targets one or more gene sequences in the sugarcane genome, and introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 into the sugarcane cell to produce a genetically modified sugarcane cell including one or more edited gene sequences; and (c) cultivating the genetically modified sugarcane cell for proliferation and/or regeneration. Some embodiments of this aspect further include (d) cultivating the genetically modified sugarcane cell into a genetically altered plantlet; and (e) growing the genetically altered plantlet into a genetically altered plant including the one or more edited gene sequences. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. Some embodiments of this aspect further include screening the sugarcane cell between steps (b) and (c), screening the sugarcane cell during step (c), or screening the sugarcane cell after step (c), and optionally further include selecting the genetically modified sugarcane cells between steps (b) and (c), or selecting the genetically modified sugarcane cell after step (c), optionally by using nucleotide-based screening methods or by using selectable markers. In some embodiments of this aspect, step (b) is achieved through *Agrobacterium* transformation, microprojectile bombardments, nanoparticle delivery, viral delivery, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, the genome editing component is introduced with a first vector and the at least one morphogene nucleotide sequence is introduced with a second vector. In some embodiments of this aspect, the first vector includes a first promoter operably linked to the genome editing component, and wherein the second vector includes a second promoter operably linked to the at least one morphogene nucleotide sequence. In some embodiments of this aspect, the first and second promoters are selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the genome editing component is introduced at the same time as the at least one morphogene nucleotide sequence. In some embodiments of this aspect, the genome editing component and the at least one morphogene nucleotide sequence are co-introduced with a vector. In some embodiments of this aspect, the vector includes a first promoter operably linked to the at least one morphogene nucleotide sequence, and the vector includes a second promoter operably linked to the genome editing component. In some embodiments of this aspect, the first and second promoters are selected from the group of a constitutive promoter, an inducible promoter, or a tissue-specific or cell-type-specific promoter. In some embodiments of this aspect, the introduction of the at least one morphogene nucleotide sequence is transient. In some embodiments of this aspect, the genetically altered plant of step (d) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox.

An additional aspect of the disclosure includes methods of modifying the genome of a sugarcane cell, including (a) providing a sugarcane cell or tissue; (b) introducing a genome editing component, wherein the genome editing component targets one or more gene sequences in the sugarcane genome, and introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 into the sugarcane cell to produce a genetically modified sugarcane cell including one or more edited gene sequences; and (c) cultivating the genetically modified sugarcane cells for proliferation and/or regeneration. Some embodiments of this aspect further include (d) cultivating the genetically modified sugarcane cell into a genetically altered plantlet; and (e) growing the genetically altered plantlet into a genetically altered plant including the one or more edited gene sequences. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further include selecting the genetically modified sugarcane cells between steps (b) and (c), or selecting the genetically modified sugarcane cells after step (c), optionally by using nucleotide-based screening methods or by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used. In some embodiments, one morphogene protein sequence, two morphogene protein sequences, or three morphogene protein sequences are introduced in step (b). In some embodiments of this aspect, the at least one morphogene protein sequence is introduced through microprojectile bombardments or nanoparticle delivery. In some embodiments of this aspect, the genome editing component is introduced with a vector. In some embodiments of this aspect, the vector includes a promoter operably linked to the genome editing component. In some embodiments of this aspect, the promoter is selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the at least one morphogene protein sequence is introduced before the genome editing component. In some embodiments of this aspect, the genome editing component is introduced at the same time as the at least one morphogene protein sequence. In some embodiments of this aspect, the introduction of the at least one morphogene protein sequence is transient. In some embodiments of this aspect, the genetically altered plant of step (d) does not include the at least one morphogene protein sequence.

Yet another aspect of the disclosure includes methods of increasing transformation efficiency of sugarcane cells, including (a) providing sugarcane cells or tissue; (b) introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 and at least one transgene nucleotide sequence into the sugarcane cells to produce transgenic sugarcane cells, wherein the transformation efficiency is increased as compared to a method of transforming sugarcane cells that does not use at least one morphogene nucleotide sequence; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. In some embodiments of this aspect, transformation efficiency is increased by at least 5% as compared to a method of transforming sugarcane cells that does not use at least one morphogene nucleotide sequence. In some embodiments of this aspect, transformation efficiency is increased by 50% to 100% as compared to a method of transforming sugarcane cells that does not use at least one morphogene nucleotide sequence. Some embodiments of this aspect further include screening the sugarcane cells between steps (b) and (c), s screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. In some embodiments of this aspect, step (b) is achieved through *Agrobacterium* transformation, microprojectile bombardments, nanoparticle delivery, viral delivery, or a combination thereof. In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one morphogene nucleotide sequence is introduced with a first vector and the at least one transgene nucleotide sequence is introduced with a second vector. In some embodiments of this aspect, the first vector includes a first promoter operably linked to the at least one morphogene nucleotide sequence, and the second vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene nucleotide sequence is introduced before the at least one transgene nucleotide sequence. In some embodiments of this aspect, the at least one morphogene nucleotide sequence is introduced at the same time as the at least one transgene nucleotide sequence. In some embodiments of this aspect, the at least one morphogene nucleotide sequence and the at least one transgene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the introduction of the at least one morphogene nucleotide sequence is transient. In some embodiments of this aspect, the genetically altered plant of step (d) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox. In some embodiments of this aspect, the method improves the number and quality of independent transgenic events per variety.

Still another aspect of the disclosure includes methods of increasing transformation efficiency of sugarcane cells, including (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 and at least one transgene nucleotide sequence into the sugarcane cells to produce transgenic sugarcane cells, wherein the transformation efficiency is increased as compared to a method of transforming sugarcane cells that does not use at least one morphogene protein sequence; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. In some embodiments of this aspect, transformation efficiency is increased by at least 5% as compared to a method of transforming sugarcane cells that does not use at least one morphogene protein sequence. In some embodiments of this aspect, transformation efficiency is increased by 50% to 100% as compared to a method of transforming sugarcane cells that does not use at least one morphogene protein sequence. Some embodiments of this aspect further include screening the sugarcane cells between steps (b) and (c), screening the plantlets after step (c), or screening the plants after step (d) to identify the transgene. Some embodiments of this aspect further include selecting the transgenic sugarcane cells between steps (b) and (c), or selecting the genetically altered plantlets after step (c), optionally by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, a combination of morphogene proteins is used. In some embodiments, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene protein sequence is introduced through microprojectile bombardments or nanoparticle delivery. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the introduction of the at least one morphogene protein sequence is transient. In some embodiments of this aspect, the genetically altered plant of step (e) does not include the at least one morphogene protein sequence. In some embodiments of this aspect, the method improves the number and quality of independent transgenic events per variety.

An additional aspect of the disclosure includes methods of increasing the genome editing rate of a genome of a sugarcane cell, including (a) providing a sugarcane cell; (b) introducing a genome editing component, wherein the genome editing component targets one or more gene sequences in the sugarcane genome, and introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 into the sugarcane cell to produce a genetically modified sugarcane cell including one or more edited gene sequences, wherein the genome editing rate is increased as compared to a method of genome editing that does not use at least one morphogene nucleotide sequence; (c) cultivating the genetically modified sugarcane cell for proliferation and/or regeneration. Some embodiments of this aspect further include (d) cultivating the genetically modified sugarcane cell into a genetically modified plantlet; and (e) growing the genetically modified plantlet into a genetically modified plant including one or more edited gene sequences. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. Some embodiments of this aspect further include screening the sugarcane cells between steps (b) and (c), screening the sugarcane cells during step (c), or screening the sugarcane cells after step (c), and optionally further include selecting the genetically modified sugarcane cells between steps (b) and (c), or selecting the genetically modified sugarcane cells after step (c), optionally by using nucleotide-based screening methods or by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used In some embodiments of this aspect a combination of morphogenes is used. In some embodiments, one morphogene nucleotide sequence, two morphogene nucleotide sequences, or three morphogene nucleotide sequences are introduced in step (b). In some embodiments of this aspect, the genome editing component is introduced with a first vector and the at least one morphogene nucleotide sequence is introduced with a second vector. In some embodiments of this aspect, the first vector includes a first promoter operably linked to the genome editing component, and wherein the second vector includes a second promoter operably linked to the at least one morphogene nucleotide sequence. In some embodiments of this aspect, the first and second promoters are selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the genome editing component is introduced before the at least one morphogene nucleotide sequence. In some embodiments of this aspect, the genome editing component is introduced at the same time as the at least one morphogene nucleotide sequence. In some embodiments of this aspect, the genome editing component is introduced after the at least one morphogene nucleotide sequence. In some embodiments of this aspect, the genome editing component and the at least one morphogene nucleotide sequence are co-introduced with a vector. In some embodiments of this aspect, the introduction of the at least one morphogene protein sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox.

An additional aspect of the disclosure includes methods of increasing the genome editing rate of a genome of a sugarcane cell, including (a) providing a sugarcane cell or tissue; (b) introducing a genome editing component, wherein the genome editing component targets one or more gene sequences in the sugarcane genome, and introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 into the sugarcane cell to produce a genetically modified sugarcane cell including one or more edited gene sequences; and (c) cultivating the genetically modified sugarcane cells for proliferation and/or regeneration. Some embodiments of this aspect further include (d) cultivating the genetically modified sugarcane cell into a genetically altered plantlet; and (e) growing the genetically altered plantlet into a genetically altered plant including the one or more edited gene sequences. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further include selecting the genetically modified sugarcane cells between steps (b) and (c), or selecting the genetically modified sugarcane cells after step (c), optionally by using nucleotide-based screening methods. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used. In some embodiments, one morphogene protein sequence, two morphogene protein sequences, or three morphogene protein sequences are introduced in step (b). In some embodiments of this aspect, the at least one morphogene protein sequence is introduced through microprojectile bombardments or nanoparticle delivery. In some embodiments of this aspect, the genome editing component is introduced with a vector. In some embodiments of this aspect, the vector includes a promoter operably linked to the genome editing component. In some embodiments of this aspect, the promoter is selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the at least one morphogene protein sequence is introduced before the genome editing component. In some embodiments of this aspect, the genome editing component is introduced at the same time as the at least one morphogene protein sequence. In some embodiments of this aspect, the introduction of the at least one morphogene protein sequence is transient. In some embodiments of this aspect, the genetically altered plant of step (e) does not include the at least one morphogene protein sequence.

BRIEF DESCRIPTION OF THE DRAWINGS

FIG. 2A shows multiple options for the delivery of genome editing reagents to generate HR events. In the top row, the first option of a single construct containing genome editing reagents pSCBV-ScoLbCPF1-LWcrRNAarray-tAtHSP18, HR template, a fluorescent reporter pFMV-erGFP-tPin2A, a selectable marker pZmUbi-NPTII-T-Nos, and morphogenic genes is shown. In the second row from the top, the second option of a construct containing pSCBV-ScoLbCPF1-LWcrRNAarray-tAtHSP18, a fluorescent reporter pFMV-erGFP-tPin2A, a selectable marker pZmUbi-NPTII-T-Nos, and morphogenic genes with the HR template being delivered separately is shown. In the third row from the top, the third option of a construct containing a fluorescent reporter pFMV-erGFP-tPin2A, a selectable marker pZmUbi-NPTII-T-Nos, and morphogenic genes with the HR template being delivered separately and the genome editing reagents being delivered separately in the form of ribonucleoprotein (RNP) is shown. Each of the plasmids further contains a left border (LB) and right border (RB). In the bottom row, delivery methods are shown, with *Agrobacterium* transformation (Agro) for the first plasmid option and microprojectile bombardment (Bombardment) for all three options. Both delivery methods can be used with leaf disks or calli (plant material). FIG. 2B shows multiple options for the delivery of genome editing reagents to generate KO events. In the top row, the first option of a single construct containing genome editing reagents pSCBV-ScoLbCPF1-LWcrRNAarray-tAtHSP18, a fluorescent reporter pFMV-erGFP-tPin2A, a selectable marker pZmUbi-NPTII-T-Nos, and morphogenic genes is shown. In the middle row, the second option of a construct containing a fluorescent reporter pFMV-erGFP-tPin2A, a selectable marker pZmUbi-NPTII-T-Nos, and morphogenic genes with the genome editing reagents being delivered separately in the form of ribonucleoprotein (RNP) is shown. Each of the plasmids further contains a left border (LB) and right border (RB). In the bottom row, delivery methods are shown, with *Agrobacterium* transformation (Agro) for the first plasmid option and microprojectile bombardment (Bombardment) for both options. Both delivery methods can be used with leaf disks or calli (plant material).

FIG. 4A shows results from leaf disk transformation with the morphogenes *Brassica oleracea* LEC2 (BoLEC2, SEQ ID NO: 11), *Saccharum spontaneum* LEC2 (SsLEC2, SEQ ID NO: 10), *Brachypodium distachyon* EMK1/PLT2 (BdEMK1, SEQ ID NO: 12), *Panicum hallii* RKD4 (PhRKD4, SEQ ID NO: 14), and *Saccharum* spp. hybrid AGL15 (SsAGL15, SEQ ID NO: 1) were tested. FIG. 4B shows results from leaf disk transformation with the morphogenes *Brassica napus* AGL15 (BnAGL15, SEQ ID NO: 2), *Saccharum spontaneum* SERK1 (SsSERK1, SEQ ID NO: 15), *Oryza longistaminata* GRF5 (OlGRF5, SEQ ID NO: 8), *Saccharum spontaneum* GRF5 (SsGRF5, SEQ ID NO: 9), *Triticum urartu* BBM (TuBBM, SEQ ID NO: 4), and *Panicum hallii* WUS (PhWUS, SEQ ID NO: 20). In FIGS. 4A-4B, each experiment included a WUS control (positive control, data not shown) and a GFP control (negative control, without morphogene), as well as multiple morphogenes (indicated by legend below graph); the y-axis shows the percentage of disks with fluorescence (tdTomato or GFP) clusters on Day 21 after transformation; and the x-axis shows the control or the morphogene tested.

FIG. 5A shows a summary graph of the results of transformations of calli with the morphogenes *Panicum hallii* WUS (PhWUS, SEQ ID NO: 20), *Panicum hallii* RKD4 (PhRKD4, SEQ Id NO: 14), *Brassica oleracea* LEC2 (BoLEC2, SEQ ID NO: 11), and *Saccharum spontaneum* LEC2 (SsLEC2, SEQ ID NO: 10) were tested. FIG. 5B shows a summary graph of the results of transformations of calli with the morphogenes *Triticum urartu* BBM (TuBBM, SEQ ID NO: 4) and *Saccharum spontaneum* BBM (SsBBM, SEQ ID NO: 3) were tested. In FIGS. 5A-5B, each experiment included a WUS control (positive control, data not shown) and a GFP control (negative control, without morphogene), as well as multiple morphogenes (indicated by legend below graph); the y-axis expresses the percentage of disks with fluorescence (tdTomato or GFP) clusters on Day 30; and the x-axis shows the control or morphogene tested. Both summary graphs show results for a GFP control (negative control) as well as the candidate morphogenes. FIG. 5C shows fluorescence (RFP, top row) and brightfield (bottom row) images of the GFP negative control (No morphogene), *Zea mays* WUS (ZmWUS) positive control, *Panicum hallii* RKD4 (PhRKD4, SEQ ID NO: 14), and *Panicum hallii* WUS (PhWUS, SEQ ID NO: 20) transformations of individual calli. FIG. 5D shows fluorescence (RFP, top row) and brightfield (bottom row) images of the no morphogene (negative control), ZmWUS (positive control), and *Panicum hallii* RKD4 (PhRKD4, SEQ ID NO: 14) transformations of plates of calli on Day 40. FIG. 5E shows brightfield images of the ZmWUS (positive control), and *Panicum hallii* RKD4 (RKD4, SEQ ID NO: 14) transformations of plates of calli on Day 40.

DETAILED DESCRIPTION

Figure 1:
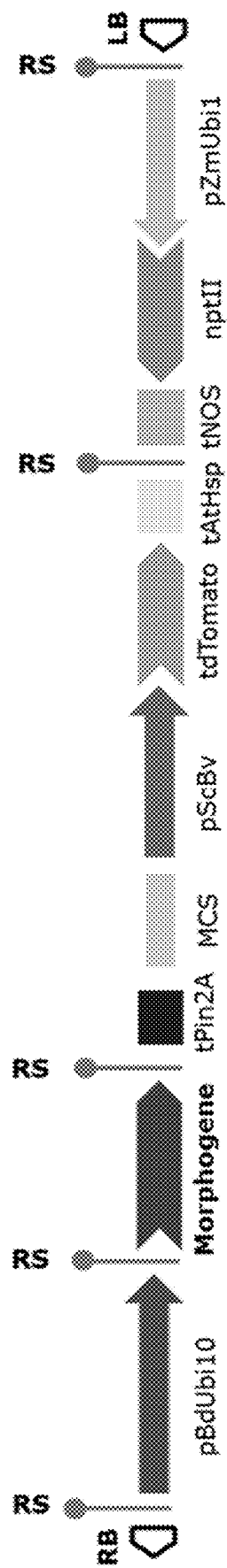
FIG. 1 shows a schematic of an expression cassette for co-introduction of a morphogene and a trait gene of interest on a single vector. The expression cassette contains the following: pBdUbi10::morphogene::tPin2A, where pBdUBi10 is the *Brachypodium distachyon* ubiquitin promoter, morphogene is a candidate morphogene, and tPin2A is the Pin2A terminator; pScBv::tdTomato::tAtHsp, where pScBv is the sugarcane baciliform virus promoter, tdTomato is red fluorescent protein, and tAtHsp is the *Arabidopsis thaliana* heat shock protein (Hsp) terminator; and pZmUbi1::nptII::tNOS, where pZmUbi1 is the *Zea mays* ubiquitin promoter, nptII is the kanamycin resistance gene, and tNOS is the nopaline synthase terminator. The fluorescent protein tdTomato is an exemplary transgene that is used as a visual reporter for transgene integration, while the nptII gene is used as a selectable marker. In addition to these, the expression cassette includes a right border (RB), restriction sites (RS), multiple cloning site (MCS), and a left border (LB).

The following description sets forth exemplary methods, parameters, and the like. It should be recognized, however, that such description is not intended as a limitation on the scope of the present disclosure but is instead provided as a description of exemplary embodiments.

Methods of Producing Genetically Altered Plants

An aspect of the disclosure includes methods of producing a genetically altered sugarcane plant, including: (a) providing sugarcane cells or tissue; (b) introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 and at least one transgene nucleotide sequence to produce transgenic sugarcane cells; and (c) cultivating the transgenic sugarcane cells for proliferation and/or regeneration. In some embodiments of this aspect, the morphogene affects proliferation, regeneration, or both. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. Some embodiments of this aspect further include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. Some embodiments of this aspect further include screening the sugarcane cells between steps (b) and (c), screening the plantlets after step (d), or screening the plants after step (e) to identify the transgene. In some embodiments, screening may be done using PCR, ELISA, fluorescence detection, or other screening methods known in the art. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. In some embodiments of this aspect, step (b) is achieved through *Agrobacterium* transformation, microprojectile bombardments, nanoparticle delivery, or viral delivery. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments, the agronomic trait includes a biomass trait, a sucrose trait, drought tolerance, a flowering trait, and/or an aluminum tolerance trait. In some embodiments of this aspect, a combination of morphogenes is used. In some embodiments, one morphogene nucleotide sequence, two morphogene nucleotide sequences, three morphogene nucleotide sequences, four morphogene nucleotide sequences, five morphogene nucleotide sequences, six morphogene nucleotide sequences, seven morphogene nucleotide sequences, eight morphogene nucleotide sequences, nine morphogene nucleotide sequences, ten morphogene nucleotide sequences, eleven morphogene nucleotide sequences, twelve morphogene nucleotide sequences, thirteen morphogene nucleotide sequences, fourteen morphogene nucleotide sequences, fifteen morphogene nucleotide sequences, sixteen morphogene nucleotide sequences, seventeen morphogene nucleotide sequences, eighteen morphogene nucleotide sequences, nineteen morphogene nucleotide sequences, or twenty morphogene nucleotide sequences are introduced in step (b). In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one morphogene nucleotide sequence is introduced with a first vector and the at least one transgene nucleotide sequence is introduced with a second vector. In some embodiments of this aspect, the first vector includes a first promoter operably linked to the at least one morphogene nucleotide sequence, and the second vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene nucleotide sequence is introduced before the at least one transgene nucleotide sequence. In some embodiments of this aspect, the at least one morphogene nucleotide sequence is introduced at the same time as the at least one transgene nucleotide sequence. In some embodiments of this aspect, the at least one morphogene nucleotide sequence is introduced after the at least one transgene nucleotide sequence. In some embodiments of this aspect, the at least one morphogene nucleotide sequence and the at least one transgene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments, the vector used for co-introduction includes the expression cassette shown in FIG. 1. In some embodiments of this aspect, the introduction of the at least one morphogene nucleotide sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox. In some embodiments of this aspect, the method improves the number and quality of independent transgenic events per variety.

An additional aspect of the disclosure includes methods of producing a genetically altered sugarcane plant, including: (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 and at least one transgene nucleotide sequence to produce transgenic sugarcane cells; and (c) cultivating the transgenic sugarcane cells for proliferation and/or regeneration. In some embodiments of this aspect, the morphogene affects proliferation, regeneration, or both. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. Some embodiments of this aspect further include screening the sugarcane cells between steps (b) and (c), screening the plantlets after step (d), or screening the plants after step (e) to identify the transgene. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. In some embodiments, screening may be done using PCR, ELISA, fluorescence detection, sequencing, or other screening methods known in the art. In some embodiments of this aspect, step (b) is achieved through Agrobacterium transformation, microprojectile bombardments, nanoparticle delivery, or viral delivery. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments, the agronomic trait includes a biomass trait, a sucrose trait, a flowering trait, drought tolerance, and/or an aluminum tolerance trait. In some embodiments, the transgene nucleotide sequence includes a BT nucleotide sequence, a Cry nucleotide sequence, or a VIP nucleotide sequence. In some embodiments of this aspect, a combination of morphogene proteins is used. In some embodiments, one morphogene protein sequence, two morphogene protein sequences, three morphogene protein sequences, four morphogene protein sequences, five morphogene protein sequences, six morphogene protein sequences, seven morphogene protein sequences, eight morphogene protein sequences, nine morphogene protein sequences, ten morphogene protein sequences, eleven morphogene protein sequences, twelve morphogene protein sequences, thirteen morphogene protein sequences, fourteen morphogene protein sequences, fifteen morphogene protein sequences, sixteen morphogene protein sequences, seventeen morphogene protein sequences, eighteen morphogene protein sequences, nineteen morphogene protein sequences, or twenty morphogene protein sequences are introduced in step (b). In some embodiments of this aspect, a combination of morphogene proteins is used. In some embodiments, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene protein sequence is introduced through microprojectile bombardments or nanoparticle delivery. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the at least one morphogene protein sequence is introduced after the at least one transgene nucleotide sequence. In some embodiments of this aspect, the introduction of the at least one morphogene protein sequence is transient. Most means of introducing protein sequences known in the art result in degradation of the protein over time (i.e., transient expression). In some embodiments of this aspect, the genetically altered plant of step (e) does not include the at least one morphogene protein sequence. In some embodiments of this aspect, the method improves the number and quality of independent transgenic events per variety.

The protocol of *Agrobacterium* transformation of a cell or tissue and subsequently regenerating it includes the following general stages: I: production or preparation of a cell or tissue (explant); II: transformation; III: co-cultivation (or co-culture) and rest; IV: selection; and V: regeneration and elongation. Stages II through V each require suitable culture media. Those skilled in the art are familiar with the composition of suitable culture media for the generation of transformable tissue (or transformable explant) (stage II: transformation), as well as the means of the co-cultivation stages (stage III: co-cultivation+rest), selection (stage IV: selection), and regeneration (stage V: regeneration+elongation). Preferably, the culture media used are based on compositions including ingredients such as MS salts (Murashige and Skoog, 1962), sucrose, and vitamins B5. Optionally, the following can also be added: amino acids selected from the group of proline and asparagine; casein hydrolysate; citric acid; mannitol; copper sulfate; glycine; gelling agent; auxins; antibiotics; acetosyringone; and selection agents. The use of hormones, e.g. auxins and/or cytokinins, are especially important in the steps of transformable tissue or transformable explant generation (stage I-II), co-cultivation (stage III) and selection (stage IV), as is the selection agents, e.g., ammonium glufosinate, in the selection medium (stage IV). Suitable explants for plant transformation includes, without limitation: callus, undifferentiated callus, immature and mature embryos, immature zygotic embryo, immature cotyledon, embryonic axis, suspension culture cells, protoplasts, leaf, leaf cells, leaf disks, root cells, phloem cells, pollen, seeds, suspension cultures, embryos, zygotic embryos, somatic embryos, embryogenic callus, meristem, somatic meristems, organogenic callus, protoplasts, leaf bases, leaves from mature plants, leaf tips, immature inflorescences, cotyledons, meristematic regions, cells from stems, cells from roots, cells from shoots, gametophytes, sporophytes, microspores, single cells and hypocotyl cells.

In some aspects, the present disclosure relates to a seed, plant part, or plant tissue from the genetically altered sugarcane plant of any of the above embodiments. In some embodiments, the plant part is selected from the group of leaf, stem, anther, pistil, root, fruit, flower, seed, cotyledon, hypocotyl, embryo, or meristematic cell. Plant parts include differentiated and undifferentiated tissues including, but not limited to, roots, stems, shoots, leaves, pollen, seeds.

In some aspects, the present disclosure relates to a pollen grain or an ovule of the genetically altered sugarcane plant of any of the above embodiments.

In some aspects, the present disclosure relates to a protoplast from the genetically altered sugarcane plant of any of the above embodiments.

In some aspects, the present disclosure relates to a tissue culture produced from protoplasts or cells from the genetically altered plant of any of the above embodiments. Plant cells can be differentiated or undifferentiated (e.g., callus, undifferentiated callus, immature and mature embryos, immature zygotic embryo, immature cotyledon, embryonic axis, suspension culture cells, protoplasts, leaf, leaf cells, root cells, phloem cells and pollen). Plant cells include, without limitation, cells from seeds, suspension cultures, explants, immature embryos, embryos, zygotic embryos, somatic embryos, embryogenic callus, meristem, somatic meristems, organogenic callus, protoplasts, leaf bases, leaves from mature plants, leaf tips, immature inflorescences, cotyledons, immature cotyledons, embryonic axes, meristematic regions, callus tissue, cells from leaves, cells from stems, cells from roots, cells from shoots, gametophytes, sporophytes, pollen and microspores. Plant cells further include various forms of cells in culture (e. g., single cells, protoplasts, embryos, and callus tissue), wherein the protoplasts or cells are produced from a plant part selected from the group of leaf, stem, anther, pistil, root, fruit, flower, seed, cotyledon, hypocotyl, embryo, or meristematic cell.

Sugarcane plants of the present disclosure include species and hybrids in the genus *Saccharum*, e.g., *Saccharum officinarum, Saccharum sinense, Saccharum barberi, Saccharum robustum, Saccharum spontaneum, Saccharum* spp., *Saccharum* spp. hybrid, etc. Methods of the present disclosure improve genotype independence of transformation methods.

LOOM In some aspects, the present disclosure relates to methods of producing genetically altered plants, wherein plant cells or tissue are used in place of sugarcane cells in any of the above methods. The plant cells or tissue may be derived from plants including, without limitations, corn (e.g., maize, *Zea mays*), barley (e.g., *Hordeum vulgare*), millet (e.g., finger millet, fonio millet, foxtail millet, pearl millet, barnyard millets, *Eleusine coracana, Panicum sumatrense, Panicum milaceum, Pennisetum glaucum, Digitaria* spp., *Echinocloa* spp.), oat (e.g., *Avena sativa*), rice (e.g., indica rice, japonica rice, aromatic rice, glutinous rice, *Oryza sativa, Oryza glaberrima*), rye (e.g., *Secale cereale, Secale cereanum*), sugarcane (e.g., *Saccharum* sp.), setaria (e.g., *Setaria italica, Setaria viridis*), *Brachypodium* sp., sorghum (e.g., *Sorghum bicolor*), teff (e.g., *Eragrostis tef*), triticale (e.g., X *Triticosecale* Wittmack, *Triticosecale schlanstedtense* Wittm., *Triticosecale neoblaringhemii* A. Camus, *Triticosecale neoblaringhemii* A. Camus), wheat (e.g., common wheat, spelt, durum, einkorn, emmer, kamut, *Triticum aestivum, Triticum spelta, Triticum durum, Triticum urartu, Triticum monococcum, Triticum turanicum, Triticum* spp.), switchgrass (e.g., *Panicum virgatum*), *Brassica* sp., tobacco (e.g., *Nicotiana benthamiana, Nicotiana tabacum*), peanut (*Arachis hypogaea*), banana (*Musa* sp.), potato (*Solanum tuberosum*), strawberry (*Fragaria ananassa*), coffee (*Coffea arabica*), cotton (*Gossypium hirsutum*), tomato (*Solanum lycopersicum*) or any other polyploid and/or vegetatively propagated plant species.

Methods of Improving the Efficiency of Transformation

Transformation frequency (TF) or transformation efficiency (TE) in general, is measured at two stages in the transformation process: (1) Transient transformation frequency and (2) Stable transformation frequency. Transient transformation frequency represents the efficiency of gene delivery. It is calculated as the percentage of explants expressing a marker gene (e.g., fluorescent markers such as GFP, CFP, dsRED, etc., or GUS gene). This is measured in the beginning of the transformation process. Stable transformation frequency is the percentage of explants producing transgenic events. It is calculated at the end of the transformation process. There are many different ways to calculate TF. In many plant species, the explant is definite-sized and countable (e.g., cotyledons in soybean, hypocotyl segments in cotton). In this case, TF is calculated based on the number of explants used, i.e., the percentage of explants producing transgenic events. In most monocot plant species (e.g., rice, maize, sugarcane), embryogenic callus pieces are used as explants. In the case of callus, TF is calculated in two ways. The first is a calculation based on the number of callus pieces used (size is a variable), i.e., the percentage of explants producing transgenic events. The second is a calculation based on the weight of the callus tissue used (e.g., TF per gram callus tissue). In the sugarcane embodiments of the present disclosure, TF is calculated based on the number of callus pieces used for transformation.

Methods and compositions for improving the efficiency of sugarcane cell transformation are provided herein. Cell transformation can be achieved using *Agrobacterium* transformation, microprojectile bombardment, nanoparticle delivery, viral delivery, or other methods of plant cell transformation known to those skilled in the art. Cell transformation may use vectors, and may either be transient or stable. When the transformation is stable, the vector containing the morphogene expression cassette may also contain means for excising the morphogene such that it is no longer present or expressed in the resultant sugarcane plant or to control its expression, e.g., inducible promoters and/or tissue specific promoters. Excision can be achieved using Cre-Lox recombination or other inducible excision systems known in the art. The sugarcane cells to be transformed can be leaf disc cells, callus cells, protoplast cells, or any sugarcane cells or tissues receptive to the introduction and uptake of heterogenous DNA, RNA, or protein.

In one embodiment of the disclosure, a morphogene and a trait gene of interest are co-introduced via sugarcane cell transformation in an expression cassette on a single vector (e.g., the expression cassette of FIG. 1). In another embodiment of the disclosure, the morphogene and trait gene of interest are introduced in expression cassettes on separate vectors. In yet another embodiment of the disclosure, two or more morphogenes can be co-introduced along with the trait gene of interest. In one embodiment of the disclosure, the two or more morphogenes can be introduced on a single vector. In another embodiment of the disclosure, the two or more morphogenes can be introduced on separate vectors.

The co-introduced morphogene is encoded by a polynucleotide selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20. These polynucleotides encode the polypeptides of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40. Each of these morphogenes belongs to a protein family that has been described as being involved in processes of plant morphogenesis or regeneration (see "Morphogenes" section, below). The morphogenes of the present disclosure were selected based upon both their sequence similarity to polynucleotides encoding known proteins of morphogene families and the presence of key protein domain motifs suggesting functionality. The selection process is described in more detail in Example 1, below.

Figure 2A:
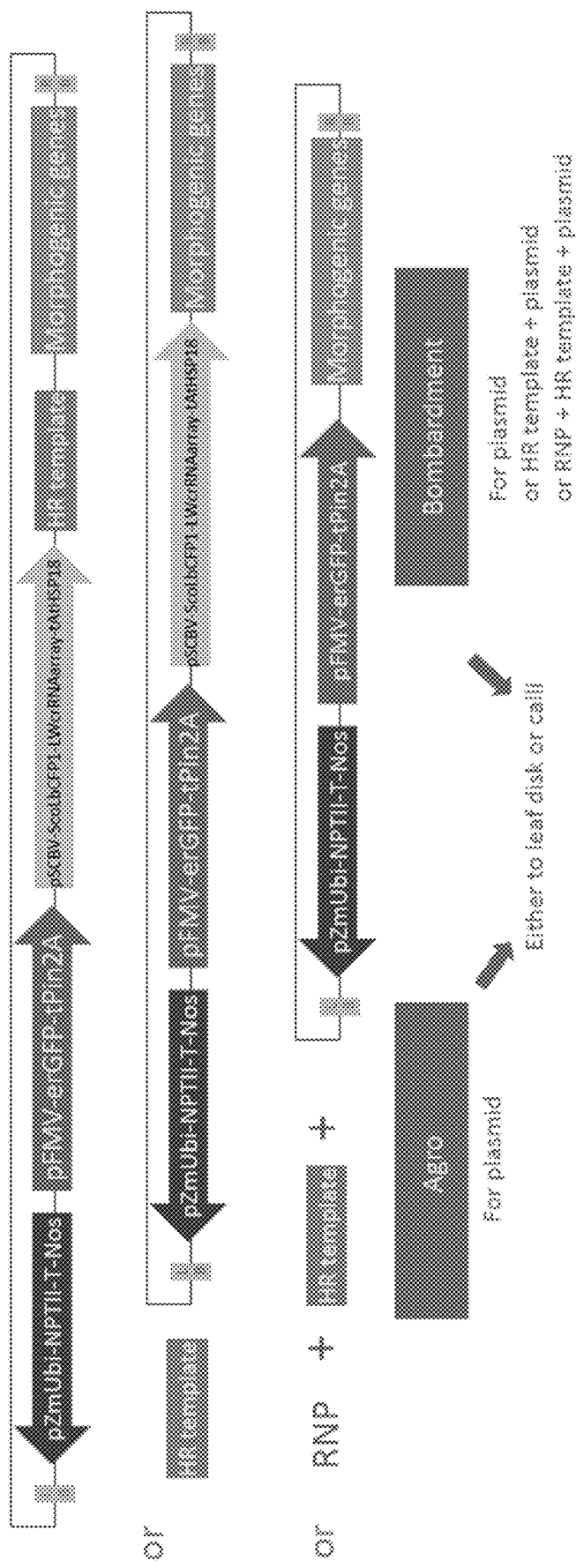
FIGS. 2A-2B show schematics for the delivery of genome editing reagents to generate homologous recombination (HR) events or knockout (KO) events.
Figure 2B:
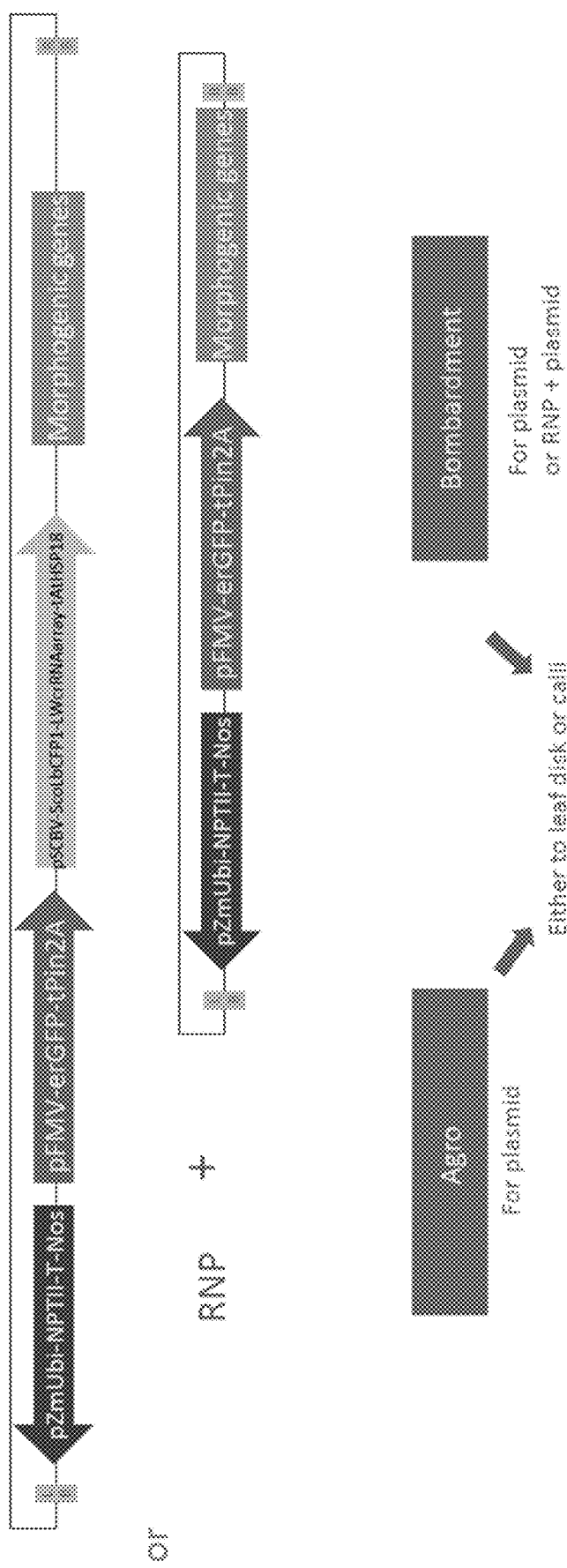
Figure 3:
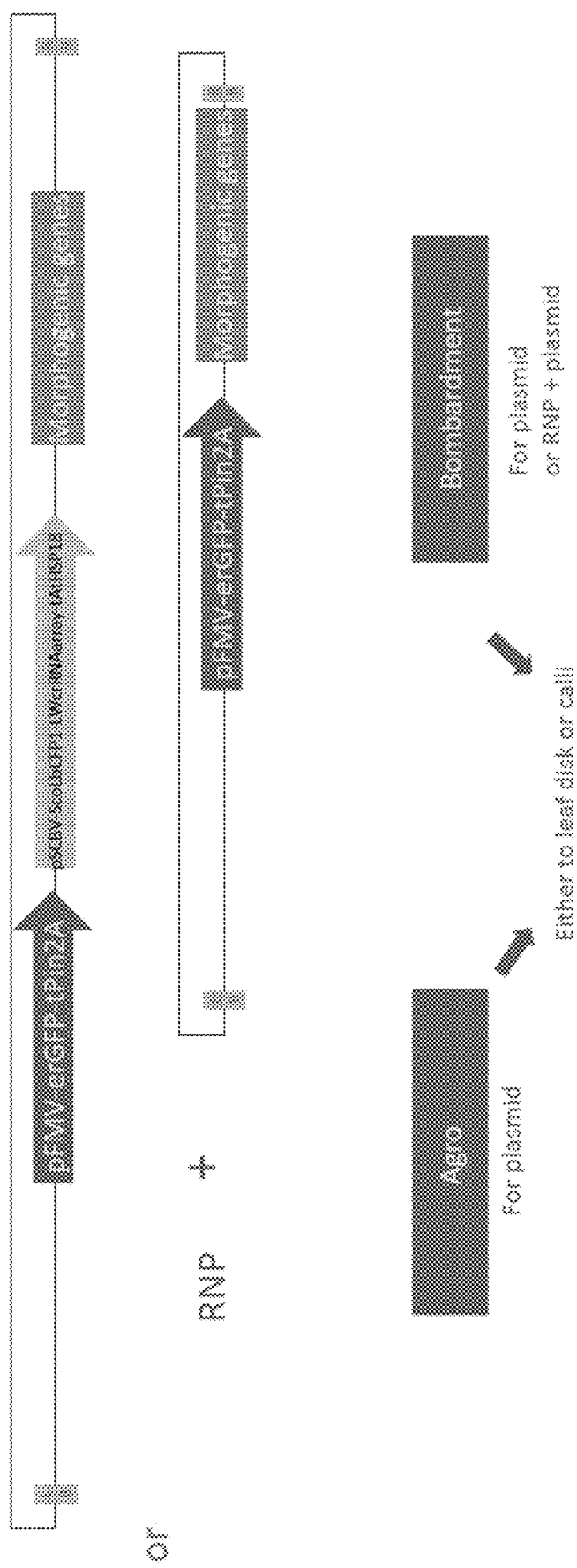
FIG. 3 shows schematics for the delivery of genome editing reagents to generate transgene-free knockout (KO) events. In the top row, the first option of a single construct containing genome editing reagents pSCBV-ScoLbCPF1-LWcrRNAarray-tAtHSP18, a fluorescent reporter pFMV-erGFP-tPin2A, and morphogenic genes is shown. In the middle row, the second option of a construct containing a fluorescent reporter a fluorescent reporter pFMV-erGFP-tPin2A and morphogenic genes, with the genome editing reagents being delivered separately in the form of ribonucleoprotein (RNP) is shown. Each of the plasmids further contains a left border (LB) and right border (RB). In the bottom row, delivery methods are shown, with *Agrobacterium* transformation (Agro) for the first plasmid option and microprojectile bombardment (Bombardment) for both options. Both delivery methods can be used with any explant types, including but not limited to leaf disks or calli (plant material).

A further aspect of the disclosure includes methods of modifying the genome of a sugarcane cell, including (a) providing a sugarcane cell or tissue; (b) introducing a genome editing component, wherein the genome editing component targets one or more gene sequences in the sugarcane genome, and introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 into the sugarcane cell to produce a genetically modified sugarcane cell including one or more edited gene sequences; and (c) cultivating the genetically modified sugarcane cell for proliferation and/or regeneration. In some embodiments of this aspect, the morphogene affects proliferation, regeneration, or both. Some embodiments of this aspect further include (d) cultivating genetically modified sugarcane cell into a genetically altered plantlet; and (e) growing the genetically altered plantlet into a genetically altered plant including the one or more edited gene sequences. Some embodiments of this aspect further include screening the sugarcane cell between steps (b) and (c), screening the sugarcane cell during step (c), or screening the sugarcane cell after step (c), and optionally further including selecting the genetically modified sugarcane cell between steps (b) and (c), or selecting the genetically modified sugarcane cell after step (c), optionally by using selectable markers. Some embodiments of this aspect further include screening the sugarcane cell between steps (b) and (c), screening the plantlet after step (d), or screening the plans after step (e) to identify the edited gene sequence. In some embodiments, screening may be done using PCR, ELISA, fluorescence detection, sequencing, or other screening methods known in the art. Some embodiments of this aspect further include selecting the genetically modified sugarcane cell between steps (b) and (c), or selecting the genetically modified plantlet after step (d), optionally by using selectable markers. These selectable markers may be nptII, BAR, EPSPS, and/or any other suitable selectable marker. In some embodiments of this aspect, step (b) is achieved through *Agrobacterium* transformation, microprojectile bombardments, nanoparticle delivery, or viral delivery. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, the gene sequences are agronomic trait gene sequences, herbicide resistance gene sequences(e.g., CP4-EPSPS, BAR, ALS, etc.), or disease/pest resistance gene sequences (e.g., BT, Cry, VIP, etc.). Agronomic traits include biomass, sucrose content, flowering time, drought tolerance, and aluminum tolerance. In some embodiments of this aspect, a combination of morphogenes is used. In some embodiments, one morphogene nucleotide sequence, two morphogene nucleotide sequences, three morphogene nucleotide sequences, four morphogene nucleotide sequences, five morphogene nucleotide sequences, six morphogene nucleotide sequences, seven morphogene nucleotide sequences, eight morphogene nucleotide sequences, nine morphogene nucleotide sequences, ten morphogene nucleotide sequences, eleven morphogene nucleotide sequences, twelve morphogene nucleotide sequences, thirteen morphogene nucleotide sequences, fourteen morphogene nucleotide sequences, fifteen morphogene nucleotide sequences, sixteen morphogene nucleotide sequences, seventeen morphogene nucleotide sequences, eighteen morphogene nucleotide sequences, nineteen morphogene nucleotide sequences, or twenty morphogene nucleotide sequences are introduced in step (b). In some embodiments of this aspect, a combination of morphogenes is used. In some embodiments, one morphogene nucleotide sequence, two morphogene nucleotide sequences, or three morphogene nucleotide sequences are introduced in step (b). FIGS. 2A-2B show options for generating homologous recombination (HR) or knockout (KO) events, and provide vector components that may be used in some embodiments of this aspect. FIG. 3 shows options for generating transgene-free knockout events, and provide vector components that may be used in some embodiments of this aspect. In some embodiments of this aspect, the genome editing component is introduced with a first vector and the at least one morphogene nucleotide sequence is introduced with a second vector. In some embodiments of this aspect, the first vector includes a first promoter operably linked to the genome editing component, and wherein the second vector includes a second promoter operably linked to the at least one morphogene nucleotide sequence. In some embodiments of this aspect, the first and second promoters are selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the genome editing component is introduced before the at least one morphogene nucleotide sequence. In some embodiments of this aspect, the genome editing component is introduced at the same time as the at least one morphogene nucleotide sequence. In some embodiments of this aspect, the genome editing component is introduced after as the at least one morphogene nucleotide sequence. In some embodiments of this aspect, the genome editing component and the at least one morphogene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the vector used for co-introduction includes the expression cassette of FIG. 1. In some embodiments of this aspect, the introduction of the at least one morphogene nucleotide sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox.

An additional aspect of the disclosure includes methods of modifying the genome of a sugarcane cell, including (a) providing a sugarcane cell or tissue; (b) introducing a genome editing component, wherein the genome editing component targets one or more gene sequences in the sugarcane genome, and introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 into the sugarcane cell to produce a genetically modified sugarcane cell including one or more edited gene sequences; and (c) cultivating the genetically modified sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further include selecting the genetically modified sugarcane cells between steps (b) and (c), or selecting the genetically modified sugarcane cells after step (c), optionally by using nucleotide-based screening methods or by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used. In some embodiments, one morphogene protein sequence, two morphogene protein sequences, or three morphogene protein sequences are introduced in step (b). In some embodiments of this aspect, the at least one morphogene protein sequence is introduced through microprojectile bombardments or nanoparticle delivery. In some embodiments of this aspect, the genome editing component is introduced with a vector. In some embodiments of this aspect, the vector includes a promoter operably linked to the genome editing component. In some embodiments of this aspect, the promoter is selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the at least one morphogene protein sequence is introduced before the genome editing component. In some embodiments of this aspect, the genome editing component is introduced at the same time as the at least one morphogene protein sequence. In some embodiments of this aspect, the introduction of the at least one morphogene protein sequence is transient. In some embodiments of this aspect, the genetically altered plant of step (e) does not include the at least one morphogene protein sequence.

Yet another aspect of the disclosure includes methods of increasing transformation efficiency of sugarcane cells, including (a) providing sugarcane cells or tissue; (b) introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 and at least one transgene nucleotide sequence into the sugarcane cells to produce transgenic sugarcane cells, wherein the transformation efficiency is increased as compared to a method of transforming sugarcane cells that does not use at least one morphogene nucleotide sequence; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. Some embodiments of this aspect include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. In some embodiments of this aspect, transformation efficiency is increased by at least 5% as compared to a method of transforming sugarcane cells that does not use at least one morphogene nucleotide sequence. In some embodiments of this aspect, transformation is increased by 5%, 6%, 7%, 8%, 9%, 10%, 11%, 12%, 13%, 14%, 15%, 16%, 17%, 18%, 19%, 20%, 21%, 22%, 23%, or 24%. In some embodiments of this aspect, transformation efficiency is increased by 50% to 100% as compared to a method of transforming sugarcane cells that does not use at least one morphogene nucleotide sequence. The increase in efficiency provided by the present methods represents a significant improvement over present methods, as some recalcitrant sugarcane varieties have less than 1% of transformation efficiency without the use of morphogenes. Some embodiments of this aspect further include screening the sugarcane cells between steps (b) and (c), screening the plantlets after step (d), or screening the plants after step (e) to identify the transgene. In some embodiments, screening may be done using PCR, ELISA, fluorescence detection, sequencing, or other screening methods known in the art. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. In some embodiments of this aspect, step (b) is achieved through *Agrobacterium* transformation, microprojectile bombardments, nanoparticle delivery, viral delivery, or a combination thereof. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments, the agronomic trait includes a biomass trait, a sucrose trait, a flowering trait, drought tolerance, and/or an aluminum tolerance trait. In some embodiments, the transgene nucleotide sequence includes a *Bacillus thuringiensis* toxin (BT) nucleotide sequence, a Cry nucleotide sequence, or a VIP nucleotide sequence. In some embodiments of this aspect, a combination of morphogenes is used. In some embodiments, one morphogene nucleotide sequence, two morphogene nucleotide sequences, three morphogene nucleotide sequences, four morphogene nucleotide sequences, five morphogene nucleotide sequences, six morphogene nucleotide sequences, seven morphogene nucleotide sequences, eight morphogene nucleotide sequences, nine morphogene nucleotide sequences, ten morphogene nucleotide sequences, eleven morphogene nucleotide sequences, twelve morphogene nucleotide sequences, thirteen morphogene nucleotide sequences, fourteen morphogene nucleotide sequences, fifteen morphogene nucleotide sequences, sixteen morphogene nucleotide sequences, seventeen morphogene nucleotide sequences, eighteen morphogene nucleotide sequences, nineteen morphogene nucleotide sequences, or twenty morphogene nucleotide sequences are introduced in step (b). In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one morphogene nucleotide sequence is introduced with a first vector and the at least one transgene nucleotide sequence is introduced with a second vector. In some embodiments of this aspect, the first vector includes a first promoter operably linked to the at least one morphogene nucleotide sequence, and the second vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene nucleotide sequence is introduced before the at least one transgene nucleotide sequence. In some embodiments of this aspect, the at least one morphogene nucleotide sequence is introduced at the same time as the at least one transgene nucleotide sequence. In some embodiments of this aspect, the at least one morphogene nucleotide sequence is introduced after the at least one transgene nucleotide sequence. In some embodiments of this aspect, the at least one morphogene nucleotide sequence and the at least one transgene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the introduction of the at least one morphogene nucleotide sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox. In some embodiments of this aspect, the method improves the number and quality of independent transgenic events per variety.

Still another aspect of the disclosure includes methods of increasing transformation efficiency of sugarcane cells, including (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 and at least one transgene nucleotide sequence into the sugarcane cells to produce transgenic sugarcane cells, wherein the transformation efficiency is increased as compared to a method of transforming sugarcane cells that does not use at least one morphogene protein sequence; and (c) cultivating the transgenic sugarcane cells for proliferation and regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. In some embodiments of this aspect, transformation efficiency is increased by at least 5% as compared to a method of transforming sugarcane cells that does not use at least one morphogene protein sequence. In some embodiments of this aspect, transformation is increased by 5%, 6%, 7%, 8%, 9%, 10%, 11%, 12%, 13%, 14%, 15%, 16%, 17%, 18%, 19%, 20%, 21%, 22%, 23%, or 24%. In some embodiments of this aspect, transformation efficiency is increased by 50% to 100% as compared to a method of transforming sugarcane cells that does not use at least one morphogene protein sequence. The increase in efficiency provided by the present methods represents a significant improvement over present methods, as some recalcitrant sugarcane varieties have less than 1% of transformation efficiency without the use of morphogenes. Some embodiments of this aspect further include screening the sugarcane cells between steps (b) and (c), screening the plantlets after step (d), or screening the plants after step (e) to identify the transgene. In some embodiments, screening may be done using PCR, ELISA, fluorescence detection, or other screening methods known in the art. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. The use of morphogenes may enhance the antibiotic concentration used in the selection step after transformation, because cells containing morphogenes have a higher proliferation and maturation post-transformation, which supports higher antibiotic concentrations. The use of higher antibiotic concentrations avoids escapes and increases the probability of finding high quality transformation events. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments of this aspect, a combination of morphogene proteins is used. In some embodiments, one morphogene protein sequence, two morphogene protein sequences, three morphogene protein sequences, four morphogene protein sequences, five morphogene protein sequences, six morphogene protein sequences, seven morphogene protein sequences, eight morphogene protein sequences, nine morphogene protein sequences, ten morphogene protein sequences, eleven morphogene protein sequences, twelve morphogene protein sequences, thirteen morphogene protein sequences, fourteen morphogene protein sequences, fifteen morphogene protein sequences, sixteen morphogene protein sequences, seventeen morphogene protein sequences, eighteen morphogene protein sequences, nineteen morphogene protein sequences, or twenty morphogene protein sequences are introduced in step (b). In some embodiments of this aspect, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene protein sequence is introduced through microprojectile bombardments or nanoparticle delivery. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the at least one morphogene protein sequence is introduced after the at least one transgene nucleotide sequence. In some embodiments of this aspect, the introduction of the at least one morphogene protein sequence is transient. Most means of introducing protein sequences known in the art result in degradation of the protein over time (i.e., transient expression). In some embodiments of this aspect, the genetically altered plant of step (e) does not include the at least one morphogene protein sequence.

The protocol of *Agrobacterium* transformation of a cell or tissue and subsequently regenerating it includes the following general stages: I: production or preparation of a cell or tissue (explant); II: transformation; III: co-cultivation (or co-culture) and rest; IV: selection; and V: regeneration and elongation. Stages II through V each require suitable culture media. Those skilled in the art are familiar with the composition of suitable culture media for the generation of transformable tissue (or transformable explant) (stage II: transformation), as well as the means of the co-cultivation stages (stage III: co-cultivation+rest), selection (stage IV: selection), and regeneration (stage V: regeneration+elongation). Preferably, the culture media used are based on compositions including ingredients such as MS salts (Murashige and Skoog, 1962), sucrose, and vitamins B5. Optionally, the following can also be added: amino acids selected from the group of proline and asparagine; casein hydrolysate; citric acid; mannitol; copper sulfate; glycine; gelling agent; auxins; antibiotics; acetosyringone; and selection agents. The use of hormones, e.g. auxins and/or cytokinins, are especially important in the steps of transformable tissue or transformable explant generation (stage I-II), co-cultivation (stage III) and selection (stage IV), as is the selection agents, e.g., ammonium glufosinate, in the selection medium (stage IV). Suitable explants for plant transformation includes, without limitation: callus, undifferentiated callus, immature and mature embryos, immature zygotic embryo, immature cotyledon, embryonic axis, suspension culture cells, protoplasts, leaf, leaf cells, leaf disks, root cells, phloem cells, pollen, seeds, suspension cultures, embryos, zygotic embryos, somatic embryos, embryogenic callus, meristem, somatic meristems, organogenic callus, protoplasts, leaf bases, leaves from mature plants, leaf tips, immature inflorescences, cotyledons, meristematic regions, cells from stems, cells from roots, cells from shoots, gametophytes, sporophytes, microspores, single cells and hypocotyl cells.

Sugarcane plants of the present disclosure include species and hybrids in the genus *Saccharum*, e.g., *Saccharum officinarum, Saccharum sinense, Saccharum barberi, Saccharum robustum, Saccharum spontaneum, Saccharum* spp., *Saccharum* spp. hybrid, etc. Methods of the present disclosure improve genotype independence of transformation methods.

In some aspects, the present disclosure relates to methods of increasing transformation efficiency wherein plant cells are used in place of sugarcane cells in any of the above methods. The plant cells may be derived from plants including corn (e.g., maize, *Zea mays*), barley (e.g., *Hordeum vulgare*), millet (e.g., finger millet, fonio millet, foxtail millet, pearl millet, barnyard millets, *Eleusine coracana, Panicum sumatrense, Panicum milaceum, Pennisetum glaucum, Digitaria* spp., *Echinocloa* spp.), oat (e.g., *Avena sativa*), rice (e.g., indica rice, japonica rice, aromatic rice, glutinous rice, *Oryza sativa, Oryza glaberrima*), rye (e.g., *Secale cereale, Secale cereanum*), sugarcane (e.g., *Saccharum* sp.), setaria (e.g., *Setaria italica, Setaria viridis*), *Brachypodium* sp., sorghum (e.g., *Sorghum bicolor*), teff (e.g., *Eragrostis tef*), triticale (e.g., X *Triticosecale* Wittmack, *Triticosecale schlanstedtense* Wittm., *Triticosecale neoblaringhemii* A. Camus, *Triticosecale neoblaringhemii* A. Camus), wheat (e.g., common wheat, spelt, durum, einkorn, emmer, kamut, *Triticum aestivum, Triticum spelta, Triticum durum, Triticum urartu, Triticum monococcum, Triticum turanicum, Triticum* spp.), switchgrass (e.g., *Panicum virgatum*), *Brassica* sp., or tobacco (e.g., *Nicotiana benthamiana, Nicotiana tabacum*), peanut (*Arachis hypogaea*), banana (*Musa* sp.), potato (*Solanum tuberosum*), strawberry (*Fragaria ananassa*), coffee (*Coffea arabica*), cotton (*Gossypium hirsutum*), tomato (*Solanum lycopersicum*) or any other polyploid and/or vegetatively propagated plant species.

Genome Editing and Methods of Increasing the Genome Editing Rate or Genome Editing Efficiency Some aspects of the disclosure relate to editing or modifying the sugarcane genome. Suitable plant material (explants) for genome editing includes sugarcane cells (e.g., in cell cultures) or sugarcane tissues (e.g., in plants; plant parts). Suitable explants for plant genome editing include, without limitation: callus, undifferentiated callus, immature and mature embryos, immature zygotic embryo, immature cotyledon, embryonic axis, suspension culture cells, protoplasts, leaf, leaf cells, leaf disks, root cells, phloem cells, pollen, seeds, suspension cultures, embryos, zygotic embryos, somatic embryos, embryogenic callus, meristem, somatic meristems, organogenic callus, protoplasts, leaf bases, leaves from mature plants, leaf tips, immature inflorescences, cotyledons, meristematic regions, cells from stems, cells from roots, cells from shoots, gametophytes, sporophytes, microspores, single cells, and hypocotyl cells. Genome editing targets include genes, introns, non-coding sequences (e.g., miRNAs), and regulatory elements (e.g., promoters). Multiple genome editing types may be used including knock-out editing, knock-in editing, homologous recombination, site-directed integration, base editing, or prime editing. Similarly, multiple genome editing components may be used. In a preferred embodiment, the genome engineering component includes a CRISPR system, preferably a CRISPR/Cas9 or a CRISPR/Cpf1 system, and a targeting sequence. Genome engineering components may be delivered in multiple formats including via plasmids or using a ribonucleoprotein (RNP) complex.

Specific genome editing components may be preferred for specific genome editing types. In a preferred embodiment, the genome editing reagent for knock-out (KO) editing is a plasmid containing a Cas gene (Cas9 or Cpf1) and its crRNA. For knock-in editing mediated by homologous recombination (HR), a homologous template in the format of a plasmid may be delivered in addition to Cas and crRNA. In a further embodiment, a homologous template in the format of dsDNA or ssDNA may be delivered in addition to Cas and crRNA. For homologous recombination, the HR template may be delivered on the same plasmid (co-delivery) or a separate plasmid as that of the genome editing reagent.

Similarly, specific delivery methods may be preferred for specific genome editing approaches. In some embodiments, genome editing reagents and morphogenes may be delivered using the same plasmid (co-delivery). In some embodiments, morphogenes may be delivered on a separate plasmid from the plasmid on which the genome editing reagent is delivered. In embodiments where morphogenes and genome editing reagents are delivered in plasmid(s), either *Agrobacterium* transformation or particle bombardment may be used for delivery. In some embodiments that include RNP being used to deliver genome engineering components and/or an HR template being delivered in a separate plasmid, particle bombardment or nanoparticles may be used. In some embodiments, for crop species where protoplasts are used, RNP may be used for protoplast transfection. In some embodiments, templates may be delivered in the form of oligonucleotides (i.e., without the use of plasmids).

Genome editing rate and/or genome editing efficiency may be determined by the number of alleles containing the mutation of interest as determined by methods including restriction fragment length polymorphism (RFLP), next generation sequencing (NGS), PCR, Sanger sequencing, etc. as a percentage of total alleles analyzed after exposure to the genome editing reagent. For loss-of-function mutations, cell phenotyping methodologies such as Western blot or fluorescence analysis can also be used to determine if the synthesis of a protein or the function of a protein has been disrupted due to the editing of a target gene. Gene editing efficiency is generally determined by methods such as NGS, ddPCR, and PCR. Morphogenes can impact gene editing efficiency in different ways, by increasing transformation frequency, or extending cell proliferation phase, thereby increasing gene editing rates. In the case of HR, the native machinery is more active in dividing cells, and it is hypothesized that morphogenes increase HR efficiency because of their effect on cell divisions. Otherwise, the effect of morphogenes can be through breaking recalcitrance during the cell cycle (TC) and transcription (TXN).

An additional aspect of the disclosure includes methods of increasing the genome editing rate and/or genome editing efficiency of a genome of a sugarcane cell, including (a) providing a sugarcane cell; (b) introducing a genome editing component, wherein the genome editing component targets one or more gene sequences in the sugarcane genome, and introducing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20 into the sugarcane cell to produce a genetically modified sugarcane cell including one or more edited gene sequences, wherein the genome editing rate and/or genome editing efficiency is increased as compared to a method of genome editing that does not use at least one morphogene nucleotide sequence; and (c) cultivating the genetically modified sugarcane cells for proliferation and/or regeneration. Some embodiments of this aspect further include (d) cultivating the genetically modified sugarcane cell into a genetically modified plantlet; and (e) growing the genetically modified plantlet into a genetically modified plant including one or more edited gene sequences. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. Some embodiments of this aspect further include screening the sugarcane cells between steps (b) and (c), screening the plantlets after step (d), or screening the plants after step (e) to identify the edited genes. Some embodiments of this aspect further include selection of genetically modified sugarcane cells between steps (b) and (c), or selection of genetically modified plantlets after step (d), optionally by using nucleotide-based screening methods or by using selectable markers. In some embodiments of this aspect, step (b) is achieved through *Agrobacterium* transformation, microprojectile bombardments, nanoparticle delivery, viral delivery, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, the gene sequences are agronomic trait gene sequences. Agronomic traits include biomass, sucrose content, flowering time, drought tolerance, and aluminum tolerance. In some embodiments of this aspect, a combination of morphogenes is used. In some embodiments, one morphogene nucleotide sequence, two morphogene nucleotide sequences, or three morphogene nucleotide sequences are introduced in step (b). In some embodiments of this aspect, the genome editing component is introduced with a first vector and the at least one morphogene nucleotide sequence is introduced with a second vector. In some embodiments of this aspect, the first vector includes a first promoter operably linked to the genome editing component, and wherein the second vector includes a second promoter operably linked to the at least one morphogene nucleotide sequence. In some embodiments of this aspect, the first and second promoters are selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the genome editing component is introduced before the at least one morphogene nucleotide sequence. In some embodiments of this aspect, the genome editing component is introduced at the same time as the at least one morphogene nucleotide sequence. In some embodiments of this aspect, the genome editing component is introduced after the at least one morphogene nucleotide sequence. In some embodiments of this aspect, the genome editing component and the at least one morphogene nucleotide sequence are co-introduced with a vector. In some embodiments of this aspect, the vector includes a first promoter operably linked to the at least one morphogene nucleotide sequence, and the vector includes a second promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the introduction of the at least one morphogene nucleotide sequence is transient. In some embodiments of this aspect, the genetically altered plant of step (e) does not include the at least one morphogene nucleotide sequence. Some embodiments of this aspect include the introduction of the at least one morphogene being stable, and the at least one morphogene being excised from the sugarcane cell after delivery in step (b). Excision methods known in the art are used for excision, e.g., Cre-Lox.

An additional aspect of the disclosure includes methods of increasing the genome editing rate and/or genome editing efficiency, including (a) providing a sugarcane cell or tissue; (b) introducing a genome editing component, wherein the genome editing component targets one or more gene sequences in the sugarcane genome, and introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 into the sugarcane cell to produce a genetically modified sugarcane cell including one or more edited gene sequences; and (c) cultivating the genetically modified sugarcane cells for proliferation and/or regeneration. Some embodiments of this aspect further include (d) cultivating the genetically modified sugarcane cell into a genetically altered plantlet; and (e) growing the genetically altered plantlet into a genetically altered plant including the one or more edited gene sequences. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect further include screening the sugarcane cells between steps (b) and (c), screening the sugarcane cells during step (c), or screening the sugarcane cells after step (c), and optionally further include selecting the genetically modified sugarcane cells between steps (b) and (c), or selecting the genetically modified sugarcane cells after step (c), optionally by using nucleotide-based screening methods or by using selectable markers. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the genome editing component is a CRISPR/Cas enzyme encoding sequence and a targeting sequence. In some embodiments of this aspect, the genome editing includes knock out editing, homologous recombination, site-directed integration, base editing, or prime editing. In some embodiments of this aspect, a combination of morphogenes is used. In some embodiments, one morphogene protein sequence, two morphogene protein sequences, or three morphogene protein sequences are introduced in step (b). In some embodiments of this aspect, the at least one morphogene protein sequence is introduced through microprojectile bombardments or nanoparticle delivery. In some embodiments of this aspect, the genome editing component is introduced with a vector. In some embodiments of this aspect, the vector includes a promoter operably linked to the genome editing component. In some embodiments of this aspect, the promoter is selected from the group of a constitutive promoter, an inducible promoter, or a tissue-specific or cell-type-specific promoter. In some embodiments of this aspect, the genome editing component is introduced with a ribonucleoprotein (RNP). In some embodiments of this aspect, the at least one morphogene protein sequence is introduced before the genome editing component. In some embodiments of this aspect, the genome editing component is introduced at the same time as the at least one morphogene protein sequence. In some embodiments of this aspect, the introduction of the at least one morphogene protein sequence is transient. In some embodiments of this aspect, the genetically altered plant of step (e) does not include the at least one morphogene protein sequence.

The protocol of *Agrobacterium* transformation of a cell or tissue and subsequently regenerating it includes the following general stages: I: production or preparation of a cell or tissue (explant); II: transformation; III: co-cultivation (or co-culture) and rest; IV: selection; and V: regeneration and elongation. Stages II through V each require suitable culture media. Those skilled in the art are familiar with the composition of suitable culture media for the generation of transformable tissue (or transformable explant) (stage II: transformation), as well as the means of the co-cultivation stages (stage III: co-cultivation+rest), selection (stage IV: selection), and regeneration (stage V: regeneration+elongation). Preferably, the culture media used are based on compositions including ingredients such as MS salts (Murashige and Skoog, 1962), sucrose, and vitamins B5. Optionally, the following can also be added: amino acids selected from the group of proline and asparagine; casein hydrolysate; citric acid; mannitol; copper sulfate; glycine; gelling agent; auxins; antibiotics; acetosyringone; and selection agents. The use of hormones, e.g. auxins and/or cytokinins, are especially important in the steps of transformable tissue or transformable explant generation (stage I-II), co-cultivation (stage III) and selection (stage IV), as is the selection agent, e.g., ammonium glufosinate, in the selection medium (stage IV). Suitable explants for plant transformation includes, without limitation: callus, undifferentiated callus, immature and mature embryos, immature zygotic embryo, immature cotyledon, embryonic axis, suspension culture cells, protoplasts, leaf, leaf cells, leaf disks, root cells, phloem cells, pollen, seeds, suspension cultures, embryos, zygotic embryos, somatic embryos, embryogenic callus, meristem, somatic meristems, organogenic callus, protoplasts, leaf bases, leaves from mature plants, leaf tips, immature inflorescences, cotyledons, meristematic regions, cells from stems, cells from roots, cells from shoots, gametophytes, sporophytes, microspores, single cells and hypocotyl cells.

Sugarcane plants of the present disclosure include species and hybrids in the genus *Saccharum*, e.g., *Saccharum officinarum, Saccharum sinense, Saccharum barberi, Saccharum robustum, Saccharum spontaneum, Saccharum* spp., *Saccharum* spp. hybrid, etc. Methods of the present disclosure improve genotype independence of transformation methods.

In some aspects, the present disclosure relates to methods of increasing the genome editing rate or genome editing efficiency wherein plant cells are used in place of sugarcane cells in any of the above methods. The plant cells may be derived from plants including corn (e.g., maize, *Zea mays*), barley (e.g., *Hordeum vulgare*), millet (e.g., finger millet, fonio millet, foxtail millet, pearl millet, barnyard millets, *Eleusine coracana, Panicum sumatrense, Panicum milaceum, Pennisetum glaucum, Digitaria* spp., *Echinocloa* spp.), oat (e.g., *Avena sativa*), rice (e.g., indica rice, japonica rice, aromatic rice, glutinous rice, *Oryza sativa, Oryza glaberrima*), rye (e.g., *Secale cereale, Secale cereanum*), sugarcane (e.g., *Saccharum* sp.), setaria (e.g., *Setaria italica, Setaria viridis*), *Brachypodium* sp., sorghum (e.g., *Sorghum bicolor*), teff (e.g., *Eragrostis tef*), triticale (e.g., X *Triticosecale* Wittmack, *Triticosecale schlanstedtense* Wittm., *Triticosecale neoblaringhemii* A. Camus, *Triticosecale neoblaringhemii* A. Camus), wheat (e.g., common wheat, spelt, durum, einkorn, emmer, kamut, *Triticum aestivum, Triticum spelta, Triticum durum, Triticum urartu, Triticum monococcum, Triticum turanicum, Triticum* spp.), switchgrass (e.g., *Panicum virgatum*), *Brassica* sp., tobacco (e.g., *Nicotiana benthamiana, Nicotiana tabacum*), peanut (*Arachis hypogaea*), banana (*Musa* sp.), potato (*Solanum tuberosum*), strawberry (*Fragaria ananassa*), coffee (*Coffea arabica*), cotton (*Gossypium hirsutum*), tomato (*Solanum lycopersicum*) or any other polyploid and/or vegetatively propagated plant species.

Morphogenes

Morphogenes are genes that have been functionally demonstrated to improve somatic embryogenesis and/or regeneration. The methods of this disclosure utilize homologs and orthologs of these morphogene families from various grass species to improve the process of plant cell transformation. The plant cells may be derived from plants including corn (maize), barley, millet, oat, rice, rye, sugarcane (e.g., *Saccharum* sp.), *Setaria* sp., *Brachypodium* sp., *Sorghum* sp., teff, switchgrass, triticale, wheat, *Brassica* sp., tobacco, peanut (*Arachis hypogaea*), banana (*Musa* sp.), potato (*Solanum tuberosum*), strawberry (*Fragaria ananassa*), coffee (*Coffea arabica*), cotton (*Gossypium hirsutum*), tomato (*Solanum lycopersicum*) or any other polyploid and/or vegetatively propagated plant species. The plant cells may also be derived from other monocot and dicot plant species. The methods of this disclosure may be particularly suited for transformation and genetic modification of recalcitrant species.

Morphogenes can also be used to increase transformation and regeneration efficiency of genome editing using a transgenic approach. Any combination of morphogenes may be used in the methods of the present disclosure. Improved efficiency is important for proof of concept studies, such as validating functions of candidate trait genes. Proof of concept studies may use model systems such as maize embryos, which allow highly quantitative assessment of reporter expression, protoplasts or plant tissues such as leaf disks, which allow quick preliminary evaluation.

Increased transformation and regeneration efficiency is especially important for the types of genome editing that have low editing efficiency, such as knock in editing mediated by homologous recombination. Specifically, morphogenes can be co-delivered with genome editing reagents and a selectable marker to sugarcane leaf disks or sugarcane callus to increase the transformation and regeneration efficiency of genome editing, and then selection can be used to identify the edited plants. In a preferred embodiment, the genome editing reagent for knock-out (KO) editing is a plasmid containing a Cas gene (Cas9 or Cpf1) and its crRNA. In another embodiment, the genome editing reagents are delivered using a ribonucleoprotein (RNP) complex. For knock-in editing mediated by homologous recombination (HR), a homologous template in the format of a plasmid is delivered in addition to Cas and crRNA. In a further embodiment, a homologous template in the format of dsDNA or ssDNA is delivered in addition to Cas and crRNA. If genome editing reagents are delivered in a plasmid format, morphogenes may be included in the same plasmid. In an additional embodiment, morphogenes are delivered on a separate plasmid from that of the genome editing reagent. The HR template may be delivered in the same plasmid or a separate plasmid as that of the genome editing reagent too. Morphogenes with genome editing reagents in plasmid(s) may be delivered by *Agrobacterium* transformation or particle bombardment. When RNP is used and/or when an HR template is used in a separate plasmid, particle bombardment may be used for delivery. Options for genome editing approaches are shown in FIGS. 2A-2B.

Morphogenes may also be used to increase transformation and regeneration efficiency of genome-edited events in a transgene-free way. This procedure is similar to what is described above, but without a selectable marker for the selection step. Instead, genome-edited events are detected directly, e.g., by using a PCR-based approach. This transgene-free approach is critical for event production with commercial traits and for the ease of deregulation. Further details of this approach are described in Example 6. Options for transgene-free genome editing approaches are shown in FIG. 3.

The aspects of transformation improved by morphogenes include early cell proliferation, faster cell proliferation, faster maturation post-transformation, and faster regeneration. Overall, morphogenes shorten the transformation process and result in higher transformation rates. In addition, morphogenes allow alternative plant materials to be used, for example direct transformation of leaf tissue instead of, e.g., callus. While beneficial during the transformation process, stable introgression of a morphogene may negatively impact plant development, so morphogenes are preferably excised after introduction or delivered transiently.

The following genes from *Arabidopsis thaliana* have been characterized as morphogenes. SHOOT-MERISTEM-LESS (STM; *A. thaliana* gene At1g62360) is a KNOX1-KNOX2-ELK-homeobox transcription factor that acts in the same pathway as WUS to maintain indeterminate cell fate at meristems. When overexpressed in *Z. mays*, STM has been demonstrated to induce a switch from determinate to indeterminate cell fates (Sinha et al., 1993, Genes Fev. 7:787-795). WUSCHEL (WUS; *A. thaliana* gene At2g17950) is a homeobox domain transcription factor that has been shown to promote a transition from vegetative cell to embryonic cell in *A. thaliana*, and that is required for the establishment of the shoot meristem during embryogenesis (Zuo et al., et al., 2002, Plant Journal 30(3):349-359; Su et al., 2009, Plant Journal 59(3):448-460). Overexpression of WUS promotes/maintains embryonic potential during somatic embryogenesis. GROWTH-REGULATING FACTOR 5 (GRF5; *A. thaliana* gene At3g13960) has a QLQ-WRC domain, and has been shown to regulate cell proliferation in leaf primordia cells of *A. thaliana* (Horiguchi et al., 2005, Plant and Cell Phys 61(6):1181-1190). When GRF5 is overexpressed, organ size is increased. WOUND INDUCED DEDIFFERENTIATION1 (WIND1; also known as RAP2.4; *A. thaliana* gene At1g78080) is an AP2 domain transcription factor that has been shown to promote both cell dedifferentiation and cell proliferation at plant wound sites in *A. thaliana*. When overexpressed, WIND1 induces somatic embryogenesis in *A. thaliana* (Iwase et al., 2011, Plant Signaling and Behavior 6(12):1943-1945). ENHANCER OF SHOOT REGENERATION1 (ESR1; *A. thaliana* gene At1g12980) is an AP2 domain protein that is activated during shoot regeneration in *A. thaliana*, and when overexpressed, induces callus formation at wound sites (Iwase et al., 2017, Plant Cell 29:54-69). WIND1 binds to and activates the ESR1 promoter.

BABY BOOM (BBM; *A. thaliana* gene At5g17430) is an AP2/ERF transcription factor that has been demonstrated to activate downstream genes (LEC1, ABI3, FUS3, and LEC2) to induce somatic embryogenesis. BBM overexpression has been shown to induce somatic embryogenesis and hormone-free regeneration in *A. thaliana* and *Brassica napus* (Boutilier et al., 2002, Plant Cell 14(8):1737-1749; Horstman et al., 2017, Plant Physiology 175:848-857), PLETHORA2 (PLT2; *A. thaliana* gene At1g51190) is an AP2 domain transcription factor that has been implicated in embryo development, and that induces somatic embryogenesis in a dose-and explant-dependent manner (Ouakfaoui et al., 2010, Plant Molecular Biology 74(4-5):313-326; Szczygiel-Sommer and Gaj, 2019, Int J Mol Sci 20(20):5221).), EMBRYOMAKER/AINTEGUMENTA-like 5/PLETHORA5 (EMK/AIL5/PLT5; *A. thaliana* gene At5g57390) is closely related to PLT2, and is also an AP2 domain protein that induces somatic embryogenesis in a dose- and explant-dependent manner (Tsuwamoto et al., 2010 Plant Molecular Biology 73(4-5):481-492). LEAFY COTYLEDON (LEC2; *A. thaliana* gene At1g28300) is a B3 domain transcription factor that induces embryo development in *A. thaliana*. LEC1 and LEC2 orthologous genes were shown to be key regulators of somatic embryogenesis in *Manihot esculenta* (Brand et al., 2019, Front Plant Sci, doi.org/10.3389/fpls.2019.00673) and a related B3 transcription factor gene was shown to promote somatic embryogenesis in citrus (Liu, 2018, Plant Sci 277:121-131). AGAMOUS-LIKE 15 (AGL15; *A. thaliana* gene At5g13790) is a MADS-box transcription factor that has been shown to maintain the embryogenic potential of plant cells. When overexpressed, AGL15 induces somatic embryogenesis in *A. thaliana* and *Glycine max* (Harding et al., 2003, Plant Physiology 133:803-816; Thakare et al., 2008, Plant Physiology 146:1663-1672). RWP-RK DOMAIN-CONTAINING 4 (RKD4; *A. thaliana* gene At5g53040) is a RWP-RK transcription factor involved in early embryogenesis that induces somatic embryogenesis in *A. thaliana* (Waki et al., 2014, 21(15):1277-1281). SOMATIC EMBRYOGENESIS RECEPTOR KINASE 1 (SERK1; *A. thaliana* gene At1g71830) is a transmembrane protein with LRR domains that enhances embryogenic competence in culture. Specifically, overexpression of SERK1 has been demonstrated to increase the efficiency of somatic embryogenesis in *A. thaliana* cell culture. (Hecht et al., 2001, Plant Physiol., 127: 803-816).

"Altruistic" Delivery Methods

Certain aspects of the present disclosure relate to methods of morphogene delivery described as "altruistic" delivery methods. In some embodiments, altruistic delivery includes separate production of morphogene proteins and exogenous application of the morphogene proteins or any other compound derived as the result of the overexpression morphogene to the transformation process (e.g., addition of morphogene proteins to tissue culture or transformation media). In some embodiments, altruistic delivery includes co-culture of the target cells/tissues (cells/tissues for transformation or genome editing) with transgenic "feeder" cells or tissue culture, wherein the feeder culture produces morphogene proteins that are released into the transformation media. Cells undergoing transformation in which altruistic delivery methods are used do not need to simultaneously express both the morphogenes and the transgene of interest. Similarly, there is no need to remove morphogene expression after the transformation process, e.g., via transient expression or subsequent excision of morphogenes. These methods allow full utilization of the benefits of morphogene use (e.g., early cell proliferation, faster cell proliferation, faster maturation post-transformation, faster regeneration, shorter transformation process, higher transformation rates), while avoiding the potential detriments of morphogenes (e.g., possible negative impact on plant development).

In some embodiments, altruistic delivery methods use secreted proteins produced from downstream signaling pathways initiated by morphogenes. In some embodiments, altruistic delivery methods use metabolites produced as a result of the morphogenes. In some embodiments, altruistic delivery methods used supernatant from transgenic "feeder" cells to "feed" the tissue culture with the target cells/tissue (cells/tissues for transformation or genome editing). Feeder cells can be any plant cell, not necessarilly from the same species of the target cell or tissue.

An aspect of the disclosure includes methods of increasing transformation efficiency of sugarcane cells, including (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40, wherein introducing the at least one morphogene protein sequence is through exogenous application, and introducing at least one transgene nucleotide sequence into the sugarcane cells to produce transgenic sugarcane cells, wherein the transformation efficiency is increased as compared to a method of transforming sugarcane cells that does not use at least one exogenously applied morphogene protein sequence; and step (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene sequence is selected from the group of SEQ ID NO: 1, SEQ ID NO: 10, SEQ ID NO: 11, SEQ ID NO: 12, SEQ ID NO: 14, or SEQ ID NO: 20. Some embodiments of this aspect include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. In some embodiments of this aspect, transformation efficiency is increased by at least 5% as compared to a method of transforming sugarcane cells that does not use at least one exogenously applied morphogene protein sequence. In some embodiments of this aspect, transformation is increased by 5%, 6%, 7%, 8%, 9%, 10%, 11%, 12%, 13%, 14%, 15%, 16%, 17%, 18%, 19%, 20%, 21%, 22%, 23%, or 24%. In some embodiments of this aspect, transformation efficiency is increased by 50% to 100% as compared to a method of transforming sugarcane cells that does not use at least one exogenously applied morphogene protein sequence. The increase in efficiency provided by the present methods represents a significant improvement over present methods, as some recalcitrant sugarcane varieties have less than 1% of transformation efficiency without the use of morphogenes. Some embodiments of this aspect further include screening the sugarcane cells between steps (b) and (c), screening the plantlets after step (d), or screening the plants after step (e) to identify the transgene. In some embodiments, screening may be done using PCR, ELISA, fluorescence detection, sequencing, or other screening methods known in the art. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. In some embodiments of this aspect, step (b) is achieved through *Agrobacterium* transformation, microprojectile bombardments, nanoparticle delivery, viral delivery, any other protein delivery technology, or a combination thereof. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments of this aspect, a combination of morphogene proteins is used. In some embodiments, one morphogene protein sequence, two morphogene protein sequences, three morphogene protein sequences, four morphogene protein sequences, five morphogene protein sequences, six morphogene protein sequences, seven morphogene protein sequences, eight morphogene protein sequences, nine morphogene protein sequences, ten morphogene protein sequences, eleven morphogene protein sequences, twelve morphogene protein sequences, thirteen morphogene protein sequences, fourteen morphogene protein sequences, fifteen morphogene protein sequences, sixteen morphogene protein sequences, seventeen morphogene protein sequences, eighteen morphogene protein sequences, nineteen morphogene protein sequences, or twenty morphogene protein sequences are introduced in step (b). In some embodiments of this aspect, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the at least one morphogene protein sequence is introduced through addition to the cell cultivation media. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the at least one morphogene protein sequence is introduced after the at least one transgene nucleotide sequence.

An aspect of the disclosure includes methods of increasing transformation efficiency of sugarcane cells, including (a) providing sugarcane cells or tissue; (b) introducing at least one morphogene protein sequence including SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40, wherein introducing the at least one morphogene protein sequence is through co-culture with transgenic feeder cells, and introducing at least one transgene nucleotide sequence into the sugarcane cells to produce transgenic sugarcane cells, wherein the transformation efficiency is increased as compared to a method of transforming sugarcane cells that does not use at least one morphogene protein sequence produced by transgenic feeder cells; and (c) cultivating the transgenic sugarcane cells for proliferation and/or regeneration. Some embodiments of this aspect further include (d) cultivating the transgenic sugarcane cells into genetically altered plantlets; and (e) growing the genetically altered plantlets into genetically altered plants including the at least one transgene nucleotide sequence. In some embodiments of this aspect, the at least one morphogene protein sequence is selected from the group of SEQ ID NO: 21, SEQ ID NO: 30, SEQ ID NO: 31, SEQ ID NO: 32, SEQ ID NO: 34, or SEQ ID NO: 40. Some embodiments of this aspect include screening the sugarcane cells between steps (b) and (c), screening the sugarcane cells during step (c), or screening the sugarcane cells after step (c), and optionally further include selecting the transgenic sugarcane cells between steps (b) and (c), or selecting the transgenic sugarcane cells after step (c), optionally by using selectable markers. In some embodiments of this aspect, transformation efficiency is increased by at least 5% as compared to a method of transforming sugarcane cells that does not use at least one morphogene protein sequence produced by transgenic feeder cells. In some embodiments of this aspect, transformation is increased by 5%, 6%, 7%, 8%, 9%, 10%, 11%, 12%, 13%, 14%, 15%, 16%, 17%, 18%, 19%, 20%, 21%, 22%, 23%, or 24%. In some embodiments of this aspect, transformation efficiency is increased by 50% to 100% as compared to a method of transforming sugarcane cells that does not use at least one morphogene protein sequence produced by transgenic feeder cells. The increase in efficiency provided by the present methods represents a significant improvement over present methods, as some recalcitrant sugarcane varieties have less than 1% of transformation efficiency without the use of morphogenes. Some embodiments of this aspect further include screening the sugarcane cells between steps (b) and (c), screening the plantlets after step (d), or screening the plants after step (e) to identify the transgene. In some embodiments, screening may be done using PCR, ELISA, fluorescence detection, sequencing, or other screening methods known in the art. Some embodiments of this aspect further include selecting the transgenic sugarcane cells between steps (b) and (c), or selecting the genetically altered plantlets after step (d), optionally by using selectable markers. These selectable markers may be nptII, BAR, EPSPS, and/or any other suitable selectable marker. The use of morphogenes may enhance the antibiotic concentration used in the selection step after transformation, because cells containing morphogenes have a higher proliferation and maturation post-transformation, which supports higher antibiotic concentrations. The use of higher antibiotic concentrations avoids escapes and increases the probability of finding high quality transformation events. In some embodiments of this aspect, step (b) is achieved through *Agrobacterium* transformation, microprojectile bombardments, nanoparticle delivery, viral delivery, or a combination thereof. In some embodiments of this aspect, the at least one transgene nucleotide sequence encodes a protein selected from the group consisting of a fluorescent protein (e.g., GFP, CFP, dsRED, etc.), a herbicide resistance protein (e.g., CP4-EPSPS, BAR, ALS, etc.), an agronomic trait protein, and a disease/pest resistance protein (e.g., BT, Cry, VIP, etc.). In some embodiments of this aspect, a combination of morphogene proteins is used. In some embodiments, one morphogene protein sequence, two morphogene protein sequences, three morphogene protein sequences, four morphogene protein sequences, five morphogene protein sequences, six morphogene protein sequences, seven morphogene protein sequences, eight morphogene protein sequences, nine morphogene protein sequences, ten morphogene protein sequences, eleven morphogene protein sequences, twelve morphogene protein sequences, thirteen morphogene protein sequences, fourteen morphogene protein sequences, fifteen morphogene protein sequences, sixteen morphogene protein sequences, seventeen morphogene protein sequences, eighteen morphogene protein sequences, nineteen morphogene protein sequences, or twenty morphogene protein sequences are introduced in step (b). In some embodiments of this aspect, one morphogene protein sequence, two morphogene protein sequences, or three morphogene protein sequences are introduced in step (b). In some embodiments of this aspect, one transgene nucleotide sequence, two transgene nucleotide sequences, three transgene nucleotide sequences, four transgene nucleotide sequences, five transgene nucleotide sequences, six transgene nucleotide sequences, seven transgene nucleotide sequences, eight transgene nucleotide sequences, nine transgene nucleotide sequences, or ten transgene nucleotide sequences are introduced in step (b). In some embodiments of this aspect, the at least one transgene nucleotide sequence is introduced with a vector. In some embodiments of this aspect, the vector includes a promoter operably linked to the at least one transgene nucleotide sequence. In some embodiments of this aspect, the first and second promoters are selected from the group of a constitutive promoter, an inducible promoter, or a tissue-specific or cell-type-specific promoter. In some embodiments of this aspect, the sugarcane cells to be transformed are co-cultured with the transgenic feeder cells. In some embodiments of this aspect, the at least one morphogene protein sequence is introduced through transgenic feeder cells expressing at least one morphogene nucleotide sequence including SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20. In some embodiments of this aspect, the transgenic feeder cells release the morphogene protein sequences of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and/or SEQ ID NO: 40 into the transformation media. In some embodiments of this aspect, the at least one morphogene protein sequence is introduced before the at least one transgene nucleotide sequence. In some embodiments of this aspect, the at least one morphogene protein sequence is introduced at the same time as the at least one transgene nucleotide sequence. In some embodiments of this aspect, the at least one morphogene protein sequence is introduced after the at least one transgene nucleotide sequence. In some embodiments of this aspect, the method generates between ten and twenty independent transformation events per variety.

Molecular Biological and Biotechnological Methods

One embodiment of the present disclosure provides a genetically altered sugarcane plant including one or more transgenes (i.e., one or more heterologous genes) or one or more edited gene sequences in the sugarcane genome (i.e., one or more edited endogenous genes). Certain aspects of the present disclosure relate to methods for producing these genetically altered sugarcane plants. In some embodiments, these methods use morphogenes to increase transformation and regeneration efficiency.

Any methodology known in the art to delete, insert or otherwise modify the cellular DNA (e.g., genomic DNA and organelle DNA) can be used in practicing the inventions disclosed herein. For example, a disarmed Ti plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, of the T-DNA of the Ti-plasmid. Other types of vectors can also be used to transform the plant cell.

Recombinant DNA technology has enabled the isolation of genes and their stable insertion into a host genome. This technique, also called genetic transformation, can be defined as the controlled introduction of nucleic acids ("DNA" or DNA) into a recipient genome, excluding introduction by fertilization. It is a controlled process where a defined DNA fragment is introduced into the host (or recipient) genome and must be integrated into it. The stable insertion of these molecules into a host genome gives rise to an individual with a genome that is equal or substantially equal to the recipient (host) of the recombinant molecule, but with a new and particular feature. "Substantially equal" means a genome with more than 80%, preferably 85%, 90%, 95%, 98%, 99% or 100% of identity in relation to the recipient.

There are several plant genetic transformation techniques grouped into two main categories: indirect and direct gene transfer. Indirect transfer is when exogenous DNA is inserted into the genome by the action of a biological vector, while direct transfer is based on physical-biochemical processes. Different tissues and/or cells could be used according to the genetic transformation technique and according to the species or genotypes to be transformed. Generally, these tissues or cells include, without limitation, embryogenic callus, callus, protoplasts, embryos, somatic embryos, meristematic tissues, an any other part, tissue or cell of plant with regenerative capacity.

Indirect transformation is based on the bacterium-mediated system of the genus *Agrobacterium* and has been the most widely used method for obtaining transgenic plants. Advantages to this method include the ability to transfer relatively long DNA segments without rearrangement while maintaining low copy number integration of the transgenes, thus ensuring greater genotypic stability for the generated events. Several *Agrobacterium* species and strains, plasmids and protocols have been developed and adapted for genetic transformation of several plant species. The advantages of these methods include higher probabilities to single copy events, stable integration, and genetic heritage of the introduced genetic traits, as well as, consistent genic expression through generations and lower rates of gene silencing.

*Agrobacterium tumefaciens* and *A. rhizogenes* are gram negative soil phytopathogenic bacteria belonging to the Rhizobiaceae family that cause diseases in dicotyledons, known as crown and hairy root galls, respectively. In this plant-pathogen interaction there is a process of natural gene transfer between the *agrobacterium* and the plant cell wherein fragments of bacterial DNA are transferred into the plant cell (T-DNA), integrating with the nuclear genome. In its natural form, the bacterium transfers T-DNA ("transferred DNA"), which is part of the bacterial plasmid called Ti ("tumor-inducing") and integrates into the genome of infected plant cells. The T-DNA fragment that is transferred to the plant cell includes genes involved in the constitutive biosynthesis of phytohormones (auxins and cytokinins), which alter the normal developmental program of infected tissue and cause tumor formation. In addition, it also contains oncogenes for the synthesis of sugars and amino acids called opines, which serve as carbon and nitrogen sources for bacteria (Oger et al. 1997). Repeated ends of 25 base pairs (bp) at the right and left edges delimit the T-DNA and are essential for its transfer. Phenolic compounds released by injured plant tissues activate specific regions (vir regions), initiating the process of transfer of T-DNA to the plant cell. *Agrobacterium* also has chromosomal (chv) genes that promote binding between bacterial and host cells, allowing the formation of the pore passage of the T-DNA-containing complex (Sheng & Citovsky. 1996).

Since the segment to be transferred is defined by its edges, any sequence flanked by the edges can be transferred to a plant by means of agrobacteria, making it possible to manipulate these sequences in order to transfer coding sequences of interest. The replacement or deletion of the coding regions of wild-type T-DNA (oncogenes) allows for the generation of non-oncogenic (disarmed) *Agrobacterium* strains, which can carry the sequences of interest. The modified T-DNA is able to transfer the sequences of interest to plants because the virulence genes (vir region) remain intact.

Additionally, the *Agrobacterium* indirect transformation system allows for the transfer of artificial plasmid constructs to plants as long as the constructs contain such T-DNA edges, which enables the flexibility to use molecular tools and materials developed for other bacterial strains. These artificial plasmid constructs have promoters from different origins, as for example, plant promoters, viral promoters, bacterial and or chimeric promoters, besides genes that confer antibiotic resistance, herbicide resistance or tolerance or enzymatic activity (phosphomannose isomerase (PMI)/mannose (Man)) so these markers can be used for the selection of transformed cells or plants. These constructions also can contain auxiliary genes which interfere with relevant morphogenesis signaling pathways, enhancing the efficiency of the genetic transformation process and regeneration of vegetal tissues (See "Morphogenes" section above).

In one aspect of the present disclosure, foreign or exogenous DNA to be introduced into the plant is cloned into a binary plasmid between the left and right edge consensus sequences (T-DNA). The binary plasmid is transferred to an *Agrobacterium* cell, which is subsequently used to infect plant tissue. The T-DNA region of the vector including the exogenous DNA is inserted into the plant genome. The marker gene expression cassette and the characteristic gene expression cassette may be present in the same region of T-DNA, in different regions of T-DNA on the same plasmid, or in different regions of T-DNA on different plasmids. In one embodiment of the present invention, the cassettes are present in the same region as the T-DNA. One of skill in the art is familiar with the methods of indirect transformation by *Agrobacterium*.

Alternatively, direct DNA transfer can be used to directly introduce DNA into a plant cell. One method of direct DNA transfer is to bombard plant cells with a vector including DNA for insertion using a particle gun (particle-mediated biolistic transformation). Other methods for transformation of plant cells include protoplast transformation (optionally in the presence of polyethylene glycols (PEGs)); ultrasound treatment of plant tissues, cells, or protoplasts in a medium including the polynucleotide or the vector; microinjection of the polynucleotide or vector into plant material; microinjection, vacuum infiltration, sonication, use of silicon carbide, chemical transformation with PEG, electroporation of plant cells and the like. Disadvantages of direct transformation include challenges related to regeneration of plant tissue and the low transgene expression.

In addition, genetic transformation can be performed by site direct insertion through homologous recombination mediated by nucleases (genome editing). In recent years, genome editing technology based on use of engineered or chimeric nucleases has enabling the generation of genetically modified organisms in a more precise and specific way. The introduction of exogenous or foreign genes occur by homologous recombination through introduction of a Homologous recombination template (HR) having the exogenous DNA linked to a DNA fragment homologous to the genome of the receptor organism. The tools available include the chimeric enzymatic system CRISPR(clustered, regularly interspaced, short palindromic repeats)—Cas, the Zinc finger nucleases (ZFN) and TAL effector nucleases (TALENs). Crispr-Cas systems are enzymatic systems including two main components: a endonuclease (Cas) and a guide-RNA (single-guide RNA—sgRNA; a guide to the specific cleavage site of Cas endonuclease). The guide RNA may also include two components: a Crispr RNA (crRNA)—a sequence of 17-20 mer complementary to specific DNA genomic sequences and, optionally, a tracr RNA. The specific cleavage performed by endonuclease and guide by the sgRNA is repair by homologous recombination, specifically inserting the exogenous DNA flanked by the homologous sequences to the cleavage site. The introduction of this enzymatic system to the cell could occur by several methods, including using plasmids, through direct or indirect transformation, or using carriers like proteins and other chemical agents. The expression of the system components may occur in a transient or stable manner, using the cellular machinery of the receptor organism or being used in a exogenous way, in vitro, delivering to the target cell or tissue all the components ready to use (endonucleases+sgRNA, in vitro transcribed and combined before cell delivery). The description presented herein is not exhaustive and should not limit the use of different variations, systems and methods of genome editing on scope of the present invention, known in the state of the art and even the ones not yet discovered.

Following transformation, transgenic plants are selected from the transformed plant tissue and the progeny that have exogenous DNA can be selected using an appropriate marker such as kanamycin or ammonium glufosinate resistance. One skilled in the art is familiar with the composition of suitable selection media. Alternatively, other selection methods could be applied, without the insertion of any gene marker in the host genome (receptor organism) as described before.

Introduced genetic elements, whether in an expression vector or expression cassette, which result in the expression of an introduced gene will typically utilize a plant-expressible promoter. A "plant-expressible promoter" as used herein refers to a promoter that ensures expression of the genetic alteration(s) of the invention in a plant cell. Promoters suitable for plant expression may be isolated from plants or from other organisms. Several promoters have been isolated or developed including constitutive promoters, inducible promoters, and promoters that are responsive to tissue-specific abiotic stresses, among others. Many of these promoters have intronic sequences described as relevant for proper gene expression. In a preferred aspect of the invention, promoters are constitutive promoters and may be selected from the non-limiting group consisting of CaMV 35S, CoYMV (Commelina yellow mottle virus), FMV 35S, ubiquitin (Ubi), Actin Rice Promoter (Act-1), Act-2, nopaline synthase promoter (NOS), octopine synthase promoter (OCS), corn alcohol dehydrogenase promoter (Adh-1), PvUbi1, among others. In one embodiment of the invention, the promoter is the *Brachypodium distachyon* ubiquitin gene promoter (BdUbi10). In one embodiment of the invention, the promoter is the *Zea mays* ubiquitin gene promoter (ZmUbi1). Examples of promoters directing constitutive expression in plants are known in the art and include: the strong constitutive 35S promoters (the "35S promoters") of the cauliflower mosaic virus (CaMV), e.g., of isolates CM 1841 (Gardner et al, Nucleic Acids Res, (1981) 9, 2871-2887), CabbB S (Franck et al, Cell (1980) 21, 285-294) and CabbB JI (Hull and Howell, Virology, (1987) 86, 482-493); promoters from the ubiquitin family (e.g., the maize ubiquitin promoter of Christensen et al., Plant Mol Biol, (1992) 18, 675-689), the gos2 promoter (de Pater et al, The Plant J (1992) 2, 834-844), the emu promoter (Last et al, Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdhlS (GenBank accession numbers X04049, X00581), and the TRT promoter and the TR2' promoter (the "TRT promoter" and "TR2' promoter", respectively) which drive the expression of the G and 2' genes, respectively, of the T DNA (Velten et al, EMBO J, (1984) 3, 2723 2730). Alternatively, a plant-expressible promoter can be a tissue-specific promoter, i.e., a promoter directing a higher level of expression in some cells or tissues of the plant. These plant promoters can be combined with enhancer elements, they can be combined with minimal promoter elements, or can include repeated elements to ensure the expression profile desired.

In some embodiments, genetic elements to increase expression in plant cells can be utilized. For example, an intron at the 5' end or 3' end of an introduced gene, or in the coding sequence of the introduced gene, e.g., the hsp70 intron can be used. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence. Additional elements incorporated into the expression cassette for the purpose of enhancing gene expression levels, for example, transcriptional or translation enhancers such as CaMV 35S enhancers, FMV 35S, Nos, supP, among others.

Terminator sequences are also contemplated on the expression cassette. Examples of suitable and functional plant polyadenylation signals include those from the *Agrobacterium tumefaciens* nopaline synthase gene (nos), pea proteinase inhibitor II gene rbcS (ribulose-1,5-bisphosphate carboxylase small subunit), tobacco Lhcb 1 (tobacco chlorophyll a/b-binding proteins), heat shock protein (Hsp), CaMV 35S, octopine synthases, and alpha-tubulin genes among others.

An introduced gene of the present invention can be inserted in host cell DNA so that the inserted gene part is upstream (i.e., 5') of suitable 3' end transcription regulation signals (e.g., transcript formation and polyadenylation signals). This is preferably accomplished by inserting the gene in the plant cell genome. Preferred polyadenylation and transcript formation signals include those of the nopaline synthase gene (Depicker et al, J. Molec Appl Gen, (1982) 1, 561-573), the octopine synthase gene (Gielen et al, EMBO J, (1984) 3:835 845), the SCSV or the Malic enzyme terminators (Schunmann et al, Plant Funct Biol, (2003) 30:453-460), and the T DNA gene 7 (Velten and Schell, Nucleic Acids Res, (1985) 13, 6981 6998), which act as 3' untranslated DNA sequences in transformed plant cells. In some embodiments, one or more of the introduced genes are stably integrated into the nuclear genome. Stable integration is present when the nucleic acid sequence remains integrated into the nuclear genome and continues to be expressed (e.g., detectable mRNA transcript or protein is produced) throughout subsequent plant generations. Stable integration into and/or editing of the nuclear genome can be accomplished by any known method in the art (e.g., microparticle bombardment, *Agrobacterium*-mediated transformation, CRISPR/Cas9, electroporation of protoplasts, micro injection, etc.).

The term recombinant or modified nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As used herein, the terms "overexpression" and "upregulation" refer to increased expression (e.g., of mRNA, polypeptides, etc.) relative to expression in a wild type organism (e.g., plant) as a result of genetic modification. In some embodiments, the increase in expression is a slight increase of about 10% more than expression in wild type. In some embodiments, the increase in expression is an increase of 50% or more (e.g., 60%, 70%, 80%, 100%, etc.) relative to expression in wild type. In some embodiments, an endogenous gene is overexpressed. In some embodiments, an exogenous or heterologous gene is overexpressed by virtue of being expressed. Overexpression of a gene in plants can be achieved through any known method in the art, including but not limited to, the use of constitutive promoters, inducible promoters, high expression promoters, enhancers, transcriptional and/or translational regulatory sequences, codon optimization, modified transcription factors, and/or mutant or modified genes that control expression of the gene to be overexpressed.

Where a recombinant nucleic acid is intended for expression, cloning, or replication of a particular sequence, DNA constructs prepared for introduction into a host cell will typically include a replication system (e.g. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., plasma membrane localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell. A non-integrated expression system allows transient expression, e.g., of morphogenes, so that heterologous sequences are only expressed during a limited time period. In some embodiments of the present disclosure, morphogenes are transiently expressed at one or more stages of the transformation process, and then the plant produced using the transformation process does not include the morphogene.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein. Exemplary selectable markers include nptII, BAR, EPSPS, GUS, or fluorescent markers (e.g., GFP, CFP, etc.).

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Similarly, screening can be performed using polypeptide-based techniques including enzyme-linked immunosorbent assays (ELISAs), fluorescence detection (if a fluorescent marker was used), or Western blots. One of skill in the art will recognize that any polypeptide-based techniques available can be utilized in screening the inventions disclosed herein.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230: 1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present disclosure can also encompass homologues of the specifically disclosed sequences. Homology or genetic identity can be 50%-100%. In some instances, such homology or genetic identity is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Preferred host cells are plant cells. Plant cells from monocot species, including sugarcane (e.g., *Saccharum* spp.), corn (e.g., *Zea mays*), setaria (e.g., *Setaria italica*, *Setaria viridis*), or from dicot species such as *Brassica* spp., cotton (*Gossypium hirsutum*), potato (*Solanum tuberosum*), or tobacco (e.g., *Nicotiana benthamiana, Nicotiana tabacum*) may be used. Cells may be derived from tissue types including embryo, callus, leaf disk, and other explants. Plant cells can be differentiated or undifferentiated (e.g. callus, undifferentiated callus, immature and mature embryos, immature zygotic embryo, immature cotyledon, embryonic axis, suspension culture cells, protoplasts, leaf, leaf cells, root cells, phloem cells and pollen). Plant cells include, without limitation, cells from seeds, suspension cultures, explants, immature embryos, embryos, zygotic embryos, somatic embryos, embryogenic callus, meristem, somatic meristems, organogenic callus, protoplasts, leaf bases, leaves from mature plants, leaf tips, immature inflorescences, cotyledons, immature cotyledons, embryonic axes, meristematic regions, callus tissue, cells from leaves, cells from stems, cells from roots, cells from shoots, gametophytes, sporophytes, pollen and microspores. Plant cells further include various forms of cells in culture (e.g., single cells, protoplasts, embryos, and callus tissue), wherein the protoplasts or cells are produced from a plant part selected from the group of leaf, stem, anther, pistil, root, fruit, flower, seed, cotyledon, hypocotyl, embryo, or meristematic cell. Recombinant host cells, in the present context, are those which have been genetically modified to contain an isolated nucleic molecule, contain one or more deleted or otherwise non-functional genes normally present and functional in the host cell, or contain one or more genes to produce at least one recombinant protein. The nucleic acid(s) encoding the transgenes and morphogenes of the present invention can be introduced by any means known to the art which is appropriate for the particular type of cell, including without limitation, transformation, lipofection, electroporation or any other methodology known by those skilled in the art.

Having generally described this invention, the same will be better understood by reference to certain specific examples, which are included herein to further illustrate the invention and are not intended to limit the scope of the invention as defined by the claims.

EXAMPLES

The present disclosure is described in further detail in the following examples which are not in any way intended to limit the scope of the disclosure as claimed. The attached FIGS. are meant to be considered as integral parts of the specification and description of the disclosure. The following examples are offered to illustrate, but not to limit the claimed disclosure.

Example 1: Identification of Candidate Morphogenes in Grass Species

The following example describes the process used to identify candidate morphogenes. Although morphogenes have been identified in dicots, such as *Arabidopsis thaliana*, these dicot genes may not work in monocot plants, such as grasses. Further, because of the evolutionary history and complex genome of grass species (e.g., sugarcane), identification of candidate morphogenes in grass species is more complex. Sequence similarity provides a starting point, but additional analysis is needed.

Materials and Methods

*Arabidopsis thaliana* Morphogenes

Twelve genes from *Arabidopsis thaliana* were used as starting points for bioinformatic analysis. Each of these genes was considered to be a morphogene, i.e., a gene that has been functionally demonstrated to improve somatic embryogenesis and/or regeneration. The *A. thaliana* morphogenes were separated into three overlapping groups based on their effect.

The first group was those genes/proteins that allowed differentiated tissue (e.g., leaf tissue) to regain pluripotency and proliferation potential. These were SHOOT-MERISTEMLESS (STM), WUSCHEL (WUS), GROWTH-REGULATING FACTOR 5 (GRF5), WOUND INDUCED DEDIFFERENTIATION1 (WIND1), and ENHANCER OF SHOOT REGENERATION1 (ESR1).

The second group was those genes/proteins that promoted somatic embryo formation from callus. These were BABY BOOM (BBM), PLETHORA2 (PLT2), EMBRYOMAKER/AINTEGUMENTA-like 5/PLETHORA5 (EMK/AIL5/PLT5), LEAFY COTYLEDON (LEC2), AGAMOUS-LIKE 15 (AGL15), RWP-RK DOMAIN-CONTAINING 4 (RKD4), and SOMATIC EMBRYOGENESIS RECEPTOR KINASE 1 (SERK1).

The third group was those genes/proteins that promoted regeneration/organogenesis in embryos. These were BBM, ESR1, and GRF5.

Bioinformatic Methods

Three sequence database and analytics programs were used to identify candidate morphogenes in grass species using the *A. thaliana* morphogene proteins described above as a starting point. Gramene (gramene.org) was used to identify predicted orthologs of *A. thaliana* morphogene proteins. If predicted grass orthologs were present, then all orthologs and homologs were aligned and domain structure was identified. If no predicted grass orthologs were present, then the closest grass homolog branch was retrieved before aligning all orthologs and homologs and identifying domain structure. The domain structure was identified using InterPro Scan and relevant literature. From this alignment, two to three grass orthologs were selected with high similarity to the *A. thaliana* protein and one to two high confidence orthologs from dicots were selected with a high similarity to the *A. thaliana* protein. The selection process focused on proteins with high coverage (no partial matches), high similarity, and those having all the required domains known from the literature. The goal of this stage was to identify monocot orthologs from grass species and dicot orthologs from species closely related to *A. thaliana*.

Phytozome (phytozome.jgi.doe.gov/pz/portal.html) was used to retrieve homologs of *A. thaliana* proteins in grass species and in *A. thaliana*. All of the homologs were aligned, and the domain structures of the proteins were identified using InterPro Scan. Next, Maximum Likelihood phylogenetic trees were built using FastTree on the basis of these alignments. Then, the trees were analyzed to identify homologs in grass species and in sugarcane that were closest to ortholog branches. On the basis of this analysis, candidate morphogenes in grass species and sugarcane were selected. The selection process focused on proteins with high coverage (no partial matches), high similarity, those having all the required domains known from the literature, and those with a phylogenetic position on the tree that was closest to the orthologs. The goal of this stage was to identify additional grass homologs if there were no grass orthologs predicted by Gramene, and to generate lists of unbiased homologs to build phylogenetic trees.

NCBI tblastn (blast.ncbi.nlm.nih.gov/Blast.cgi?PROGRAM=tblastn&PAGE_TYPE=BlastSearch&LINK_LO C=blasthome) was used with *A. thaliana* proteins as bait against Transcriptome Shotgun Assembly (TSA) of the *Saccharum* genus. This provided a range of coverage and identity and was used to select the best candidates, which were usually partial. Then, the full transcript sequence was retrieved by additional blast search to a whole genome assembly (WGA) or published PacBio RNA-Seq data sets (e.g. Nascimento et al., 2016). The more full length protein predictions obtained from this second step were then aligned with previously identified orthologs and homologs, and the domain structures of the proteins were identified using InterPro Scan. Next, Maximum Likelihood phylogenetic trees were built using FastTree on the basis of these alignments. From this, one to two predicted sugarcane homologs were then selected. The selection process focused on proteins with high coverage (no partial matches), high similarity, those having all the required domains known from the literature, and those with a phylogenetic position on the tree that was closest to the orthologs. The goal of this stage was to identify sugarcane homologs.

All three of these bioinformatic approaches were applied to each candidate morphogene that was ultimately selected.

Results

The analysis identified multiple candidate morphogenes in grass species and sugarcane. The results were compared with sequences from publications, and in some cases, previously identified orthologs were found to be incorrect. For example, the analysis revealed that the published ortholog of *A. thaliana* BBM in *Zea mays* (Lowe et al., 2016, Plant Cell 28(9):1998-2015) was located in a separate clade on the phylogenetic tree ("clade 2"), which contained the *A. thaliana* AIL6 protein. In contrast, the *Z. mays* BBM ortholog identified in the analysis was located in "clade 1", which contained the true BBM grass ortholog genes. Multiple grass genes in clade 1 were identified that encoded proteins that contained the same seven protein motifs as *A. thaliana* BBM. Two of these were selected for further analysis, including one in the wheat genus and one in the sugarcane genus. In addition, one gene from clade 2 was selected for further analysis. This gene was the *Panicum hallii* (switchgrass) gene phylogenetically closest to the published *Z. mays* BBM gene and the *Oryza sativa* BBM gene (Lowe et al., 2016, Plant Cell 28:1998-2015). Analysis of the domains in the protein encoded by this gene showed that it contained two domains shared by other grass proteins in this clade that were not present in *A. thaliana* BBM.

Further, variation was identified between dicot and monocot morphogene protein domains. These meant that a standard approach of identifying homologs/orthologs by sequence and/or motif similarity would not have successfully been able to identify these proteins. For example, the sugarcane homolog of AGL15 did not contain two protein domains present in the AGL15 proteins of *A. thaliana* and its close relative *B. napus*. Both the sugarcane and the *B. napus* AGL15 proteins were selected for further testing. Another known *A. thaliana* morphogene, RKD4, belongs to the RKD(A) subfamily of RKD-RW domain proteins, which is characterized by an additional undescribed C-terminal domain and a missing PB1 domain (Chardin et al., 2014

Journal of Experimental Botany 65(19):5577-5587). In the analysis, identified grass homologs of RKD4 were found to have this characteristic C-terminal domain ("motif 12"). In addition, grass homologs of RKD4 were found to have extra domains not present in dicot RKD4 sequences.

On the basis of the analyses described above, the twenty candidate morphogenes listed in Table 1 were selected for further evaluation.

TABLE 1

Candidate morphogene polynucleotides and polypeptides

| Species | Morpho-gene family | Polynucleotide sequence | Polypeptide sequence |
|---|---|---|---|
| Saccharum spp. hybrid | AGL15 | SEQ ID NO: 1 | SEQ ID NO: 21 |
| Brassica napus | AGL15 | SEQ ID NO: 2 | SEQ ID NO: 22 |
| Saccharum spontaneum | BBM | SEQ ID NO: 3 | SEQ ID NO: 23 |
| Triticum urartu | BBM | SEQ ID NO: 4 | SEQ ID NO: 24 |
| Panicum hallii | BBM | SEQ ID NO: 5 | SEQ ID NO: 25 |
| Saccharum spontaneum | ESR1 | SEQ ID NO: 6 | SEQ ID NO: 26 |
| Setaria italica | ESR1 | SEQ ID NO: 7 | SEQ ID NO: 27 |
| Oryza longistaminata | GRF5 | SEQ ID NO: 8 | SEQ ID NO: 28 |
| Saccharum spontaneum | GRF5 | SEQ ID NO: 9 | SEQ ID NO: 29 |
| Saccharum spontaneum | LEC2 | SEQ ID NO: 10 | SEQ ID NO: 30 |
| Brassica oleracea | LEC2 | SEQ ID NO: 11 | SEQ ID NO: 31 |
| Brachypodium distachyon | PLT2[1] | SEQ ID NO: 12 | SEQ ID NO: 32 |
| Leersia perrieri | PLT2 | SEQ ID NO: 13 | SEQ ID NO: 33 |
| Panicum hallii | RKD4 | SEQ ID NO: 14 | SEQ ID NO: 34 |
| Saccharum spontaneum | SERK1 | SEQ ID NO: 15 | SEQ ID NO: 35 |
| Setaria italica | SERK1 | SEQ ID NO: 16 | SEQ ID NO: 36 |
| Saccharum spontaneum | STM | SEQ ID NO: 17 | SEQ ID NO: 37 |
| Saccharum spontaneum | WIND1 | SEQ ID NO: 18 | SEQ ID NO: 38 |
| Brassica napus | WIND1 | SEQ ID NO: 19 | SEQ ID NO: 39 |
| Panicum hallii | WUS | SEQ ID NO: 20 | SEQ ID NO: 40 |

[1]Also known as EMK1.

Example 2: Testing of Candidate Morphogenes and Assessment of the Ability of Candidate Morphogenes to Increase Transformation and Regeneration Efficiency The following example describes testing of candidate morphogenes to identify their effectiveness. In addition, the example describes testing of candidate morphogenes using a visual reporter construct in order to assess transformation and regeneration efficiency in sugarcane cells.

Materials and Methods
Plasmids and Candidate Morphogenes

Individual morphogenes were tested using the same expression system with the same promoter, terminator, reporter, and selectable marker. Plasmids with the expression cassettes pBdUbi10::morphogene::tPin2A, pScBv::td-Tomato::tAtHsp, and pZmUbi1::nptII::tNOS were used (FIG. 1). These plasmids used the visual reporter tdTomato as a model transgene of interest. FIGS. 4A-4B and 5A-5B provide the candidate morphogenes that were tested (see also Table 1, above). These morphogenes were driven by a ubiquitin promoter, pBdUBi10 (Coussens, G., et al. (2012). *Brachypodium distachyon* promoters as efficient building blocks for transgenic research in maize. Journal of experimental botany, 63(11), 4263-4273), as shown in FIG. 1.

In addition to the plasmids testing morphogenes, two control plasmids were tested. One control plasmid contained GFP in place of the candidate morphogene sequence, and was used as a negative control. The other control plasmid contained WUSCHEL (U.S. Pat. Pub. No. 2017/0121722) in place of the candidate morphogene sequences, and was used as a positive control.

The expression cassette (FIG. 1) included restriction sites intentionally designed to allow exchange of expression cassette components. For one, different promoters can be inserted for testing to optimize expression of the morphogenes. For another, different morphogenes (or multiple morphogenes) can be tested within the same plasmid design. Finally, the selection marker can be removed if necessary. These plasmid modifications may be employed during testing.

Testing Systems

The first testing system used the low-transformable sugarcane tissue of leaf disks from a moderately recalcitrant sugarcane variety. The second testing system used callus cells from a highly recalcitrant sugarcane variety.

The quantification of each testing system was done in two ways. The first of these was the reporter fluorescence, and the second of these was the timing and amount of embryogenic callus.

Agrobacterium Transformation Protocol for Leaf Disk Transformation (Moderately Recalcitrant Variety)

On Day 1, sugarcane tillers of the moderately recalcitrant sugarcane variety were induced on media. On Day 2, transformation was done. Induced sugarcane leaf disk cells were transformed with *Agrobacterium* strain AGL1 containing the plasmids described above. The use of leaf disk cells for transformation was for preliminary evaluation.

For each construct, about 50 leaf disks were used. The leaf disks were sonicated in infection medium for 5 minutes. Then, they were vacuum-infiltrated with the *Agrobacterium* suspension ($OD_{600}=0.5$)+200 μM acetosyringone for 10 minutes. The mixture was shaken at 65 rpm, 28° C. for 10 minutes. Subsequently, the leaf disks were dried on filter paper in a hood for about 20 minutes. After drying, the leaf disks were transferred to co-culturing media.

After 3 days of co-cultivation, the leaf disks were transferred to resting media on Day 5. On Day 11, the leaf disks were transferred to selection media containing geneticin.

Proliferation of callus clusters expressing tdTomato was quantified at the start of selection (Day 11) and every 7 days thereafter (Day 18, Day 25, and Day 32) for a total of 4 weeks. The expression of TdTomato was indicative of how many cells were successfully co-transformed with the morphogene and the fluorescence gene (e.g., TdTomato), and was used as a proxy for transformation efficiency.

Agrobacterium Transformation of Callus Tissue (Highly Recalcitrant Sugarcane Variety)

In a further experiment, callus cells of the highly recalcitrant sugarcane variety were transformed with *Agrobacterium* strain AGL1 containing the plasmids described above. The use of callus cells is for stable transformation and for producing regenerated plants.

Microprojectile Bombardment Transformation

In another experiment using the plasmids described above, pre-callus sugarcane leaf disk cells are transferred to osmotic media for 4 hours prior to microprojectile bombardment. The use of leaf disk cells for transformation is for preliminary evaluation. Bombardment is carried out with a Biolistic-PDS100 system (Biorad) as follows: 100 μg of 0.6

µm gold particles were coated with 100 ng vector using TransIT. After incubating on ice and pelleting by centrifugation, supernatant is removed and the gold particles are resuspended in 70% ethanol. Once the suspension is allowed to dry onto macrocarriers, it is propelled into sugarcane leaf disks using 1000 psi of pressure in −27 in Hg vacuum from a distance of 6 cm.

Bombarded leaf disks are left on osmotic medium overnight at 27° C. and then transferred to resting media for 7 days. Next, disks are transferred to selection media containing geneticin. The rest of the experiment is conducted as detailed for *Agrobacterium* transformation above.

In an additional experiment using the plasmids described above, sugarcane callus cells are exposed to microprojectile bombardment using a standard particle bombardment protocol for sugarcane. The use of callus cells is for stable transformation and for producing regenerated plants.

Results

Figure 4A:
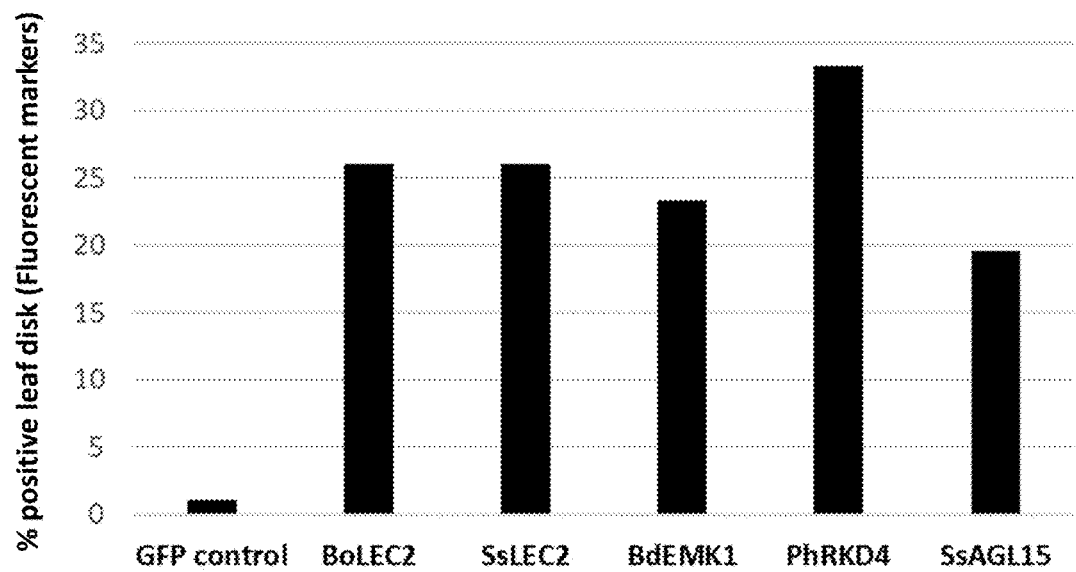
FIGS. 4A-4B show the results of leaf disk transformation of a sugarcane variety considered a moderately recalcitrant variety for transformation.
Figure 4B:
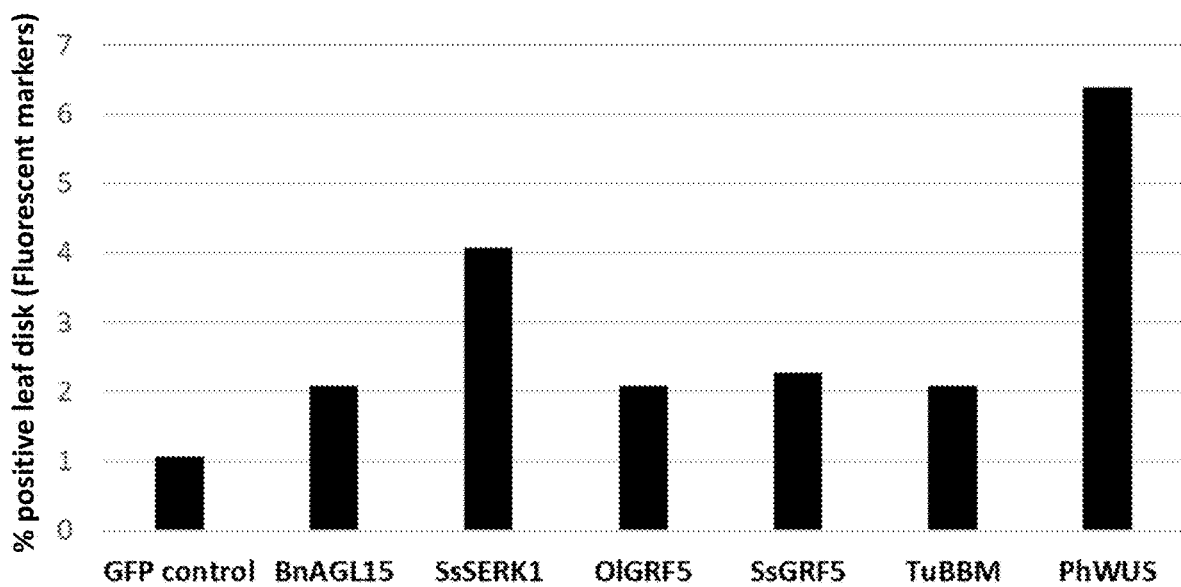

FIGS. 4A-4B show the experimental results for leaf disk transformation of the moderately recalcitrant sugarcane variety. The percentage of disks with tdTomato fluorescence clusters is shown after 21 days from the beginning of the experiments. Visualization of tdTomato fluorescence was used to observe increase in cell proliferation for leaf disks. Relatively high cell proliferation was seen for leaf disks transformed with plasmids containing some of the candidate morphogenes such as PhWUS, BdEMK1/BdPLT2, PhRKD4, BoLEC2, ScLEC2, and SsAGL15. Further, this increase was shown relative to the cell proliferation of callus clusters transformed with a control vector containing GFP (negative control) in place of the morphogene coding sequence.

As can be seen from the results shown, a number of effective morphogenes were identified. Foremost among them were PhRKD4 and BdEMK1/BdPLT2. Additional promising candidates included BoLEC2, SsLEC2, SsAGL15, and PhWUS.

Figure 5A:
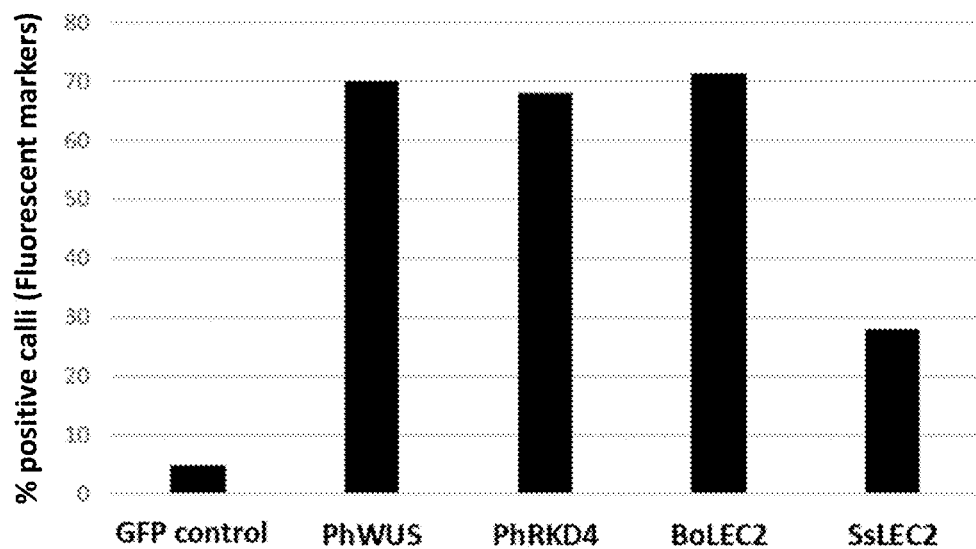
FIGS. 5A-5E show summary graphs of the results of callus transformation of a sugarcane variety considered highly recalcitrant variety for transformation as well as representative images of callus transformation of this variety.
Figure 5B:
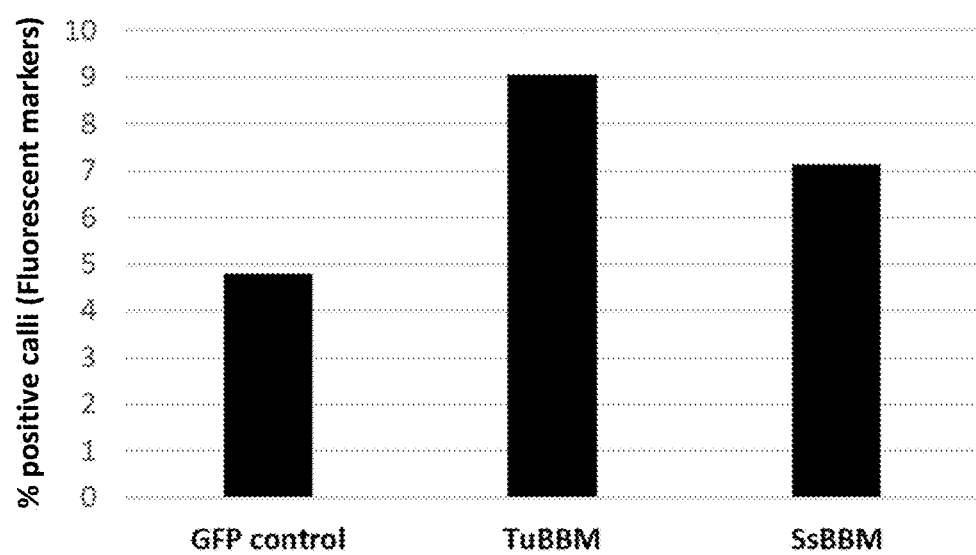
Figure 5C:
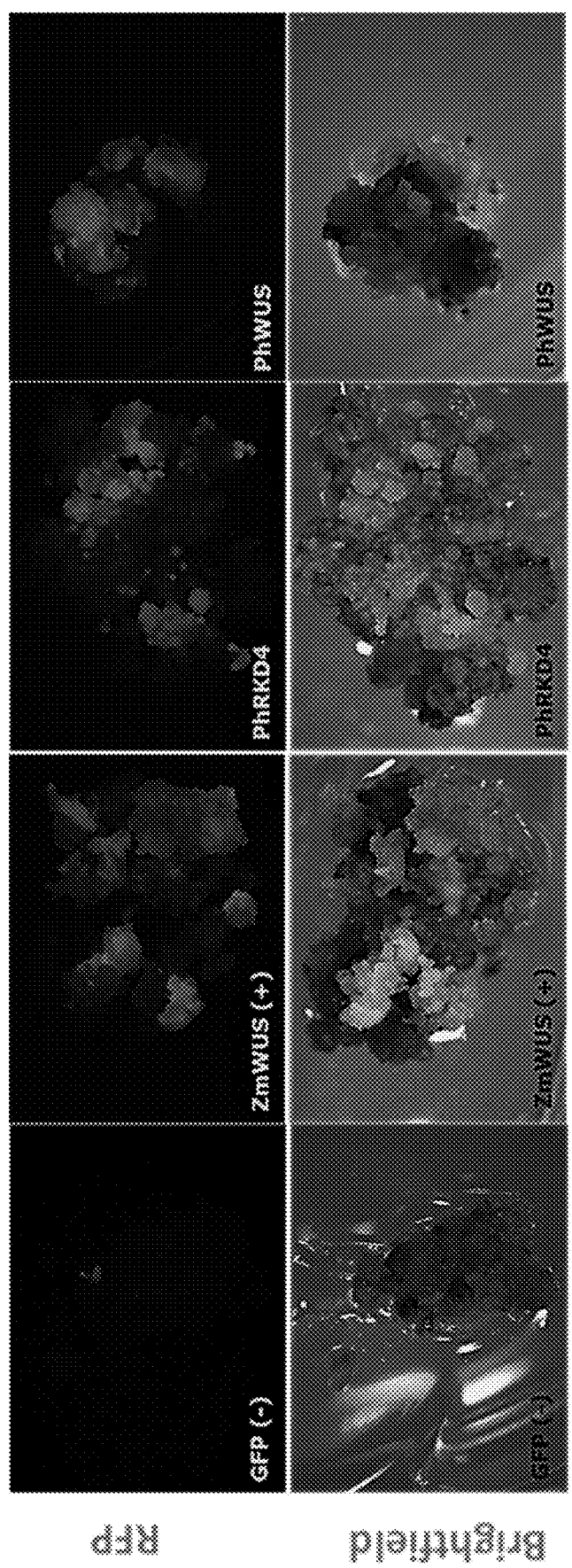
Figure 5D:
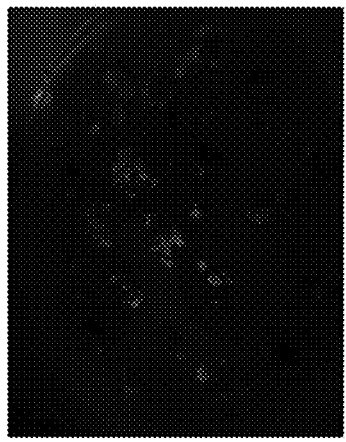
Figure 5D:
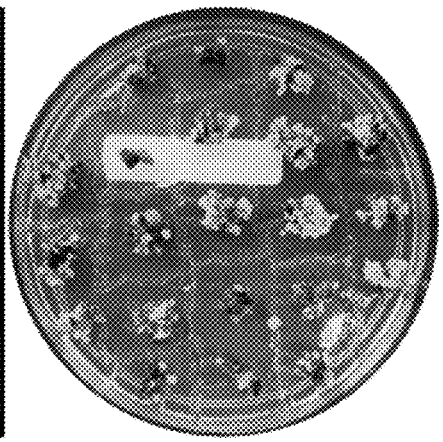
Figure 5D:
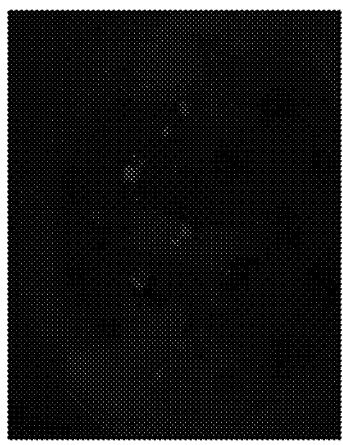
Figure 5D:
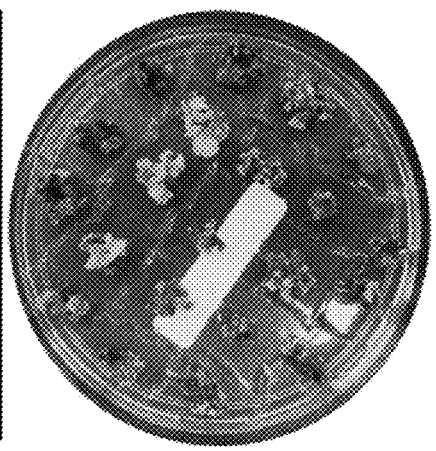
Figure 5D:
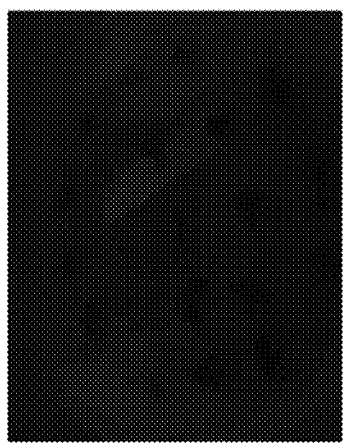
Figure 5D:
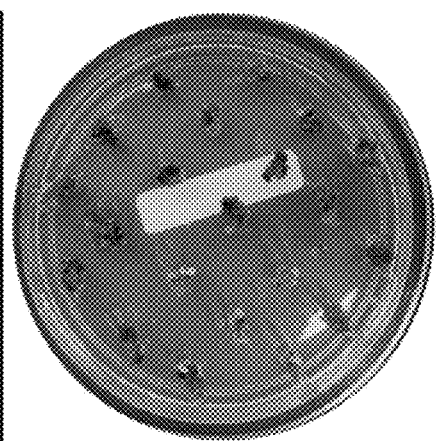
Figure 5E:
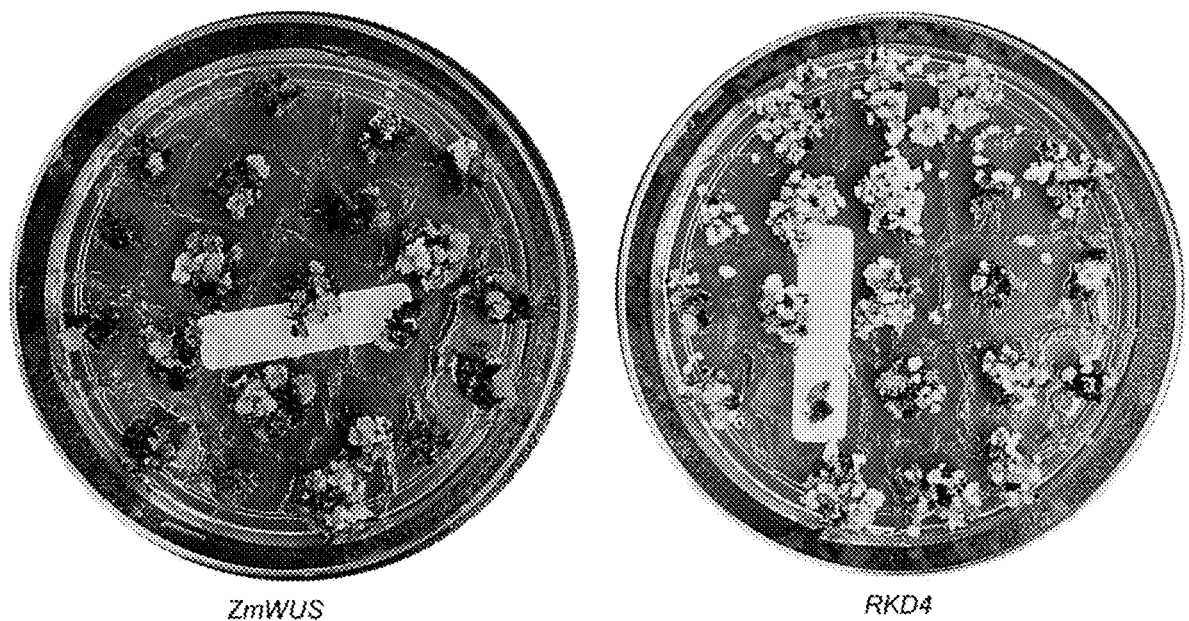

FIGS. 5A-5E show the experimental results for callus transformation of the highly recalcitrant sugarcane variety. FIGS. 5A-5B show summary graphs of the results of transforming sugarcane calli with candidate morphogenes. These results identified a number of effective morphogenes, primarily PhRKD4, BoLEC2, SsLEC2 and PhWUS. Without wishing to be bound by theory, it is thought that these four candidate morphogenes may be suitable for transforming both moderately recalcitrant sugarcane varieties and highly recalcitrant sugarcane varieties. FIG. 5C shows that multiple areas of fluorescence were observed in the callus transformed with the ZmWUS positive control, the PhRKD4 morphogene, and the PhWUS morphogene (light areas in RFP images), but no fluorescence was observed in the GFP negative control. FIG. 5D shows that the calli transformed with the ZmWUS positive control and the PhRKD4 morphogene grew more (e.g., proliferated), than the calli transformed with the GFP negative control. FIG. 5E shows a comparison of the calli transformed with the ZmWUS positive control and the PhRKD4 morphogene.

The transformed callus cells will be used to regenerate plantlets and plants for further evaluation.

101.211 The results of these tests will provide information regarding the efficacy of the morphogene itself and with additional hormones or triggers to enhance morphogene effect of cell division/embryo formation. The most effective morphogenes identified in these tests will be used for further testing.

Example 3: Co-Delivery of Candidate Morphogenes with Genes of Interest to Sugarcane Leaf Disks or Callus The following example describes the co-delivery of candidate morphogenes with genes of interest (e.g., genome editing reagents) using a single plasmid containing a selectable marker. The genome editing reagents are used to edit the sugarcane genome and generate "native traits" based on the edited phenotype.

Materials and Methods

Homologous Recombination (HR) Events

In a first option, a single construct containing genome editing reagents pSCBV-ScoLbCPF1-LWcrRNAarray-tAtHSP18 and HR template, a fluorescent reporter pFMV-erGFP-tPin2A, a selectable marker pZmUbi-NPTII-T-Nos and candidate morphogenic genes is used. In a second option, a construct containing genome editing reagents pSCBV-ScoLbCPF1-LWcrRNAarray-tAtHSP18, a fluorescent reporter pFMV-erGFP-tPin2A, a selectable marker pZmUbi-NPTII-T-Nos, and candidate morphogenic genes is used, and the HR template is delivered separately. In a third option, a construct a fluorescent reporter pFMV-erGFP-tPin2A, a selectable marker pZmUbi-NPTII-T-Nos, and candidate morphogenic genes is used, the HR template is delivered separately, and the genome editing reagent is delivered separate in the form of a ribonucleoprotein (RNP). Table 1, above, describes the candidate morphogenic genes, and FIG. 2A illustrates the three options.

In order to generate, e.g., homologous recombination (HR) events, the plasmids described above are delivered to sugarcane leaf disks or sugarcane callus cells using either *Agrobacterium* transformation or particle bombardment as described in Example 2 and shown in FIG. 2A. HR events are suitable for testing as they can be used both to create small edits in a native gene or to insert a larger segment of DNA for the purposes of site-directed integration (SDI). Selection genes, e.g. geneticin, are used to screen the regenerated plants with stable integration of the transgene for the desired KO edits.

Knockout (KO) Events

In a first option, a single construct containing genome editing reagents pSCBV-ScoLbCPF1-LWcrRNAarray-tAtHSP18 (yellow arrow), a fluorescent reporter pFMV-erGFP-tPin2A (navy arrow), a selectable marker pZmUbi-NPTII-T-Nos (purple arrow), and morphogenic genes (bright blue box) is used. In a second option, a construct containing a fluorescent reporter pFMV-erGFP-tPin2A (navy arrow), a selectable marker pZmUbi-NPTII-T-Nos (purple arrow), and morphogenic genes (bright blue box) is used, and the genome editing reagent is delivered separately in the form of ribonucleoprotein (RNP). Table 1, above, describes the candidate morphogenic genes, and FIG. 2B illustrates the two options.

In order to generate knockout (KO) events, the plasmids described above are delivered to sugarcane leaf disks or sugarcane callus cells using either *Agrobacterium* transformation or particle bombardment as described in Example 2 and shown in FIG. 2B. Selection genes, e.g. geneticin, are used to screen the regenerated plants with stable integration of the transgene for the desired KO edits.

Results

Co-delivery of candidate morphogenes with genome editing reagents will result in improved HR and KO event outcomes. As HR occurs naturally in cells that are actively dividing, the morphogenes will increase the HR event efficiency, because the morphogenes directly increase the rate of cell division. For KO edits, the morphogenes will enable cells to be transformed more efficiently with the necessary genome editing reagents. The use of morphogenes will not result in higher KO event efficiencies, as the morphogenes are used for the transformation part of the gene editing.

Example 4: Generation of Transgene-Free Knockout Events Using Genome Editing

The following example describes the co-delivery of candidate morphogenes with genome editing reagents in order to produce transgene-free knockout events.
Materials and Methods
Transgene-Free Knockout (KO) Events
In a first option, a single construct containing genome editing reagents pSCBV-ScoLbCPF1-LWcrRNAarray-tAtHSP18, a fluorescent reporter pFMV-erGFP-tPin2A and candidate morphogenic genes is used. In a second option, a construct containing a fluorescent reporter pFMV-erGFP-tPin2A and candidate morphogenic genes is used, and the genome editing reagent is delivered separately in the form of ribonucleoprotein (RNP). Table 1, above, describes the candidate morphogenic genes, and FIG. 3 illustrates the two options.

In order to generate transgene-free knockout (KO) events, the plasmids described above are delivered to sugarcane leaf disks or sugarcane callus cells using either *Agrobacterium* transformation or particle bombardment as described in Example 2 and shown in FIG. 3.

Without selection, regenerated plants are screened for the desired KO edits without the transgene integration. Genes providing visual markers (e.g., LemonWhite, GFP, etc.) are used to screen for edits and/or are used for sequence-based analysis. Preferably, a phenotype is observed, and a confirmation of the edit is made using sequence information. The absence of the transgene is confirmed using sequence-based tools, e.g., PCR or sequencing.
Results
Co-delivery of candidate morphogenes with genome editing reagents will result in transgene-free KO events.

Example 5: Testing Combinations of Candidate Morphogenes

The following example describes testing of combinations of candidate morphogenes to identify their effectiveness.
Materials and Methods
Plasmids and Candidate Morphogenes
Combinations of the most effective morphogenes identified in Example 2 are tested. Different promoters are used for high expression testing and low expression testing, and various promoter combinations are used to fine tune morphogene expression.
Testing Systems
Dose/pulse experiments with different promoter combinations are used to determine the level of expression required. The timing of application and transformation is varied.
Results
Optimal combinations and expression levels of morphogenes will be identified.

What is claimed is:

1. A method of producing a genetically altered sugarcane plant, comprising:
   a) providing sugarcane cells or tissue;
   b) introducing into the sugarcane cells or tissue a morphogene nucleotide sequence comprising SEQ ID NO: 14 and at least one transgene nucleotide sequence to produce transgenic sugarcane cells, wherein the introduction of the morphogene nucleotide sequence is transient; and
   c) cultivating the transgenic sugarcane cells for proliferation and/or regeneration.

2. The method of claim 1, further comprising:
   d) cultivating the transgenic sugarcane cells into genetically altered plantlets; and
   e) growing the genetically altered plantlets into genetically altered plants comprising the at least one transgene nucleotide sequence.

3. The method of claim 1, further comprising screening the sugarcane cells between steps (b) and (c) for the morphogene nucleotide sequence and the transgene nucleotide sequence, screening the sugarcane cells during step (c) for the morphogene nucleotide sequence and the transgene nucleotide sequence, or screening the sugarcane cells after step (c) for the morphogene nucleotide sequence and the transgene nucleotide sequence, and optionally further comprising selecting the transgenic sugarcane cells between steps (b) and (c), or selecting the transgenic sugarcane cells after step (c), optionally by using selectable markers.

4. The method of claim 1, wherein step (b) is achieved through *Agrobacterium* transformation.

* * * * *

SEQUENCE LISTING

<160> NUMBER OF SEQ ID NOS: 40

<210> SEQ ID NO 1
<211> LENGTH: 672
<212> TYPE: DNA
<213> ORGANISM: Saccharum hybrid

<400> SEQUENCE: 1

```
atggggaggg aaaggattgc aattcgtcgg attgacaacc tcgccgcacg gcaggtcacc      60
ttctccaaga gacgccgggg actgttcaag aaagccgagg aactcagcat actctgcgat     120
gccgaggtcg gcctcgttgt attctccgca acgggtaaac tcttccactt cgcctctacg     180
tctatgaagc aggtgatcga tcgttacgac tcccactcca agaatctcca aaagagtgag     240
gctcttagcc agctacagag ccatattgat gacggcactt gctcgcggct caaggaggaa     300
ctcgcggaaa cgagcctaaa gctccgccag atgagggggg aagagttgca gcgactcagt     360
gtgcagcaac tacaggagtt ggaaaagacc ttggaatccg gcctgggtag tgtccttaag     420
acgaagagcc agaagatcct cgatgagatt tctggcctgg aacggaagcg gatggagttg     480
atcgaggaaa acagcaggct taaggaacag gtaacccata tggccaggat ggagacccag     540
ctcggcgtgg acagcgagat tgtgtatgaa gaggggcagt ctagcgagag cgtcacgaac     600
accagttatc cgcggccaag caccgatacg gatgactgca gcgataccag tctcaggttg     660
ggtctgccct aa                                                          672
```

<210> SEQ ID NO 2
<211> LENGTH: 795
<212> TYPE: DNA
<213> ORGANISM: Brassica napus

<400> SEQUENCE: 2

```
atggggaggg gcaagattga aattaagcgt attgagaacg ccaacagccg gcaggtcacc        60
ttctccaaga gacgcgcggg actgcttaag aaagcccatg aactaagcgt cctgtgtgac       120
gccgaagtgg ccgttatagt gttcagcaag tctggcaagc tgttcgagtt ctcttccact       180
cgctgcatga agaaaaccct tttgaggtac ggcaactacc agattagctc agatgtccct       240
ggtattaacc gcaaagcgga aaatcaggag tgcactgaag tggatctcct taaggacgag       300
atatccatgc tacaagagaa gcatttgcaa atgcagggca agcggctgaa cctcctttct       360
ctaaaggagt tgcaacatct ggagaaacag ctgaatttta gtctcatttc agtgagggaa       420
cgaaaggagc tccttctgac gaagcagctg aagagtcga ggttgaagga gcaacgggca        480
gaactggaga tgaaacgct aaggcggcag gtgcaggagc ttaggtcctt cctcccatca        540
attaatcagc actatgttcc tagttacata aaatgcttcg cgatcgatcc gaagaaaagt       600
ctcctgtcga cacgtgcct aggtgacatc aactgctctc ttcagaacac aaatagcgat        660
acaacccttc aactcgggct cccaggagag gctcacgaca cacgcaagaa cgagggtgat       720
agggagtcgc catccagtga tagcgtgacc acgtccacca ctagagctac agcacaaaga       780
atctcgttgg tctaa                                                        795
```

<210> SEQ ID NO 3
<211> LENGTH: 2061
<212> TYPE: DNA
<213> ORGANISM: Saccharum spontaneum

<400> SEQUENCE: 3

```
atggcgtcag ccaacaattg gttgggattt tctttgtctg gccaagacaa cccacagccg        60
aaccaccaag attcgagccc ggcggcagcg ggcatcgaca tcagcggagc aagcgacttt       120
tacggcctcc ccacccagca aggatccgat ggacatttgg gcgtccccgg cctgcgcgat       180
gaccatgctt cctacggcat catggaggct ttcaaccgcg tgccgcagga cacaagat         240
tggaacatgc gtggtcttga atacaacggg ggaggttcgg agctgtctat gctcgtgggt       300
agctcgggcg gaggggagg gggaggcaag agggcggttg aggatagtga gccgaagctc       360
gaagattttc taggcggtaa tagctttgtg tctgaacagg accagtctgg cggatatctc       420
ttcagtggag tgcccatggc cagctcgacg aattctaact ccggatcgaa cactatggag       480
ttgagcatga ttaaaagctg gctgcggaat aaccaagtgc cacaaccgca gcccctgcc        540
gctcccacc agccacaacc cgaggaaatg tcgactgacg cttctgctag ttccttcggc        600
tgctccgaca gtatgggtcg caatggcaca gtggctgccg cgggcagctc tcaaagtctc       660
gccttgtcga tgtcaaccgg atcccacctg ccaatggtag tggccggagg gggcgccagc       720
ggggctgcct cagaatccac gtccagtgag aataaacgag cgagcggggc catggatagc       780
cccggctccg cggtcgaggc agttccaaga aaaagcatcg atactttcgg ccaacgaca        840
tcgatttaca gagggtcac tagacatcgc tggactggac gttatgaagc tcacctgtgg       900
gataattcat gccgccggga aggccagtct cggaaggaa ggcaagtgta cttgggcgt         960
tacgacaaag aagataaggc cgctagagcc tatgacctgg ccgcactcaa gtattggggg      1020
accacaacta ccacaaattt cccgatttca aactacgaga aggaggtgga ggaaatgaaa      1080
cacatgacta gacaggaata catcgcatat ctccgcagga attcttccgg gttctcccgc      1140
ggcgcttcta agtacagggg tgttacgcgg caccatcagc acggccgctg gcaagctcgc      1200
attggccgtg tggcgggtaa caaagatctt tacctgggta ccttttccac ggaggaagag      1260
```

-continued

```
gccgctgaag cctatgacat cgctgccatt aaattccggg ggctgaacgc agtcaccaac      1320
ttcgatatga gtcgatacga cgttaagagc atcttggaat catccactct gccggtaggc      1380
ggtgccgcga ggcgcctgaa ggacgctgtt gaccacgtgg aagctggagc aactatctgg      1440
cgcgctgaca tggacggcgg agtaatatca caacttgcag aggcgggtat gggaggctac      1500
gcgagctacg gtcaccatgg ctggccaacc attgccttcc agcaaccgtc gccactgtca      1560
gtccactatc catatggcca gcctccgtcg cgtgggtggt gtaagccaga gcaggacgct      1620
gcggtggcgg cagctgcaca ctccctccag gacctgcagc aacttcactt gggttccgct      1680
gcggcacaca atttctttca ggccagttcc tctagtgccg tgtacaactc gggcggggca      1740
gcctccggcg gatatcaggg tctcggaggc gggggttcct cgttcctgat gccaagtagc      1800
acggtcgtgg cagccgcaga ccaaggacat agttctacag ccaaccaagg ttccacttgc      1860
agttatggag atgaccacca ggagggaaag cttataggtt acgacgccat ggttgccgca      1920
acggcggctg caggtggaga tccctacgcg gctgcgcgct ctgggtacca gttcagtcag      1980
ggatccggca gcactgtgtc aatcgccagg gcgaacggat atagcaacaa ttggtcttcg      2040
cctttcaatg gaatgggata a                                               2061
```

<210> SEQ ID NO 4
<211> LENGTH: 1455
<212> TYPE: DNA
<213> ORGANISM: Triticum urartu

<400> SEQUENCE: 4

```
atggcgtcag ccaacaattg gttgggattt tctttgtctg gccaaggctc ccaccctcag       60
ccacaccaaa atggtagccc ggcggcagcg gccatcgacg gggacttcta cggactgcag      120
gcccagaccg ccccagatgc acacctggga atgtcctctc tcagggccga cgccaactat      180
ggggttatgg acgccttcaa cgggggtaca aagagaccc aggattgggc gatgaggggc       240
cttgactatc atggtggatc cagcgagctc tctatgcttg tgggctctag cgggggtaga      300
atgacggtgg acgatgggga agcgccaaaa cttgaagatt ttctcggggg caattcgttc      360
tcagacgcgc aggaccacgc tggtagctat ctgtttagct ccggctccgc tatgggcagt      420
ggggccgcga gtggatcaca cggcgtcgat gggcggggtg gctccacaat tgaattgtcc      480
atgattaaaa cgtggctcag aaacgataat acgaagctc aacacgatca ggagatgtcg      540
gccgatgcct ccgccacaag ctacgcgtgt tcgggcgctc ctggtagtac cagcaacggg      600
gtgggcgtcg cttcgtccag gggacagggt ctggcgctca gcatgtctat gggcagtaac      660
tcacatcctc agatgcccgt agtgccagcg gcagtaggga ccgaatccac cagtagcgag      720
aataagaggg tagattcccc gtcagctggg accgccgatg cagtgcaacg gaaatcaatc      780
gacaccttcg ggcaacgtac aagcatatac cgaggtgtta ccaggcaccg gtggacaggt      840
cggtacgaag ctcacttgtg ggacaattcc tgtagacgtg agggccagac ccgcaagggt      900
aagcaaggcg gttacgacaa ggaggataaa gcagccaggg cgtacgatct ggcggcactc      960
aaatactggg ggacgaccac tacaacgaat atccccatca gcacatatga aaggagata      1020 gaggaaatga agcacatgac gcgccaggag tacatagcat acttgcgacg caatagctca      1080
ggtttctcta gaggggccag caagtaccgc ggcgtgactc gccatcacca acaggggcgc      1140
tggcaggctc gtattggaag ggttgctggg aataaggacc tgtaccttgg cactttttacg      1200 accgaggaag aggcggctga ggcgtacgat attgcagcga ttaagttttcg cgggcttaac      1260
```

```
gctgtcacca atttcgagat gtctcgctat gacgtgaagt cgatcctcga aggctcaaca   1320
ctcccgacct gcatgctacc gtgtatgcat ttcacggcta agtcaaactc tgcctcggaa   1380
aggcttaaat ccatagagct gtctaccggg cagtgcacaa tcttcgctaa cgtccagaag   1440
cagtttgaca cctaa                                                   1455

<210> SEQ ID NO 5
<211> LENGTH: 2139
<212> TYPE: DNA
<213> ORGANISM: Panicum hallii

<400> SEQUENCE: 5
atggcgaccg tcaacaattg gttggcattt tctttgtctc cccaagacct gccaccttcc     60
caaaccgact ccactctaat ctcggcagcg gccacggacg aggtcagcgg agacgtgtgt    120
ttcaacatcc cccaagattg gggaatgcgc gggagcgagt tgagcgccct ggtctcagag    180
cctaagttgg aggacttcct cggggggtatc aacttctccg agcagcatca caaagccaat   240
ctcaatgtta ttccatccag ctcgagcact tgttatgcct ctagcggggc tagcacgggc    300
taccatcacc aactgtacca ccatccgagt tccgctctcc atttcgctga ttcagtcatg    360
gtcgcgtcta cgccggtgt tcacgatggc ggtgcaatgc tgtccgcggc tgccgcaaat    420
ggcggggccg gagccgcggg cgcaaatggg ggctctatcg ggctctcgat gatcaagaat    480
tggttgaggt cgcaaccagc ccctccgcca cagccaaggg tggccgtggc ggagggggcc    540
caggccgcac aaggcctttc gcttagtatg aatatggctg gtacccaggg agccgggatg    600
ccgctgctcg ctggggagag ggacagagct ccggagagtg tatctaccag tgcccagggt    660
ggggccgtcg cagcgagaaa ggaagactcg ggcggagcgg gcgccctcgt ggctgtgtca    720
acagatacgg gcgggtctgg gggagcctcg gcagagaccg ttgcacgaaa gaccgtggac    780
acgttcggtc aaagaacaag catctatcgt ggcgtcacac ggcaccggtg gacgggcaga    840
tatgaagctc acctttggga taatagctgt cggaggagg gccagacgcg aagggacgc     900 cagggagggt acgataagga agagaaagcc gcacgcgcct atgaccttgc cgcgctaaaa    960
tattgggggc ccactacaac gactaacttc cccgtaagca attatgagaa ggaattggag   1020
gaaatgaaac atatgacccg ccaggagttc gtcgcctctc tgcgccgaaa aagttctgga   1080
tttagccgcg gcgcatcgat ctacaggggg gttacgcgcc accatcagca cggccgttgg   1140
caggctagga taggtcgtgt ggctggcaac aaggaccttt acttggggac gttctctacg   1200
caggaggaag cggccgaggc gtacgacatt gcggctatca agtttagggg tctcaacgct   1260
gtcaccaatt ttgatatgag ccgatatgat gtgaagagca tcctcgacag ttccgccctg   1320
ccaatcggtt ctgcagcgaa gaggctcaag gaggccgagg cagccgctag cgcgcaacat   1380
cacgccggtg tggtttcgta cgacgtggga cgtatagcat ctcagctggg tgacggcggg   1440
gccctagcag cgtacggtgc acattatcat gcagccgcag ctgcagcctg gcctacaatc   1500
gcattccagc caggcgccac cgcgggactg taccacccat atgcacagcc gcttcctcgg   1560
gggtggtgta agaaagagca ggaccatgct gtaattgctg cggcccactc tctccaagag   1620
ctcaatcacc tgaaccttgg cgctggtgcg catgatttct tttccgctgg ccaggccgcg   1680
atgcacggtc tcggctccat agacaattca agtctcgaac attcaaccgg gtctaattca   1740
gtcgtgtaca atggggtggg cgacagcaac ggcggtgcag tgggaggcgg atacatgatg   1800
accatgagcg cggccgctgc aaccacaacc gctatggtgt cgcacgaaca ggtacatgcc   1860
cgggcccaag gcgatcacga tgaggcatcc aagcacgccg cgcagatggg gtacgagagc   1920
```

| | |
|---|---|
| tatctgatga acgcggaggc tgcgtatggg ggaggcagaa tgccctcctg gacacgccca | 1980 |
| agattgcata ggtggcgcag gcgccaggca gccactacaa cctggcctgc tttggccatg | 2040 |
| gctgcaagat cgtcatcggt ttctggtatg accctcaaca aattgcggac gcccacccgg | 2100 |
| cacaggggga agaaatatgc ggacatatcg aatacctaa | 2139 |

<210> SEQ ID NO 6
<211> LENGTH: 729
<212> TYPE: DNA
<213> ORGANISM: Saccharum spontaneum

<400> SEQUENCE: 6

| | |
|---|---|
| atggggacca accccgtct acaggagttg gctgccgtcg tggtcgcagc tgccgactca | 60 |
| gaaccgcggc cacgcgcgag agtggtccgc atcctggtcc acgacgcaga cgctaccgac | 120 |
| agctccagct ctgaagatga ggcaccgcct ccaccgcccc caccgcgccg tcgcgctcgc | 180 |
| ggcgggagtt cgtctgtcgg agtgcgccga catgtgatgg aaccagctgg cgcttcgtct | 240 |
| gcagtgagat tcagggggtgt gcgcaggcgt ccatggggc ggtgggcagc ggagatacgc | 300 |
| gacccgcaca gccgcaggcg cttgtggctc gggacctta ataccgccga agaggcggct | 360 |
| aacgcctatg atgcagctaa cattagattc cgcggggcta gtgccccgac caacttccca | 420 |
| gccgcgcgat actccccgcc tccggagccg gcaaagccca ttatctctct cacgccagaa | 480 |
| cccgggaagg tcattacact cccgcccgtg ccggtcaagc ccaccttccc actacaggtg | 540 |
| aaggaggaag gcggttcttg tgacggccaa gtcaagggcg cgagttctga ggttaaagca | 600 |
| ttcgctccga agcccgtatg ggagatgatc ccaagtaagc ggcagaagta cccagggtgc | 660 |
| gcggacggat cgggcctccg cgccatccac gcggcttcca tctacgtgga ggaagtgggc | 720 |
| ggtgcgtaa | 729 |

<210> SEQ ID NO 7
<211> LENGTH: 870
<212> TYPE: DNA
<213> ORGANISM: Setaria italica

<400> SEQUENCE: 7

| | |
|---|---|
| atggaggacg ccaccaatgc acatttgtat gctcacgccc acctgcaccg gtccaaaagg | 60 |
| ccatcccctg cagcgtttaa agaggaagac ggcgactgcg acgcactcca caagggtgcc | 120 |
| aggtaccgag gcgttagacg ccggccatgg gggcgtttcg ccgcggagat ccgcgatccg | 180 |
| gcttcccgcg agaggcggtg gttgggcaca ttcgacacgg ctgagcaagc cgcttgcgct | 240 |
| tatgatgtcg cggcacgcgc catgcggggg tcgaaggcta ggacgaattt cccggtgcac | 300 |
| gcggcagcgg gattctggcc gtggggcgcg cctccccagc ccgctcatac cctcaacccg | 360 |
| tttctactgc ataatctaat tatgtcatct agccaccatg gctttcgtct cctgcatcaa | 420 |
| gcgggccacg gccacgtggt caattcgtcc gctccgtcca aacctccagc tccggttgcc | 480 |
| gctgcaatac ccgctccgag cccggtagcc ccgcccccgt cggaccttga cgatgaggac | 540 |
| gtcgacgatt gggccgggct tatgcggggc gagcctgctg acgccggact ccttcaggac | 600 |
| gccttgcatg ggttctaccc cgctgggacg aggccacgtg gcggagcctc acggtcgctg | 660 |
| agtgcatccg gagcggacgc acgcgccgca gcggccgacg tcccggttaa gcaagaacgc | 720 |
| tatgatgcct ttgtggacat cgatggagag gaaggcggtg aatacccat gatgccgcag | 780 |
| ggccttctag gtgacgtaat acaataccct gctttcatgg aagtagttgc agctccgtca | 840 |

```
gcaccgacac gtagagggcg ctggggttaa                                      870
```

<210> SEQ ID NO 8
<211> LENGTH: 1011
<212> TYPE: DNA
<213> ORGANISM: Oryza longistaminata

<400> SEQUENCE: 8

```
atgatgatga tgtcgggcag gccctctgga ggtgctggtg ggggcaggta cccgttcacg        60
gcgagccagt ggcaagagct tgaacaccag gcactgatct acaaatacat ggccagcgga       120
acaccgattc catcagacct gatcttgcca ctgcgcagat cctttctcct ggactcagcc       180
ctggctacgt ctccgtccct ggcctttcct ccacaaccgt ccctggggtg ggggtgcttc       240
gggatgggct ttggtcggaa agcggaagat ccagagccgg ggcgctgtag gcggactgac       300
gggaagaaat ggagatgcag caaggaagca tatcccgatt ctaagtactg cgagaagcac       360
atgcacaggg ggaagaaccg atctcgtaaa ccggtggaga tgagcctggc gacgcctcca       420
gccccgtcat ccagtgcaac ctcagccgca cttacgccgt cttccgagaa ccatctcaag       480
acgcgtccac ggacaccaga gcttgcgcca agcaaaccta ctatctcact tttcccgcca       540
ggctccagaa gggccccgaa tcagccccct atgcagcatc caaacagccc aaagccgatc       600
ccaactacgc ttaccgaaat ccctcccaat cccccagctt cgccatccc cactacgagg        660
cgactacatc acacacgcaa cgaacgcagg gaacgcctca cctggccacc gtcgctggcc       720
ggatggccgg cggatagggg tcgctgccga cgcagacagc aacagcaaca gcaacagcaa       780
cactgtttcc tgctcggcgc ggaccttaga ttggaaaaac cagcaggcca tgatcacgcc       840
gcagctgcac agaagcccct ccggcacttt ttcgacgagt ggccgcatga aaagtcgagc       900
aagggctcct ggatggggct tgagggagag acgcaactgt caatgtctat tccaatggca       960
gccaacgatc tccctatcac gacaaccagc aggtatcata acgatgacta a              1011
```

<210> SEQ ID NO 9
<211> LENGTH: 1008
<212> TYPE: DNA
<213> ORGANISM: Saccharum spontaneum

<400> SEQUENCE: 9

```
atgatgcttt caggccacgg tggaggtcgt cggttgttca ccgcctccca atggcaggag        60
ctcgagcacc aggctctaat ctttaaatac atggcgtccg gcgcgccagt accacacgac       120
ttggtcctgc cactgaggtt ggcaacgggg gtcgatactg cccctcact cgccttccct        180
ccccagcact ccccagtct tgcttactgg ggatgctacg gcgctggggc cccatttggc        240
cgtaaggctg aagatccaga gccaggtcgc tgtcgccgta cagatggtaa aaagtggcgc       300
tgcagccgcg aagcgcacgg agagagtaag tattgcgaga agcatattca caggggcaag       360
tctagatcac ggaagccagt ggaggttaca tcctcagcga ctagtccagc ggccgcggcc       420
taccgaccct cagcactttc gatttctccg cccagagctg ccgatgcgcc tccacctagc       480
ctaggccatc cgcaacagca tctaaggcat ggcgcctcga gtgctgccgc gcgagcacca       540
gcccaggcga ctgccggggg tgctctccag ctccacctgg acgcgagttt gcatgctgcc       600
agcccccctc cctcctacca ccgttacgcc cactcacatg ctcactacac aacgccaacg       660
ccaacaccga ccccatccct cttcccaggg ggtggcgggg gatacgggta cgactatggg       720
caatcaaagg aactgaggga ggcagagctc cgcaggcgcc atttccatac actaggagca       780
gaccttttctc tcgacaaacc tctccctctt gccgcaacgg gctctgacgc ggccgctgca       840
```

| | |
|---|---|
| gagaagccac ttaggcggtt tttcgatgag tggccacgcg agagcggcga cactcggcca | 900 |
| agctgggccg gcgcggaaga tgcgacgcaa ctcagcatct cgattcccgc tgcatcccct | 960 |
| agtgacctgg cagcctctgc tgcggccaga tatcacaacg gggagtaa | 1008 |

<210> SEQ ID NO 10
<211> LENGTH: 1092
<212> TYPE: DNA
<213> ORGANISM: Saccharum spontaneum

<400> SEQUENCE: 10

| | |
|---|---|
| atgggggggcc cagacggtga cggtgatggt gggccccacc atcaatacca ctatcaggca | 60 |
| ctgctcgcgg ctgtacagaa tccatcccag ggcctccatc cattcccact cccgtttcac | 120 |
| ctgccactgc acgctggagc gggggcaggg gctccagccg cgggccccgg cgctgatgct | 180 |
| gacgcctcaa gtacgcataa cgtccacgcg gcccctcata gccaacctcc acgtggtttt | 240 |
| acagattgga gcccgagcaa ttcggcgttc gctgcagtgg ctgcacagcc cgcaccggca | 300 |
| acgacaaaca cgcccctgca ttacaacctc tctcagccct acccctttg gactcactac | 360 |
| atgttgaata aaaatgtgtc ttgctccacg taccctaccc aacatgagga aaaccccaac | 420 |
| cccctccgac acacgcatat tcctgaggaa atccacatc ccttgcgcca tacacatata | 480 |
| ccagacaagg atagcgggtg cgcctcctca ctggggttcg atagtttcac cacaatgagc | 540 |
| ctggggccga atatctgtgc tcatatgacc cccatggaag gctccatctc cgccaaggag | 600 |
| cctgaaaact cagaggatct gcccgcagtt gtcaggagtt cagatgagat ggacaccaga | 660 |
| aatagcgggg aaatacatag ggacacggtc ggcccactgc ctgagtcaaa acagtcccac | 720 |
| gagtcttgtg cctcaaagtt caatagtggt gaataccaag tgatcctccg caaagagctc | 780 |
| acaaaaagcg acgttgctaa cagtggacgg atagttcttc ccaaaaagga tgccgaggca | 840 |
| gggctgcctc cattggttca aggtgacccg cttattctgc aaatggacga tatggtgcta | 900 |
| ccgatcattt ggaagttcaa atacaggttc tggcccaata acaagtcgag gatgtacata | 960 |
| ctcgaggcgg ccggtgaatt cgttaaaacc cacggactcc aggctgggga cgcattgatc | 1020 |
| atatataaga actctgagcc aggaaagttt atcattcgcg gagaaaagag cattcaacag | 1080 |
| acgaacccat aa | 1092 |

<210> SEQ ID NO 11
<211> LENGTH: 1050
<212> TYPE: DNA
<213> ORGANISM: Brassica oleracea

<400> SEQUENCE: 11

| | |
|---|---|
| atggataact cctcccttt ctcttcgtct aatgccaaca gtgtgcaaga gctgagcatg | 60 |
| gacctcaata agaaccgctc gcacttctcc atggcgcaac cgcaacacct cctgccgcct | 120 |
| tactcatacg tggcctgtcc agtgctggac cagactggcg ccatgaacca ccagccgttg | 180 |
| cattcttcag acgccttccc gcagatccca gtggtccaga ctgggggaga atttggctat | 240 |
| cttgtttgca agccagggt ccggcaggag cgcggtggat tcttgaccc gcacagcacg | 300 |
| aaaatggcga gaataaatag gagaaaagct atgatccgca gtcggaataa ctcatacctc | 360 |
| aattctagct ccaatgagct agtggactct agacgccagg tggctctcac catgaagaac | 420 |
| aatgcggaaa tagccgcgcg aaaagatttt tatcgtttct ccagctttga caataagaaa | 480 |
| ttgagggtgc tcctagtcaa gcatctcaag aacagtgatg tgggctcgct cgggaggatc | 540 |

-continued

| | |
|---|---|
| gtgctcccaa agcgcgaggc tgaagggaat ttgccagagc tcagtgataa ggagggcatg | 600 |
| gttcttcaga tgagggacgt ggattccgtg caaagctggt ctttcaaata caagtattgg | 660 |
| tcgaacaata aaagccgcat gtacgtgctc gaaaataccg agagttcgt caaaaagaac | 720 |
| ggtgtgctca tggagatta tctgaccatt tatgaagacg agagcaagaa cctttacttc | 780 |
| agtatccgca agcatccaca taaacaaaac gacggccggg aggacgaaag catggaggtc | 840 |
| attgagatga acttctatga agatataatg tttgattata tacctaatgg cgaggacgat | 900 |
| tccattgcta tgctgctcgg caatctaaac gagcattatc catacccaaa cgatatcatg | 960 |
| gatctgacgg tcgacctaga ccagcatcag caagctacat cctctagccc cccggcagac | 1020 |
| catatgtctt ccaacgactt tctgtggtaa | 1050 |

<210> SEQ ID NO 12
<211> LENGTH: 1476
<212> TYPE: DNA
<213> ORGANISM: Brachypodium distachyon

<400> SEQUENCE: 12

| | |
|---|---|
| atggatatgg acgccgcgca gcaacagcac catcactatc cttggttgaa tttctcactc | 60 |
| gcccaccatt gtgggatgga agaggaagag aggggagcgg ctgcagagct tgcagcgatc | 120 |
| gcgggcgcgg caccaccccc aaagttggaa gacttcctgg gcggtggagg gggcaacggg | 180 |
| aatggcgggg gcggggcccc ggttgtgcct gccggcgccg cggctgagat gtacgaatcc | 240 |
| gagctgaagt ttctcgccgc tggcggtttt cttggatccg gagggacagg tacgtcgccg | 300 |
| gctgcaccgc ctccagtggt cgcactgaa gagcaggcag ccgaggccaa gttggccctg | 360 |
| cccttggtgg ccgcgcccgc gcctgaaacc aagaaagctg tagattcatt tggacagcgc | 420 |
| acgtctatct accgcggcgt gaccagacac aggtggaccg gacgctatga ggctcacctg | 480 |
| tgggacaata gttgtcgccg tgaagggcaa agcaggaagg ggagacaggt ataccttggc | 540 |
| gggtatgaca aggaagagaa ggccgcaaga gcctatgatc ttgccgcttt gaagtactgg | 600 |
| ggcgcaagta cgaccacgaa cttttccggtt gccgactacg agaacgagct cgaagagatg | 660 |
| aagcacatga ccaggcagga gttttgtcgcc agccttagac gcaaaagctc gggcttctcc | 720 |
| aggggcgcat ccatttacag gggagtgacg cgccaccatc agcatggccg atggcaggca | 780 |
| cgcatcggta gggtggccgg caacaaggat ctctatctcg gaacattctc aactgaggaa | 840 |
| gaggccgcag aagcttacga tattgccgca attaaattta gagggctgaa tgcagttact | 900 |
| aactttgaaa tcgggcggta caacgtggag agcatctcat cttcgaacct accaatcggg | 960 |
| accgcttccg gggccaacag aggctcgaag tgcgctctag agcctacccc cgtgataagc | 1020 |
| gatgttgatg cccatctat cgcaccgcac tccttggcct tcacagcctt gcccatgaag | 1080 |
| tacaaccaac atgaaaatga ctacctcagc tttctcgcga tgcagcatca ccagcaaggg | 1140 |
| aatctacagg gcctgggtta tggtctctac tcttcggggg ttaacctgga cttcgcgaac | 1200 |
| gctcataatg cggctacgat gacggctgcc caatgttatg gaaacggtgg cggttccctg | 1260 |
| catcaccaac agcaacagga gcaagaccat caccaacagc aacagcaaca gcaagaccag | 1320 |
| gagcagaact caaatgggtg ccccagctca gtcccattcg cgacccccat ggcattctcg | 1380 |
| ggtggaacgt atgaatcatc cgttaccccg agccccttg gctactatag cccgaacatg | 1440 |
| gctgcctttc agaccccaat cttcggtatg gaataa | 1476 |

<210> SEQ ID NO 13
<211> LENGTH: 1395

```
<212> TYPE: DNA
<213> ORGANISM: Leersia perrieri

<400> SEQUENCE: 13
atggatatgg acatgagctc cgcttaccct catcactggt tgtctttctc actctccaac      60
aataactatc atcacggact gctcgaggct ctatccacga gctccgcgcc gccactggac     120
ggagcagccg aggaagctcc aaagatggaa gacttcttgg gaggggtggg aggggtagc     180
gccgcgcccg ccgcggctcc ggaggaccag ctgggctgtg gtggagaact gggctccatt     240
gcggcaggct ttatgaggcg ttatcctaca ccggacgaga accctggggg cgtgactata     300
gcgatggcta cagatgccgt cgaggcagat ccagcacgca ggacggctga gacgttcggt     360
cagcgaacca gtatttatag aggcgttact agacatcgat ggactggacg ctacgaggct     420
cacctctggg ataactcctg cagacgcgag ggccaatccc gcaagggtcg ccagggaggt     480
tacgataagg aggaaaaagc ggcaagagcc tatgatctcg ctgcactcaa gtactggggc     540
ccgaccacta ccacgaactt cccagtggcg aattatgaaa aggagttgga agagatgaag     600
agcatgaccc gccaggagtt cattgcgtcg ctcaggcgca agtcctcggg cttctctagg     660
ggcgcctcaa tttatagggg cgtaacgaga catcaccaac acgggaggtg gcaagcgagg     720
atcggacgcg ttgccggcaa caaggatctg tacttgggga ccttctcgac acaggaagag     780
gctgcagagg cctacgacat cgcggcaatt aaattcagag gactgaatgc tgtcaccaac     840
tttgacatgt cgcggtacga cgttgactct atacttaatt ctgacttgcc tgtcggtggc     900
ggggcggctt cagcagcgac gagagcggcc aagtttccaa cgacccatc cctccctccc      960
cctcacggcg caggcgcttc ggccgctatg acaccctctg aaaaggacta ctggagcttg    1020
cttgctctcc actatcagca acagcaacag caacagcaac agttcccggc ctccgctttc    1080
gacacatacg gttgctcctc gggagtcaat gtagatttca cgatgggcac atcgagtcat    1140
tcagggtcta attccagctc ctcatccgct atgtggggta ctgcagccgc tatgggtcag    1200
caagattcct caaaccgaca gagtaattcg tattcctctc atcacaatat tccgtacgcg    1260
tccgcagcgg ctgccgctgc catggcgtcg ggctctgccg gctatgaagg ctctacgggg    1320
aacaatggca cttgggttgc cagtaacacc tcaacagccc cgcacttcta caactatttg    1380
ttcggcatgg agtaa                                                     1395

<210> SEQ ID NO 14
<211> LENGTH: 966
<212> TYPE: DNA
<213> ORGANISM: Panicum hallii

<400> SEQUENCE: 14
atggcgccct gcggcgatgg acgtgatgac gattggtatc agtacggcct cgacgatttc      60
cctccgctct gcagcgcgcc tccaccgctt gcactgcttc gcagcccgta cttcagcaac     120
cagttgccaa gggtccccgt cgatggagcg acgtcgggt tggacgatgc cctgctcctg     180
ccgttgggg atatcgacct ggaagcgttt gacagcgcgg acgagcataa gatgatccca     240
cctgccggtc agcatacagt gggacaggac tatgcgggg tggatgtcgt tcatgaagat     300
cagaaaccga tggcaatcgc agactccttc gccctaggg cgaacgctct tgagctcacc     360
atgtcgcggc acggcgagca tcaaaagtca tctagcgtgg cggccgctct cgtcccgcca     420
ccgccacccc cgctccccag gccgcgcggg cgtcgctccg tcgatcaccg gtccgctcca     480
gcgcacggaa agactcgcct cgatcacatc gggttcgacg agctccggaa gtacttctac     540
```

```
atgccaatca cgcgcgctgc ccgggagttg aacgtgggac tcacggtgct gaaaaagcgt    600
tgtcgggaac tcggcattgc gcgctggccc caccgtaaaa tgaaaagtct caagtcgctg    660
atcctaaatg tacaggaaat gggaacgggc atgaacccgg ccgcagtcca gcatgagctc    720
gcagcgcttg agacctattg tgccctgatg gaggaaaacc cggccattga actgaccgag    780
cgcaccaaga aactccgtca agcatgcttc aaggagtctt acaagagacg gagagctgcg    840
gccgtcaatg tcatggatag aattttctct ttcgatgacc ataaatatag gcatccgctt    900
cgaccaccgc ctccaccgtc atctgctgaa agacacggcc atggctcttc atttctcggc    960
tactaa                                                               966

<210> SEQ ID NO 15
<211> LENGTH: 1875
<212> TYPE: DNA
<213> ORGANISM: Saccharum spontaneum

<400> SEQUENCE: 15
atggcggccg cagccggtag atggtgggct gttgtgttgg ccgtcgccgt gctccttggg     60
ccaggcagag tggttgcaaa cacggaaggc gacgcgctct acagcctaag gcaatccttg    120
aaagacacca acaatgtctt gcaatcctgg gatccaacgt tggtcaaccc ctgcacctgg    180
ttccatgtga cttgcaacaa tgacaactcg gttatcaggg tggacctggg gaatgcccaa    240
cttagtggtg ttccttgtcc caactgggc cagcttaaga acttgcaata tcttgaactg    300
tacagcaaca atatatccgg aacaatcccc ccggagctcg ggaacttgac gaacctcgtc    360
tcgttggacc tgtatatgaa taacttctcg ggcattatac cggactcctt gggcaacctt    420
ctcaagctca gattcctccg actcaataac aattcgcttg ttggccagat acctgtctct    480
ctgactaaca ttagcacact gcaggtgctc gatctaagta taacaatctt gtcagggcag    540
gtgccctcca ccggaagctt ctcccttttt acccctattt cttcgccaa caatccattc    600 ctgtgcggcc ctgggactac aaaaccctgt ccggggggccc caccttcag tccccgcct    660 ccgttcaacc caccgagccc gccaacacag agtacagggg ccagtagcac gggtgccatc    720 gcaggggggcg tggccgctgg ggccgcgctt gtatttgccg ttccagccat cgcgttcgcc    780
atgtggcgca gacgtaaacc agaagagcac ttctttgatg ttcccgccga agaggatcca    840
gaggtgcacc tcgggcaatt gaaaagtttt ccttgagag agcttcaagt tgccacggat    900
aatttcagca acaagaacat cctcggtcgg ggaggcttcg gcaaggtcta aaggggagg    960 ctcgcagacg ggtcgctggt tgcagtgaag aggctgaagg aagagagaac tcctgggggc   1020
gaattgcagt tccagaccga ggttgagatg ataagcatgg ccgttcaccg caatctcctg   1080
cggctacggg gattctgcat gacacctacc gagaggctgt tggtgtaccc atacatggcg   1140
aacggttctg ttgcaagccg tttgcgggag cgccagcccct cagagccccc tcttcagtgg   1200
gagactcggc gccggatcgc ccttgggagc gcccggggcc tttcctacct tcacgatcac   1260
tgcgatccca agattatcca tagagacgtt aaggccgcga acatcctcct ggacgaggac   1320
ttcgaagcgg ttgtgggaga cttttggcctc gccaagctga tggattacaa ggatacacac   1380
gtcacgaccg ctgtgcgggg taccataggc acattgcac cagagtacct gtctacaggc   1440
aagagtagcg aaaagacaga tgtatttggg tatggaataa tgctccttga actcattaca   1500
ggccaaaggg cgttcgacct ggcccgccta gcgaacgacg atgacgtaat gttgctagat   1560
tgggtgaagg gtcttctgaa ggagaagaaa gtggaaatgc ttgttgaccc tgatcttcag   1620
aacgcttacg aagagatcga agtggaaaac ctgattcaag ttgctctttt gtgtacacag   1680
```

| | |
|---|---:|
| ggttccccgc tcgaccgacc taaaatgtca gaggtagtcc ggatgctgga gggagacggg | 1740 |
| ctcgccgagc ggtgggatga gtggcaaaaa gtcgaggtgg ttaggcagga agccgaatcg | 1800 |
| gcaccgctaa ggaacgactg gatcgtagat agtacttaca acctcagggc tgtggagctc | 1860 |
| agtggtccac gttaa | 1875 |

<210> SEQ ID NO 16
<211> LENGTH: 1896
<212> TYPE: DNA
<213> ORGANISM: Setaria italica

<400> SEQUENCE: 16

| | |
|---|---:|
| atggcggccg cagccggtgc aactcgtcgg cgttgggccg tctgggccct gctacttctg | 60 |
| aggctgctcc ttcatccagc ggctagagtg ctggcgaaca cggaaggaga cgcactgcat | 120 |
| agtctgagga ccaacttgaa cgatccgaac aatgtgttgc aatcatggga ccccacsctg | 180 |
| gttaatcctt gcacctggtt ccacgtgact tgcaacaatg acaactccgt tattagggtc | 240 |
| gatctcggta atgctgcact gagcgggaca ttggtgccgc agttgggaca gcttaaaaac | 300 |
| ctgcaatacc tagagctata ctccaactcc atttcaggga ccattccgtc agagctcggg | 360 |
| aatctaacca atttggtatc gctggatcta tacctgaata actttaccgg cccgatcccg | 420 |
| gacagcctgg gcaacctcct taagcttcgt ttcctgagac ttaacaataa ctctctgtct | 480 |
| ggctcgatac caaagtcgct tacagctata accgcgctgc aggtgctcga tctctccaac | 540 |
| aataacctca gcggcgaggt gcctagtact ggttctttct cactcttcac gccgatcagt | 600 |
| tttgcgaata acccaaacct gtgtgggccg ggcacaacta aaccatgccc cggtgctccc | 660 |
| ccattctccc caccgccacc ctataaccca cctaccccag tccaggctgg ctcaagctcc | 720 |
| tcgtccaccg gtgcgatcgc cggggagtg gccgctggag ccgcgctgct cttcgcggtc | 780 |
| cctgcaatag gattcgccta ttggcgtagg cgaaaacctc aagagcatt ctttgacgtt | 840 |
| ccagctgaag aggatccgga ggtccatctt ggccagctca gcgctttttc actccgcgag | 900 |
| ctacaggtcg ctactgacgg attcagtaat aagaatatcc ttggaagggg aggctttggg | 960 |
| aaggtttaca agggtaggct ggccgacgga actttggttg ccgtcaagcg actcaaggag | 1020 |
| gaacgcactc ccggaggcga gttgcagttc cagacagaag ttgaaatgat tagcatggcg | 1080 |
| gtccaccgga acctgctccg cttgcgcggg ttctgcatga ccccgactga gcgtctcctg | 1140 |
| gtttatccgt atatggcgaa cggctcagtg gcctctcgcc ttcgcgagcg gccggagtcc | 1200 |
| gaaccgcctc tagactggca gacccgcagg cgcattgcct tgggctcagc taggggcttg | 1260 |
| tcctatctcc acgatcattg cgacccaaaa atcatacacc gcgacgtgaa agcggctaat | 1320 |
| atactgttgg acgaggactt tgaggcgta gtcggggact tcggactggc caagctgatg | 1380 |
| gattataagg acacccacgt tacaaccgct gtgcgcggta caatcggcca catagcaccc | 1440 |
| gaatatctat cgacgggtaa aagcagtgag aaaaccgatg tcttcggata cgggatcatg | 1500 |
| ctgctcgagc ttataacggg ccagagagct ttcgatctgg ctcggcttgc taatgatgac | 1560 |
| gatgttatgc tgctagattg ggttaaaggt cttctgaagg aaaagaggct agagagtctt | 1620 |
| gtcgacgagg atctccagca taattatatt gactggagg tggagagcct catccaggtc | 1680 |
| gccctgctat gcacgcagtc aagcccaatg gagaggccca agatgtctga ggtcgtaagg | 1740 |
| atgctggagg gggatggcct ggcagaaagg tgggaggaat ggcaaaaggt agaggtagtg | 1800 |
| aggcaagagg tcgagctagg cccacaccgg acgtcggaat ggatccttga ctctaccgat | 1860 |

```
aacctccacg cggtcgagct gagcggccct aggtaa                              1896
```

<210> SEQ ID NO 17
<211> LENGTH: 1071
<212> TYPE: DNA
<213> ORGANISM: Saccharum spontaneum

<400> SEQUENCE: 17

```
atggaggaaa tcacacacca ttttggagtt gctgcgtctt cacacagtca cggacatggg    60
caacaccatc acccatgggc gtcgagcctg tcggcagtgg tcgcgccacc gccacaacag   120
ccaccctccg ctggcctgcc actgaccttg aacacggtgg cagcgactgg caactcaggc   180
gcctccggta atcctgtgct gcagctcgcg aatggcggat ccctgcttga tgcgtgcgtc   240
aatgtcaagg ctaagggaga gccatccagc tcttccccgt acgctggaga tcttgaagcg   300
atcaaagcga aaatcataag ccatccccat tattactcac tgctcgctgc gtacctcgaa   360
tgtaagaaag taggcgctcc tccagaggtg tctgcacgcc tgacggctat ggcccaagag   420
ctcgaggcca gacagaggac cgcacttggg ggcttgggcg cggaacgga acctgagttg    480
gaccagttca tggaagccta tcatgaaatg cttgtaaagt ttcgagagga acttacccgg   540
cccctgcagg aagcaatgga gtttatgcgc cgggtcgagt ctcagctcaa cagcctctcc   600
atctccggcc gttcgcttag gaacatcctt tcctcgggca gctctgaaga ggaccaagag   660
ggttcgggcg gagaaacgga actgccagaa gtggacgtcc atggcgtcga ccaggagctg   720
aagcaccatc tgcttaagaa atactctggg tacctgtcga gcctgaagca ggaactgagt   780
aagaaaaaga aaagggcaa gcttccaaag gaagcaagac aacagctgtt gtcttggtgg    840
gacctccact ataaatggcc ttatcccagc gagacacaga agtggcgtt ggcagagtcg     900
acaggtctcg atcttaagca gataaacaat tggtttataa accagcggaa gagacactgg   960
aaaccatccg aagagatgca tcacctgatg atggatggat accacaccac taatgccttt  1020
tacatggacg tcacttcat caacgacggt gggctttaca gattgggcta a             1071
```

<210> SEQ ID NO 18
<211> LENGTH: 981
<212> TYPE: DNA
<213> ORGANISM: Saccharum spontaneum

<400> SEQUENCE: 18

```
atggcggccg caatcgatat gtacaagtat tttaatgccc accaaatcgc atcgtccagc    60
cccagcgatc aggaactggc gaaagccctg gagccattca tcacaagcgc atcctctagc   120
ccctaccaca ggtatagctc ctcgccatcc atgtctcaag actcatacat gcccacccct   180
tcctatacct ccttcagtac gtctccactc ccgaccccgg ctgcggcaac ctcgagctct   240
tcccctttct cccaactgcc acctctttat tcctctccat atgctgcacc gggcatggca   300
gggccaatgg gcctaaacca gctcgggcct gcccagatcc agcaaattca ggcccaattt   360
atgtttcaac agcaacagcg aggtttgcac gctgcctttc taggcccgcg cgctcaacca   420
atgaagcaat ccggcagccc cccgctggca ccggcgcagt ctaagctgta ccggggcgtt   480
cgccagagc attggggaaa atgggtcgct gagatacggc tacccaagaa caggacgagg     540
ctttggctcg gcaccttcga caccgcggag gatgccgctt tggcttacga caaagccgct   600
ttccgcctcc gtggggatat ggccaggctg aatttcccgg ccctacgtag ggacggcgcc   660
catcttgccg gccacttca cgcgagcgta gatgccaaac ttaccgccat atgccagtcc   720
ctcgcagggt ccaagaacgg ttccagcggc gatgaatccg ccgctagccc cccagactcc   780
```
cccaagtgct ctgcaagcac agaaggcgag ggtgaggaag agagtggatc ggcaggttcg    840
cccccatcgc caactctagc gccgcctgtc cctgagatgg ccaagctcga ttttactgag    900
gcaccgtggg atgaaacgga acttttcac ctaaggaaat accctcttg ggagattgac    960 tgggacagca tcctttcgta a    981

<210> SEQ ID NO 19
<211> LENGTH: 966
<212> TYPE: DNA
<213> ORGANISM: Brassica napus

<400> SEQUENCE: 19
atggaggccg caatgaactt gaactcttcg cgtactttcc aacagcccga cagctttggg    60
ggaggcggag agcttatgga agcgcttctc cccttcatca aatccgtcag cgacagcccg    120
tctgcctcag cctcagcctt tataaacccg gcagcgtctg ccttcccct ccccaccttt    180 cgcgattaca accccgaaca ttatctcaca cagccgttcc cttatggcag tgatctccag    240
caaactggta gcctgatagg gctcaataac ctttcgtcat ctcaaattca tcaaatccag    300
agccagatac accataacca cccgctcccg cctacccgca gtaatcttaa cctcagtccg    360
aagccactgt tgatgaagca accgggcgtt gcaggctcct gctttgccta cggggccccg    420
ccaaaacccg ccaagctcta tcgcggggtt cgccagagac attggggcaa gtgggtggct    480
gaaattaggc taccccggaa tagaacgaga ctctggcttg cacctttga cacggccgag    540 gaagccgcac tagcctatga tactgccgct tttaagctcc gaggagactt cgcgcgcctc    600
aattttccta acctccgaca tgatgggagt agaattggcg gagaattcgg tgagtacaaa    660
ccacttcact ccacagtaga tgccaaactt gaggccatat gcaagtccat ggccgaaacg    720
gagaagcagg agaagaccac gaaggcatcc aagaaacggg catcaaccgc ggccgtcaag    780
gcagaggaaa acagcaacag catcggtgag tcaccccaa tgactgaact tgtggagagc    840
gctggctcta gcccgctgtc tgaattgact ttcgctgacg cggaggaaca gccccaatgg    900
aacgagacat tcgccttgga gaaatacca agttacgaaa ttgactggga tagcatccta    960
ccataa    966

<210> SEQ ID NO 20
<211> LENGTH: 954
<212> TYPE: DNA
<213> ORGANISM: Panicum hallii

<400> SEQUENCE: 20
atggcggcca acgtcggtgg aaagtctgtt ggtggcgggg ccggcggagg tggcacaggc    60
ggagcggtta cagcgtgtag agcctccggc agccgctgga caccaacacc agagcagatc    120
aggatcctga agagctata ctatgggtgc gggattaggt cacccaactc agagcagatc    180
cagcgcatca ccgccatgct tcgtcaacac ggcaagatcg aggggaaaaa cgttttctat    240
tggtttcaga accataaagc gagggagcgc cagaagcgta gacttactaa cctggacgtc    300
aacgtaccgg cagccgtgga cgcgtctcac ctgggcgctc tttcactcag ttcgcctagc    360
ggcgctgcgc caccttcatc tccactgggc ctgtatccaa gtaatggcgg gggcagcacc    420
ctccagctcg atacgtcgtc tgattggggg agcgctaccg ctatggcgac tgaaacgtgc    480
ttcctgcagg attacatggg ggtaatgagg tccaccggcg gtcaccatgg agttccgcc    540 ggagcagcgg tgtcgccttg ggcctgtttg tctagctccg acagttgggc ggccgtggcc    600

```
cctacgacta caagggcccc tgagacgctc ccattgttcc caaccggcga ttcgtcacac    660
ccacagagac cgaggcacgg ggccccagcg cccaccggag atgctatcag gggagggtcc    720
tcaagtggtt atctccccac gctaccgttc tggggtgcag cggccaccgc ggccacgaca    780
actacaagcg taacaatcca gcaacagcat caccaactcc tacagctcca ggagcagtac    840
tcgttcaata caactacctc tcaacctccg agccaggacg cgtcggctgc cacagcctcg    900
ctagagctct ctttgagcag ttggtgcagt ccgtacactg cggggacaat gtaa           954
```

<210> SEQ ID NO 21
<211> LENGTH: 223
<212> TYPE: PRT
<213> ORGANISM: Saccharum hybrid

<400> SEQUENCE: 21

Met Gly Arg Glu Arg Ile Ala Ile Arg Arg Ile Asp Asn Leu Ala Ala
1               5                   10                  15

Arg Gln Val Thr Phe Ser Lys Arg Arg Arg Gly Leu Phe Lys Lys Ala
            20                  25                  30

Glu Glu Leu Ser Ile Leu Cys Asp Ala Glu Val Gly Leu Val Val Phe
        35                  40                  45

Ser Ala Thr Gly Lys Leu Phe His Phe Ala Ser Thr Ser Met Lys Gln
    50                  55                  60

Val Ile Asp Arg Tyr Asp Ser His Ser Lys Asn Leu Gln Lys Ser Glu
65                  70                  75                  80

Ala Leu Ser Gln Leu Gln Ser His Ile Asp Asp Gly Thr Cys Ser Arg
                85                  90                  95

Leu Lys Glu Glu Leu Ala Glu Thr Ser Leu Lys Leu Arg Gln Met Arg
            100                 105                 110

Gly Glu Glu Leu Gln Arg Leu Ser Val Gln Gln Leu Gln Glu Leu Glu
        115                 120                 125

Lys Thr Leu Glu Ser Gly Leu Gly Ser Val Leu Lys Thr Lys Ser Gln
    130                 135                 140

Lys Ile Leu Asp Glu Ile Ser Gly Leu Glu Arg Lys Arg Met Glu Leu
145                 150                 155                 160

Ile Glu Glu Asn Ser Arg Leu Lys Glu Gln Val Thr His Met Ala Arg
                165                 170                 175

Met Glu Thr Gln Leu Gly Val Ser Glu Ile Val Tyr Glu Glu Gly
            180                 185                 190

Gln Ser Ser Glu Ser Val Thr Asn Thr Ser Tyr Pro Arg Pro Ser Thr
        195                 200                 205

Asp Thr Asp Asp Cys Ser Asp Thr Ser Leu Arg Leu Gly Leu Pro
    210                 215                 220

<210> SEQ ID NO 22
<211> LENGTH: 264
<212> TYPE: PRT
<213> ORGANISM: Brassica napus

<400> SEQUENCE: 22

Met Gly Arg Gly Lys Ile Glu Ile Lys Arg Ile Glu Asn Ala Asn Ser
1               5                   10                  15

Arg Gln Val Thr Phe Ser Lys Arg Arg Ala Gly Leu Leu Lys Lys Ala
            20                  25                  30

His Glu Leu Ser Val Leu Cys Asp Ala Glu Val Ala Val Ile Val Phe
        35                  40                  45

```
Ser Lys Ser Gly Lys Leu Phe Glu Phe Ser Ser Thr Arg Cys Met Lys
    50                  55                  60

Lys Thr Leu Leu Arg Tyr Gly Asn Tyr Gln Ile Ser Ser Asp Val Pro
65                  70                  75                  80

Gly Ile Asn Arg Lys Ala Glu Asn Gln Glu Cys Thr Glu Val Asp Leu
                85                  90                  95

Leu Lys Asp Glu Ile Ser Met Leu Gln Glu Lys His Leu Gln Met Gln
            100                 105                 110

Gly Lys Arg Leu Asn Leu Leu Ser Leu Lys Glu Leu Gln His Leu Glu
        115                 120                 125

Lys Gln Leu Asn Phe Ser Leu Ile Ser Val Arg Glu Arg Lys Glu Leu
130                 135                 140

Leu Leu Thr Lys Gln Leu Glu Glu Ser Arg Leu Lys Glu Gln Arg Ala
145                 150                 155                 160

Glu Leu Glu Asn Glu Thr Leu Arg Arg Gln Val Gln Glu Leu Arg Ser
                165                 170                 175

Phe Leu Pro Ser Ile Asn Gln His Tyr Val Pro Ser Tyr Ile Lys Cys
            180                 185                 190

Phe Ala Ile Asp Pro Lys Lys Ser Leu Leu Ser Asn Thr Cys Leu Gly
        195                 200                 205

Asp Ile Asn Cys Ser Leu Gln Asn Thr Asn Ser Asp Thr Thr Leu Gln
210                 215                 220

Leu Gly Leu Pro Gly Glu Ala His Asp Thr Arg Lys Asn Glu Gly Asp
225                 230                 235                 240

Arg Glu Ser Pro Ser Ser Asp Ser Val Thr Thr Ser Thr Thr Arg Ala
                245                 250                 255

Thr Ala Gln Arg Ile Ser Leu Val
            260

<210> SEQ ID NO 23
<211> LENGTH: 686
<212> TYPE: PRT
<213> ORGANISM: Saccharum spontaneum

<400> SEQUENCE: 23

Met Ala Ser Ala Asn Asn Trp Leu Gly Phe Ser Leu Ser Gly Gln Asp
1               5                   10                  15

Asn Pro Gln Pro Asn His Gln Asp Ser Ser Pro Ala Ala Ala Gly Ile
            20                  25                  30

Asp Ile Ser Gly Ala Ser Asp Phe Tyr Gly Leu Pro Thr Gln Gln Gly
        35                  40                  45

Ser Asp Gly His Leu Gly Val Pro Gly Leu Arg Asp Asp His Ala Ser
    50                  55                  60

Tyr Gly Ile Met Glu Ala Phe Asn Arg Val Pro Gln Glu Thr Gln Asp
65                  70                  75                  80

Trp Asn Met Arg Gly Leu Glu Tyr Asn Gly Gly Ser Glu Leu Ser
                85                  90                  95

Met Leu Val Gly Ser Ser Gly Gly Gly Gly Gly Lys Arg Ala
            100                 105                 110

Val Glu Asp Ser Glu Pro Lys Leu Glu Asp Phe Leu Gly Gly Asn Ser
        115                 120                 125

Phe Val Ser Glu Gln Asp Gln Ser Gly Gly Tyr Leu Phe Ser Gly Val
    130                 135                 140

Pro Met Ala Ser Ser Thr Asn Ser Asn Ser Gly Ser Asn Thr Met Glu
145                 150                 155                 160
```

```
Leu Ser Met Ile Lys Ser Trp Leu Arg Asn Asn Gln Val Pro Gln Pro
            165                 170                 175

Gln Pro Pro Ala Ala Pro His Gln Pro Gln Pro Glu Glu Met Ser Thr
            180                 185                 190

Asp Ala Ser Ala Ser Ser Phe Gly Cys Ser Asp Ser Met Gly Arg Asn
            195                 200                 205

Gly Thr Val Ala Ala Ala Gly Ser Ser Gln Ser Leu Ala Leu Ser Met
            210                 215                 220

Ser Thr Gly Ser His Leu Pro Met Val Val Ala Gly Gly Ala Ser
225                 230                 235                 240

Gly Ala Ala Ser Glu Ser Thr Ser Ser Glu Asn Lys Arg Ala Ser Gly
            245                 250                 255

Ala Met Asp Ser Pro Gly Ser Ala Val Glu Ala Val Pro Arg Lys Ser
            260                 265                 270

Ile Asp Thr Phe Gly Gln Arg Thr Ser Ile Tyr Arg Gly Val Thr Arg
            275                 280                 285

His Arg Trp Thr Gly Arg Tyr Glu Ala His Leu Trp Asp Asn Ser Cys
            290                 295                 300

Arg Arg Glu Gly Gln Ser Arg Lys Gly Arg Gln Val Tyr Leu Gly Gly
305                 310                 315                 320

Tyr Asp Lys Glu Asp Lys Ala Ala Arg Ala Tyr Asp Leu Ala Ala Leu
            325                 330                 335

Lys Tyr Trp Gly Thr Thr Thr Thr Asn Phe Pro Ile Ser Asn Tyr
            340                 345                 350

Glu Lys Glu Val Glu Glu Met Lys His Met Thr Arg Gln Glu Tyr Ile
            355                 360                 365

Ala Tyr Leu Arg Arg Asn Ser Ser Gly Phe Ser Arg Gly Ala Ser Lys
            370                 375                 380

Tyr Arg Gly Val Thr Arg His His Gln His Gly Arg Trp Gln Ala Arg
385                 390                 395                 400

Ile Gly Arg Val Ala Gly Asn Lys Asp Leu Tyr Leu Gly Thr Phe Ser
            405                 410                 415

Thr Glu Glu Glu Ala Ala Glu Ala Tyr Asp Ile Ala Ala Ile Lys Phe
            420                 425                 430

Arg Gly Leu Asn Ala Val Thr Asn Phe Asp Met Ser Arg Tyr Asp Val
            435                 440                 445

Lys Ser Ile Leu Glu Ser Ser Thr Leu Pro Val Gly Gly Ala Ala Arg
            450                 455                 460

Arg Leu Lys Asp Ala Val Asp His Val Glu Ala Gly Ala Thr Ile Trp
465                 470                 475                 480

Arg Ala Asp Met Asp Gly Gly Val Ile Ser Gln Leu Ala Glu Ala Gly
            485                 490                 495

Met Gly Gly Tyr Ala Ser Tyr Gly His His Gly Trp Pro Thr Ile Ala
            500                 505                 510

Phe Gln Gln Pro Ser Pro Leu Ser Val His Tyr Pro Tyr Gly Gln Pro
            515                 520                 525

Pro Ser Arg Gly Trp Cys Lys Pro Glu Gln Asp Ala Ala Val Ala Ala
            530                 535                 540

Ala Ala His Ser Leu Gln Asp Leu Gln Gln Leu His Leu Gly Ser Ala
545                 550                 555                 560

Ala Ala His Asn Phe Phe Gln Ala Ser Ser Ser Ala Val Tyr Asn
            565                 570                 575
```

```
Ser Gly Gly Ala Ala Ser Gly Gly Tyr Gln Gly Leu Gly Gly Gly
            580                 585                 590

Ser Ser Phe Leu Met Pro Ser Ser Thr Val Val Ala Ala Ala Asp Gln
595                 600                 605

Gly His Ser Ser Thr Ala Asn Gln Gly Ser Thr Cys Ser Tyr Gly Asp
        610                 615                 620

Asp His Gln Glu Gly Lys Leu Ile Gly Tyr Asp Ala Met Val Ala Ala
625                 630                 635                 640

Thr Ala Ala Ala Gly Gly Asp Pro Tyr Ala Ala Arg Ser Gly Tyr
                645                 650                 655

Gln Phe Ser Gln Gly Ser Gly Ser Thr Val Ser Ile Ala Arg Ala Asn
        660                 665                 670

Gly Tyr Ser Asn Asn Trp Ser Ser Pro Phe Asn Gly Met Gly
            675                 680                 685

<210> SEQ ID NO 24
<211> LENGTH: 484
<212> TYPE: PRT
<213> ORGANISM: Triticum urartu

<400> SEQUENCE: 24

Met Ala Ser Ala Asn Asn Trp Leu Gly Phe Ser Leu Ser Gly Gln Gly
1               5                   10                  15

Ser His Pro Gln Pro His Gln Asn Gly Ser Pro Ala Ala Ala Ala Ile
                20                  25                  30

Asp Gly Asp Phe Tyr Gly Leu Gln Ala Gln Thr Ala Pro Asp Ala His
            35                  40                  45

Leu Gly Met Ser Ser Leu Arg Ala Asp Ala Asn Tyr Gly Val Met Asp
50                  55                  60

Ala Phe Asn Gly Gly Thr Gln Glu Thr Gln Asp Trp Ala Met Arg Gly
65                  70                  75                  80

Leu Asp Tyr His Gly Gly Ser Ser Glu Leu Ser Met Leu Val Gly Ser
                85                  90                  95

Ser Gly Gly Arg Met Thr Val Asp Asp Gly Glu Ala Pro Lys Leu Glu
                100                 105                 110

Asp Phe Leu Gly Gly Asn Ser Phe Ser Asp Ala Gln Asp His Ala Gly
            115                 120                 125

Ser Tyr Leu Phe Ser Ser Gly Ser Ala Met Gly Ser Gly Ala Ala Ser
        130                 135                 140

Gly Ser His Gly Val Asp Gly Arg Gly Gly Ser Thr Ile Glu Leu Ser
145                 150                 155                 160

Met Ile Lys Thr Trp Leu Arg Asn Asp Asn Glu Ala Gln His Asp
                165                 170                 175

Gln Glu Met Ser Ala Asp Ala Ser Ala Thr Ser Tyr Ala Cys Ser Gly
            180                 185                 190

Ala Pro Gly Ser Thr Ser Asn Gly Val Gly Val Ala Ser Ser Arg Gly
        195                 200                 205

Gln Gly Leu Ala Leu Ser Met Ser Met Gly Ser Asn Ser His Pro Gln
    210                 215                 220

Met Pro Val Val Pro Ala Ala Val Gly Thr Glu Ser Thr Ser Ser Glu
225                 230                 235                 240

Asn Lys Arg Val Asp Ser Pro Ser Ala Gly Thr Ala Asp Ala Val Gln
                245                 250                 255

Arg Lys Ser Ile Asp Thr Phe Gly Gln Arg Thr Ser Ile Tyr Arg Gly
            260                 265                 270
```

Val Thr Arg His Arg Trp Thr Gly Arg Tyr Glu Ala His Leu Trp Asp
            275                 280                 285

Asn Ser Cys Arg Arg Glu Gly Gln Thr Arg Lys Gly Lys Gln Gly Gly
        290                 295                 300

Tyr Asp Lys Glu Asp Lys Ala Arg Ala Tyr Asp Leu Ala Ala Leu
305                 310                 315                 320

Lys Tyr Trp Gly Thr Thr Thr Thr Asn Ile Pro Ile Ser Thr Tyr
                325                 330                 335

Glu Lys Glu Ile Glu Glu Met Lys His Met Thr Arg Gln Glu Tyr Ile
                340                 345                 350

Ala Tyr Leu Arg Arg Asn Ser Ser Gly Phe Ser Arg Gly Ala Ser Lys
            355                 360                 365

Tyr Arg Gly Val Thr Arg His His Gln Gln Gly Arg Trp Gln Ala Arg
    370                 375                 380

Ile Gly Arg Val Ala Gly Asn Lys Asp Leu Tyr Leu Gly Thr Phe Thr
385                 390                 395                 400

Thr Glu Glu Glu Ala Glu Ala Tyr Asp Ile Ala Ala Ile Lys Phe
                405                 410                 415

Arg Gly Leu Asn Ala Val Thr Asn Phe Glu Met Ser Arg Tyr Asp Val
            420                 425                 430

Lys Ser Ile Leu Glu Gly Ser Thr Leu Pro Thr Cys Met Leu Pro Cys
    435                 440                 445

Met His Phe Thr Ala Lys Ser Asn Ser Ala Ser Glu Arg Leu Lys Ser
450                 455                 460

Ile Glu Leu Ser Thr Gly Gln Cys Thr Ile Phe Ala Asn Val Gln Lys
465                 470                 475                 480

Gln Phe Asp Thr

<210> SEQ ID NO 25
<211> LENGTH: 712
<212> TYPE: PRT
<213> ORGANISM: Panicum hallii

<400> SEQUENCE: 25

Met Ala Thr Val Asn Asn Trp Leu Ala Phe Ser Leu Ser Pro Gln Asp
1               5                   10                  15

Leu Pro Pro Ser Gln Thr Asp Ser Thr Leu Ile Ser Ala Ala Ala Thr
            20                  25                  30

Asp Glu Val Ser Gly Asp Val Cys Phe Asn Ile Pro Gln Asp Trp Gly
        35                  40                  45

Met Arg Gly Ser Glu Leu Ser Ala Leu Val Ser Glu Pro Lys Leu Glu
50                  55                  60

Asp Phe Leu Gly Gly Ile Asn Phe Ser Glu Gln His His Lys Ala Asn
65                  70                  75                  80

Leu Asn Val Ile Pro Ser Ser Ser Thr Cys Tyr Ala Ser Ser Gly
            85                  90                  95

Ala Ser Thr Gly Tyr His His Gln Leu Tyr His His Pro Ser Ser Ala
            100                 105                 110

Leu His Phe Ala Asp Ser Val Met Val Ala Ser Ala Gly Val His
        115                 120                 125

Asp Gly Gly Ala Met Leu Ser Ala Ala Ala Asn Gly Gly Ala Gly
    130                 135                 140

Ala Ala Gly Ala Asn Gly Gly Ser Ile Gly Leu Ser Met Ile Lys Asn
145                 150                 155                 160

```
Trp Leu Arg Ser Gln Pro Ala Pro Pro Gln Pro Arg Val Ala Val
                165                 170                 175

Ala Glu Gly Ala Gln Ala Ala Gln Gly Leu Ser Leu Ser Met Asn Met
            180                 185                 190

Ala Gly Thr Gln Gly Ala Gly Met Pro Leu Leu Ala Gly Glu Arg Gly
            195                 200                 205

Arg Ala Pro Glu Ser Val Ser Thr Ser Ala Gln Gly Gly Ala Val Ala
        210                 215                 220

Ala Arg Lys Glu Asp Ser Gly Ala Gly Ala Leu Val Ala Val Ser
225                 230                 235                 240

Thr Asp Thr Gly Gly Ser Gly Gly Ala Ser Ala Glu Thr Val Ala Arg
                245                 250                 255

Lys Thr Val Asp Thr Phe Gly Gln Arg Thr Ser Ile Tyr Arg Gly Val
            260                 265                 270

Thr Arg His Arg Trp Thr Gly Arg Tyr Glu Ala His Leu Trp Asp Asn
        275                 280                 285

Ser Cys Arg Arg Glu Gly Gln Thr Arg Lys Gly Arg Gln Gly Gly Tyr
    290                 295                 300

Asp Lys Glu Glu Lys Ala Ala Arg Ala Tyr Asp Leu Ala Ala Leu Lys
305                 310                 315                 320

Tyr Trp Gly Pro Thr Thr Thr Thr Asn Phe Pro Val Ser Asn Tyr Glu
                325                 330                 335

Lys Glu Leu Glu Glu Met Lys His Met Thr Arg Gln Glu Phe Val Ala
            340                 345                 350

Ser Leu Arg Arg Lys Ser Ser Gly Phe Ser Arg Gly Ala Ser Ile Tyr
        355                 360                 365

Arg Gly Val Thr Arg His His Gln His Gly Arg Trp Gln Ala Arg Ile
    370                 375                 380

Gly Arg Val Ala Gly Asn Lys Asp Leu Tyr Leu Gly Thr Phe Ser Thr
385                 390                 395                 400

Gln Glu Glu Ala Ala Glu Ala Tyr Asp Ile Ala Ala Ile Lys Phe Arg
                405                 410                 415

Gly Leu Asn Ala Val Thr Asn Phe Asp Met Ser Arg Tyr Asp Val Lys
            420                 425                 430

Ser Ile Leu Asp Ser Ser Ala Leu Pro Ile Gly Ser Ala Ala Lys Arg
        435                 440                 445

Leu Lys Glu Ala Glu Ala Ala Ser Ala Gln His His Ala Gly Val
    450                 455                 460

Val Ser Tyr Asp Val Gly Arg Ile Ala Ser Gln Leu Gly Asp Gly Gly
465                 470                 475                 480

Ala Leu Ala Ala Tyr Gly Ala His Tyr His Ala Ala Ala Ala Ala
                485                 490                 495

Trp Pro Thr Ile Ala Phe Gln Pro Gly Ala Thr Ala Gly Leu Tyr His
            500                 505                 510

Pro Tyr Ala Gln Pro Leu Pro Arg Gly Trp Cys Lys Lys Glu Gln Asp
        515                 520                 525

His Ala Val Ile Ala Ala His Ser Leu Gln Glu Leu Asn His Leu
    530                 535                 540

Asn Leu Gly Ala Gly Ala His Asp Phe Phe Ser Ala Gly Gln Ala Ala
545                 550                 555                 560

Met His Gly Leu Gly Ser Ile Asp Asn Ser Ser Leu Glu His Ser Thr
                565                 570                 575
```

```
Gly Ser Asn Ser Val Val Tyr Asn Gly Val Gly Asp Ser Asn Gly Gly
            580                 585                 590

Ala Val Gly Gly Gly Tyr Met Met Thr Met Ser Ala Ala Ala Ala Thr
            595                 600                 605

Thr Thr Ala Met Val Ser His Glu Gln Val His Ala Arg Ala Gln Gly
610                 615                 620

Asp His Asp Glu Ala Ser Lys His Ala Ala Gln Met Gly Tyr Glu Ser
625                 630                 635                 640

Tyr Leu Met Asn Ala Glu Ala Ala Tyr Gly Gly Gly Arg Met Pro Ser
                645                 650                 655

Trp Thr Arg Pro Arg Leu His Arg Trp Arg Arg Gln Ala Ala Thr
            660                 665                 670

Thr Thr Trp Pro Ala Leu Ala Met Ala Ala Arg Ser Ser Ser Val Ser
            675                 680                 685

Gly Met Thr Leu Asn Lys Leu Arg Thr Pro Thr Arg His Arg Gly Lys
            690                 695                 700

Lys Tyr Ala Asp Ile Ser Asn Thr
705                 710

<210> SEQ ID NO 26
<211> LENGTH: 242
<212> TYPE: PRT
<213> ORGANISM: Saccharum spontaneum

<400> SEQUENCE: 26

Met Gly Thr Asn Pro Arg Leu Gln Glu Leu Ala Ala Val Val Ala
1               5                   10                  15

Ala Ala Asp Ser Glu Pro Arg Pro Arg Ala Arg Val Val Arg Ile Leu
            20                  25                  30

Val His Asp Ala Asp Ala Thr Asp Ser Ser Ser Ser Glu Asp Glu Ala
            35                  40                  45

Pro Pro Pro Pro Pro Pro Arg Arg Arg Ala Arg Gly Gly Ser Ser
    50                  55                  60

Ser Val Gly Val Arg Arg His Val Met Glu Pro Ala Gly Ala Ser Ser
65                  70                  75                  80

Ala Val Arg Phe Arg Gly Val Arg Arg Pro Trp Gly Arg Trp Ala
                85                  90                  95

Ala Glu Ile Arg Asp Pro His Ser Arg Arg Arg Leu Trp Leu Gly Thr
            100                 105                 110

Phe Asn Thr Ala Glu Glu Ala Ala Asn Ala Tyr Asp Ala Ala Asn Ile
        115                 120                 125

Arg Phe Arg Gly Ala Ser Ala Pro Thr Asn Phe Pro Ala Ala Arg Tyr
    130                 135                 140

Ser Pro Pro Pro Glu Pro Ala Lys Pro Ile Ile Ser Leu Thr Pro Glu
145                 150                 155                 160

Pro Gly Lys Val Ile Thr Leu Pro Pro Val Pro Val Lys Pro Thr Phe
                165                 170                 175

Pro Leu Gln Val Lys Glu Glu Gly Gly Ser Cys Asp Gly Gln Val Lys
            180                 185                 190

Gly Ala Ser Ser Glu Val Lys Ala Phe Ala Pro Lys Pro Val Trp Glu
        195                 200                 205

Met Ile Pro Ser Lys Arg Gln Lys Tyr Pro Gly Cys Ala Asp Gly Ser
    210                 215                 220

Gly Leu Arg Ala Ile His Ala Ala Ser Ile Tyr Val Glu Glu Val Gly
225                 230                 235                 240
```

Gly Ala

<210> SEQ ID NO 27
<211> LENGTH: 289
<212> TYPE: PRT
<213> ORGANISM: Setaria italica

<400> SEQUENCE: 27

Met Glu Asp Ala Thr Asn Ala His Leu Tyr Ala His Ala His Leu His
1               5                   10                  15

Arg Ser Lys Arg Pro Ser Pro Ala Ala Phe Lys Glu Glu Asp Gly Asp
            20                  25                  30

Cys Asp Ala Leu His Lys Gly Ala Arg Tyr Arg Gly Val Arg Arg Arg
        35                  40                  45

Pro Trp Gly Arg Phe Ala Ala Glu Ile Arg Asp Pro Ala Ser Arg Glu
    50                  55                  60

Arg Arg Trp Leu Gly Thr Phe Asp Thr Ala Glu Gln Ala Ala Cys Ala
65                  70                  75                  80

Tyr Asp Val Ala Ala Arg Ala Met Arg Gly Ser Lys Ala Arg Thr Asn
                85                  90                  95

Phe Pro Val His Ala Ala Gly Phe Trp Pro Trp Gly Ala Pro Pro
            100                 105                 110

Gln Pro Ala His Thr Leu Asn Pro Phe Leu Leu His Asn Leu Ile Met
        115                 120                 125

Ser Ser Ser His His Gly Phe Arg Leu Leu His Gln Ala Gly His Gly
130                 135                 140

His Val Val Asn Ser Ser Ala Pro Ser Lys Pro Pro Ala Pro Val Ala
145                 150                 155                 160

Ala Ala Ile Pro Ala Pro Ser Pro Val Ala Pro Pro Ser Asp Leu
                165                 170                 175

Asp Asp Glu Asp Val Asp Asp Trp Ala Gly Leu Met Arg Gly Glu Pro
            180                 185                 190

Ala Asp Ala Gly Leu Leu Gln Asp Ala Leu His Gly Phe Tyr Pro Ala
        195                 200                 205

Gly Thr Arg Pro Arg Gly Gly Ala Ser Arg Ser Leu Ser Ala Ser Gly
    210                 215                 220

Ala Asp Ala Arg Ala Ala Ala Asp Val Pro Val Lys Gln Glu Arg
225                 230                 235                 240

Tyr Asp Ala Phe Val Asp Ile Asp Gly Glu Glu Gly Glu Tyr Pro
                245                 250                 255

Met Met Pro Gln Gly Leu Leu Gly Asp Val Ile Gln Tyr Pro Ala Phe
            260                 265                 270

Met Glu Val Val Ala Ala Pro Ser Ala Pro Thr Arg Arg Gly Arg Trp
        275                 280                 285

Gly

<210> SEQ ID NO 28
<211> LENGTH: 336
<212> TYPE: PRT
<213> ORGANISM: Oryza longistaminata

<400> SEQUENCE: 28

Met Met Met Met Ser Gly Arg Pro Ser Gly Gly Ala Gly Gly Arg
1               5                   10                  15

Tyr Pro Phe Thr Ala Ser Gln Trp Gln Glu Leu Glu His Gln Ala Leu

```
            20                  25                  30
Ile Tyr Lys Tyr Met Ala Ser Gly Thr Pro Ile Pro Ser Asp Leu Ile
             35                  40                  45

Leu Pro Leu Arg Arg Ser Phe Leu Leu Asp Ser Ala Leu Ala Thr Ser
 50                  55                  60

Pro Ser Leu Ala Phe Pro Pro Gln Pro Ser Leu Gly Trp Gly Cys Phe
 65                  70                  75                  80

Gly Met Gly Phe Gly Arg Lys Ala Glu Asp Pro Glu Pro Gly Arg Cys
                 85                  90                  95

Arg Arg Thr Asp Gly Lys Lys Trp Arg Cys Ser Lys Glu Ala Tyr Pro
                100                 105                 110

Asp Ser Lys Tyr Cys Glu Lys His Met His Arg Gly Lys Asn Arg Ser
            115                 120                 125

Arg Lys Pro Val Glu Met Ser Leu Ala Thr Pro Ala Pro Ser Ser
130                 135                 140

Ser Ala Thr Ser Ala Ala Leu Thr Pro Ser Ser Glu Asn His Leu Lys
145                 150                 155                 160

Thr Arg Pro Arg Thr Pro Glu Leu Ala Pro Lys Gln Thr Thr Ile Ser
                165                 170                 175

Leu Phe Pro Pro Gly Ser Arg Arg Ala Pro Asn Gln Pro Pro Met Gln
            180                 185                 190

His Pro Asn Ser Pro Lys Pro Ile Pro Thr Thr Leu Thr Glu Ile Pro
            195                 200                 205

Pro Asn Pro Pro Ala Phe Ala Ile Pro Thr Thr Arg Arg Leu His His
        210                 215                 220

Thr Arg Asn Glu Arg Arg Glu Arg Leu Thr Trp Pro Pro Ser Leu Ala
225                 230                 235                 240

Gly Trp Pro Ala Asp Arg Gly Arg Cys Arg Arg Gln Gln Gln Gln
                245                 250                 255

Gln Gln Gln Gln His Cys Phe Leu Leu Gly Ala Asp Leu Arg Leu Glu
            260                 265                 270

Lys Pro Ala Gly His Asp His Ala Ala Ala Gln Lys Pro Leu Arg
                275                 280                 285

His Phe Phe Asp Glu Trp Pro His Glu Lys Ser Ser Lys Gly Ser Trp
            290                 295                 300

Met Gly Leu Glu Gly Glu Thr Gln Leu Ser Met Ser Ile Pro Met Ala
305                 310                 315                 320

Ala Asn Asp Leu Pro Ile Thr Thr Ser Arg Tyr His Asn Asp Asp
                325                 330                 335

<210> SEQ ID NO 29
<211> LENGTH: 335
<212> TYPE: PRT
<213> ORGANISM: Saccharum spontaneum

<400> SEQUENCE: 29

Met Met Leu Ser Gly His Gly Gly Gly Arg Arg Leu Phe Thr Ala Ser
 1               5                   10                  15

Gln Trp Gln Glu Leu Glu His Gln Ala Leu Ile Phe Lys Tyr Met Ala
                20                  25                  30

Ser Gly Ala Pro Val Pro His Asp Leu Val Leu Pro Leu Arg Leu Ala
             35                  40                  45

Thr Gly Val Asp Thr Ala Pro Ser Leu Ala Phe Pro Pro Gln His Ser
 50                  55                  60
```

```
Pro Ser Leu Ala Tyr Trp Gly Cys Tyr Gly Ala Gly Ala Pro Phe Gly
 65                  70                  75                  80

Arg Lys Ala Glu Asp Pro Glu Pro Gly Arg Cys Arg Arg Thr Asp Gly
                 85                  90                  95

Lys Lys Trp Arg Cys Ser Arg Glu Ala His Gly Glu Ser Lys Tyr Cys
            100                 105                 110

Glu Lys His Ile His Arg Gly Lys Ser Arg Ser Arg Lys Pro Val Glu
        115                 120                 125

Val Thr Ser Ser Ala Thr Ser Pro Ala Ala Ala Tyr Arg Pro Ser
130                 135                 140

Ala Leu Ser Ile Ser Pro Pro Arg Ala Ala Asp Ala Pro Pro Ser
145                 150                 155                 160

Leu Gly His Pro Gln Gln His Leu Arg His Gly Ala Ser Ser Ala Ala
                165                 170                 175

Ala Arg Ala Pro Ala Gln Ala Thr Ala Gly Gly Ala Leu Gln Leu His
            180                 185                 190

Leu Asp Ala Ser Leu His Ala Ala Ser Pro Pro Ser Tyr His Arg
        195                 200                 205

Tyr Ala His Ser His Ala His Tyr Thr Thr Pro Thr Pro Thr Pro Thr
210                 215                 220

Pro Ser Leu Phe Pro Gly Gly Gly Gly Tyr Gly Tyr Asp Tyr Gly
225                 230                 235                 240

Gln Ser Lys Glu Leu Arg Glu Ala Glu Leu Arg Arg Arg His Phe His
                245                 250                 255

Thr Leu Gly Ala Asp Leu Ser Leu Asp Lys Pro Leu Pro Leu Ala Ala
            260                 265                 270

Thr Gly Ser Asp Ala Ala Ala Glu Lys Pro Leu Arg Arg Phe Phe
        275                 280                 285

Asp Glu Trp Pro Arg Glu Ser Gly Asp Thr Arg Pro Ser Trp Ala Gly
290                 295                 300

Ala Glu Asp Ala Thr Gln Leu Ser Ile Ser Ile Pro Ala Ala Ser Pro
305                 310                 315                 320

Ser Asp Leu Ala Ala Ser Ala Ala Ala Arg Tyr His Asn Gly Glu
            325                 330                 335

<210> SEQ ID NO 30
<211> LENGTH: 363
<212> TYPE: PRT
<213> ORGANISM: Saccharum spontaneum

<400> SEQUENCE: 30

Met Gly Gly Pro Asp Gly Asp Gly Asp Gly Pro His His Gln Tyr
 1               5                  10                  15

His Tyr Gln Ala Leu Leu Ala Ala Val Gln Asn Pro Ser Gln Gly Leu
             20                  25                  30

His Pro Phe Pro Leu Pro Phe His Leu Pro Leu His Ala Gly Ala Gly
         35                  40                  45

Ala Gly Ala Pro Ala Ala Gly Pro Gly Ala Asp Ala Asp Ala Ser Ser
     50                  55                  60

Thr His Asn Val His Ala Ala Pro His Ser Gln Pro Pro Arg Gly Phe
 65                  70                  75                  80

Thr Asp Trp Ser Pro Ser Asn Ser Ala Phe Ala Ala Val Ala Ala Gln
                 85                  90                  95

Pro Ala Pro Ala Thr Thr Asn Thr Pro Leu His Tyr Asn Leu Ser Gln
            100                 105                 110
```

```
Pro Tyr Thr Leu Trp Thr His Tyr Met Leu Asn Lys Asn Val Ser Cys
            115                 120                 125

Ser Thr Tyr Pro Thr Gln His Glu Glu Asn Pro Asn Pro Leu Arg His
        130                 135                 140

Thr His Ile Pro Glu Glu Asn Pro His Pro Leu Arg His Thr His Ile
145                 150                 155                 160

Pro Asp Lys Asp Ser Gly Cys Ala Ser Leu Gly Phe Asp Ser Phe
            165                 170                 175

Thr Thr Met Ser Leu Gly Pro Asn Ile Cys Ala His Met Thr Pro Met
                180                 185                 190

Glu Gly Ser Ile Ser Ala Lys Glu Pro Glu Asn Ser Glu Asp Leu Pro
            195                 200                 205

Ala Val Val Arg Ser Ser Asp Glu Met Asp Thr Arg Asn Ser Gly Glu
        210                 215                 220

Ile His Arg Asp Thr Val Gly Pro Leu Pro Glu Ser Lys Gln Ser His
225                 230                 235                 240

Glu Ser Cys Ala Ser Lys Phe Asn Ser Gly Glu Tyr Gln Val Ile Leu
            245                 250                 255

Arg Lys Glu Leu Thr Lys Ser Asp Val Ala Asn Ser Gly Arg Ile Val
        260                 265                 270

Leu Pro Lys Lys Asp Ala Glu Ala Gly Leu Pro Pro Leu Val Gln Gly
    275                 280                 285

Asp Pro Leu Ile Leu Gln Met Asp Asp Met Val Leu Pro Ile Ile Trp
        290                 295                 300

Lys Phe Lys Tyr Arg Phe Trp Pro Asn Asn Lys Ser Arg Met Tyr Ile
305                 310                 315                 320

Leu Glu Ala Ala Gly Glu Phe Val Lys Thr His Gly Leu Gln Ala Gly
            325                 330                 335

Asp Ala Leu Ile Ile Tyr Lys Asn Ser Glu Pro Gly Lys Phe Ile Ile
                340                 345                 350

Arg Gly Glu Lys Ser Ile Gln Gln Thr Asn Pro
            355                 360

<210> SEQ ID NO 31
<211> LENGTH: 349
<212> TYPE: PRT
<213> ORGANISM: Brassica oleracea

<400> SEQUENCE: 31

Met Asp Asn Phe Leu Pro Phe Ser Ser Ser Asn Ala Asn Ser Val Gln
1               5                   10                  15

Glu Leu Ser Met Asp Leu Asn Lys Asn Arg Ser His Phe Ser Met Ala
            20                  25                  30

Gln Pro Gln His Leu Leu Pro Pro Tyr Ser Tyr Val Ala Cys Pro Val
        35                  40                  45

Leu Asp Gln Thr Gly Ala Met Asn His Gln Pro Leu His Ser Ser Asp
    50                  55                  60

Ala Phe Pro Gln Ile Pro Val Val Gln Thr Gly Gly Glu Phe Gly Tyr
65                  70                  75                  80

Leu Val Cys Lys Pro Gly Val Arg Gln Glu Arg Gly Gly Phe Leu Asp
            85                  90                  95

Pro His Ser Thr Lys Met Ala Arg Ile Asn Arg Lys Lys Ala Met Ile
        100                 105                 110

Arg Ser Arg Asn Asn Ser Tyr Leu Asn Ser Ser Ser Asn Glu Leu Val
```

```
            115                 120                 125
Asp Ser Arg Arg Gln Val Ala Leu Thr Met Lys Asn Asn Ala Glu Ile
    130                 135                 140

Ala Ala Arg Lys Asp Phe Tyr Arg Phe Ser Ser Phe Asp Asn Lys Lys
145                 150                 155                 160

Leu Arg Val Leu Leu Val Lys His Leu Lys Asn Ser Asp Val Gly Ser
                165                 170                 175

Leu Gly Arg Ile Val Leu Pro Lys Arg Glu Ala Glu Gly Asn Leu Pro
            180                 185                 190

Glu Leu Ser Asp Lys Glu Gly Met Val Leu Gln Met Arg Asp Val Asp
        195                 200                 205

Ser Val Gln Ser Trp Ser Phe Lys Tyr Lys Tyr Trp Ser Asn Asn Lys
    210                 215                 220

Ser Arg Met Tyr Val Leu Glu Asn Thr Gly Glu Phe Val Lys Lys Asn
225                 230                 235                 240

Gly Val Leu Met Gly Asp Tyr Leu Thr Ile Tyr Glu Asp Glu Ser Lys
                245                 250                 255

Asn Leu Tyr Phe Ser Ile Arg Lys His Pro His Lys Gln Asn Asp Gly
            260                 265                 270

Arg Glu Asp Glu Ser Met Glu Val Ile Glu Met Asn Phe Tyr Glu Asp
        275                 280                 285

Ile Met Phe Asp Tyr Ile Pro Asn Gly Glu Asp Asp Ser Ile Ala Met
    290                 295                 300

Leu Leu Gly Asn Leu Asn Glu His Tyr Pro Tyr Pro Asn Asp Ile Met
305                 310                 315                 320

Asp Leu Thr Val Asp Leu Asp Gln His Gln Ala Thr Ser Ser Ser
                325                 330                 335

Pro Pro Ala Asp His Met Ser Ser Asn Asp Phe Leu Trp
            340                 345

<210> SEQ ID NO 32
<211> LENGTH: 491
<212> TYPE: PRT
<213> ORGANISM: Brachypodium distachyon

<400> SEQUENCE: 32

Met Asp Met Asp Ala Ala Gln Gln Gln His His His Tyr Pro Trp Leu
1               5                   10                  15

Asn Phe Ser Leu Ala His His Cys Gly Met Glu Glu Glu Glu Arg Gly
                20                  25                  30

Ala Ala Ala Glu Leu Ala Ala Ile Ala Gly Ala Ala Pro Pro Pro Lys
            35                  40                  45

Leu Glu Asp Phe Leu Gly Gly Gly Gly Asn Gly Asn Gly Gly Gly
        50                  55                  60

Gly Gly Pro Val Val Pro Ala Gly Ala Ala Glu Met Tyr Glu Ser
65                  70                  75                  80

Glu Leu Lys Phe Leu Ala Ala Gly Phe Leu Gly Ser Gly Gly Thr
                85                  90                  95

Gly Thr Ser Pro Ala Ala Pro Pro Val Val Ala Leu Glu Glu Gln
            100                 105                 110

Ala Ala Glu Ala Lys Leu Ala Leu Pro Leu Val Ala Ala Pro Ala Pro
        115                 120                 125

Glu Thr Lys Lys Ala Val Asp Ser Phe Gly Gln Arg Thr Ser Ile Tyr
    130                 135                 140
```

```
Arg Gly Val Thr Arg His Arg Trp Thr Gly Arg Tyr Glu Ala His Leu
145                 150                 155                 160

Trp Asp Asn Ser Cys Arg Arg Glu Gly Gln Ser Arg Lys Gly Arg Gln
            165                 170                 175

Val Tyr Leu Gly Gly Tyr Asp Lys Glu Glu Lys Ala Ala Arg Ala Tyr
        180                 185                 190

Asp Leu Ala Ala Leu Lys Tyr Trp Gly Ala Ser Thr Thr Thr Asn Phe
    195                 200                 205

Pro Val Ala Asp Tyr Glu Asn Glu Leu Glu Glu Met Lys His Met Thr
210                 215                 220

Arg Gln Glu Phe Val Ala Ser Leu Arg Arg Lys Ser Ser Gly Phe Ser
225                 230                 235                 240

Arg Gly Ala Ser Ile Tyr Arg Gly Val Thr Arg His His Gln His Gly
            245                 250                 255

Arg Trp Gln Ala Arg Ile Gly Arg Val Ala Gly Asn Lys Asp Leu Tyr
        260                 265                 270

Leu Gly Thr Phe Ser Thr Glu Glu Ala Ala Glu Ala Tyr Asp Ile
    275                 280                 285

Ala Ala Ile Lys Phe Arg Gly Leu Asn Ala Val Thr Asn Phe Glu Ile
290                 295                 300

Gly Arg Tyr Asn Val Glu Ser Ile Ser Ser Asn Leu Pro Ile Gly
305                 310                 315                 320

Thr Ala Ser Gly Ala Asn Arg Gly Ser Lys Cys Ala Leu Glu Pro Thr
            325                 330                 335

Pro Val Ile Ser Asp Val Asp Ala Pro Ser Ile Ala Pro His Ser Leu
        340                 345                 350

Ala Phe Thr Ala Leu Pro Met Lys Tyr Asn Gln His Glu Asn Asp Tyr
    355                 360                 365

Leu Ser Phe Leu Ala Met Gln His Gln Gln Gly Asn Leu Gln Gly
370                 375                 380

Leu Gly Tyr Gly Leu Tyr Ser Ser Gly Val Asn Leu Asp Phe Ala Asn
385                 390                 395                 400

Ala His Asn Ala Ala Thr Met Thr Ala Ala Gln Cys Tyr Gly Asn Gly
            405                 410                 415

Gly Gly Ser Leu His His Gln Gln Gln Glu Gln Asp His His Gln
        420                 425                 430

Gln Gln Gln Gln Gln Asp Gln Glu Gln Asn Ser Asn Gly Cys Pro
    435                 440                 445

Ser Ser Val Pro Phe Ala Thr Pro Met Ala Phe Ser Gly Gly Thr Tyr
450                 455                 460

Glu Ser Ser Val Thr Pro Ser Pro Phe Gly Tyr Tyr Ser Pro Asn Met
465                 470                 475                 480

Ala Ala Phe Gln Thr Pro Ile Phe Gly Met Glu
            485                 490

<210> SEQ ID NO 33
<211> LENGTH: 464
<212> TYPE: PRT
<213> ORGANISM: Leersia perrieri

<400> SEQUENCE: 33

Met Asp Met Asp Met Ser Ser Ala Tyr Pro His His Trp Leu Ser Phe
1               5                   10                  15

Ser Leu Ser Asn Asn Asn Tyr His His Gly Leu Leu Glu Ala Leu Ser
            20                  25                  30
```

```
Thr Ser Ser Ala Pro Pro Leu Asp Gly Ala Glu Glu Ala Pro Lys
        35                  40                  45

Met Glu Asp Phe Leu Gly Gly Val Gly Gly Gly Ser Ala Ala Pro Ala
 50                  55                  60

Ala Ala Pro Glu Asp Gln Leu Gly Cys Gly Gly Glu Leu Gly Ser Ile
 65              70                  75                      80

Ala Ala Gly Phe Met Arg Arg Tyr Pro Thr Pro Asp Glu Asn Pro Gly
                     85                  90                  95

Gly Val Thr Ile Ala Met Ala Thr Asp Ala Val Glu Ala Asp Pro Ala
                100                 105                 110

Arg Arg Thr Ala Glu Thr Phe Gly Gln Arg Thr Ser Ile Tyr Arg Gly
             115                 120                 125

Val Thr Arg His Arg Trp Thr Gly Arg Tyr Glu Ala His Leu Trp Asp
         130                 135                 140

Asn Ser Cys Arg Arg Glu Gly Gln Ser Arg Lys Gly Arg Gln Gly Gly
145                 150                 155                 160

Tyr Asp Lys Glu Glu Lys Ala Ala Arg Ala Tyr Asp Leu Ala Ala Leu
                165                 170                 175

Lys Tyr Trp Gly Pro Thr Thr Thr Thr Asn Phe Pro Val Ala Asn Tyr
                180                 185                 190

Glu Lys Glu Leu Glu Glu Met Lys Ser Met Thr Arg Gln Glu Phe Ile
            195                 200                 205

Ala Ser Leu Arg Arg Lys Ser Ser Gly Phe Ser Arg Gly Ala Ser Ile
        210                 215                 220

Tyr Arg Gly Val Thr Arg His His Gln His Gly Arg Trp Gln Ala Arg
225                 230                 235                 240

Ile Gly Arg Val Ala Gly Asn Lys Asp Leu Tyr Leu Gly Thr Phe Ser
                245                 250                 255

Thr Gln Glu Glu Ala Ala Glu Ala Tyr Asp Ile Ala Ala Ile Lys Phe
            260                 265                 270

Arg Gly Leu Asn Ala Val Thr Asn Phe Asp Met Ser Arg Tyr Asp Val
        275                 280                 285

Asp Ser Ile Leu Asn Ser Asp Leu Pro Val Gly Gly Gly Ala Ala Ser
        290                 295                 300

Ala Ala Thr Arg Ala Ala Lys Phe Pro Ser Asp Pro Ser Leu Pro Pro
305                 310                 315                 320

Pro His Gly Ala Gly Ala Ser Ala Ala Met Thr Pro Ser Glu Lys Asp
                325                 330                 335

Tyr Trp Ser Leu Leu Ala Leu His Tyr Gln Gln Gln Gln Gln Gln Gln
            340                 345                 350

Gln Gln Phe Pro Ala Ser Ala Phe Asp Thr Tyr Gly Cys Ser Ser Gly
        355                 360                 365

Val Asn Val Asp Phe Thr Met Gly Thr Ser Ser His Ser Gly Ser Asn
    370                 375                 380

Ser Ser Ser Ser Ser Ala Met Trp Gly Thr Ala Ala Met Gly Gln
385                 390                 395                 400

Gln Asp Ser Ser Asn Arg Gln Ser Asn Ser Tyr Ser Ser His His Asn
                405                 410                 415

Ile Pro Tyr Ala Ser Ala Ala Ala Ala Ala Met Ala Ser Gly Ser
                420                 425                 430

Ala Gly Tyr Glu Gly Ser Thr Gly Asn Asn Gly Thr Trp Val Ala Ser
            435                 440                 445
```

```
Asn Thr Ser Thr Ala Pro His Phe Tyr Asn Tyr Leu Phe Gly Met Glu
    450                 455                 460

<210> SEQ ID NO 34
<211> LENGTH: 321
<212> TYPE: PRT
<213> ORGANISM: Panicum hallii

<400> SEQUENCE: 34

Met Ala Pro Cys Gly Asp Gly Arg Asp Asp Asp Trp Tyr Gln Tyr Gly
1               5                   10                  15

Leu Asp Asp Phe Pro Pro Leu Cys Ser Ala Pro Pro Leu Ala Leu
            20                  25                  30

Leu Arg Ser Pro Tyr Phe Ser Asn Gln Leu Pro Arg Val Pro Val Asp
        35                  40                  45

Gly Ala Thr Val Gly Leu Asp Asp Ala Leu Leu Pro Leu Gly Asp
    50                  55                  60

Ile Asp Leu Glu Ala Phe Asp Ser Ala Asp Glu His Lys Met Ile Pro
65                  70                  75                  80

Pro Ala Gly Gln His Thr Val Gly Gln Asp Tyr Ala Gly Val Asp Val
                85                  90                  95

Val His Glu Asp Gln Lys Pro Met Ala Ile Ala Asp Ser Phe Arg Pro
            100                 105                 110

Arg Ala Asn Ala Leu Glu Leu Thr Met Ser Arg His Gly Glu His Gln
        115                 120                 125

Lys Ser Ser Ser Val Ala Ala Ala Leu Val Pro Pro Pro Pro Pro
    130                 135                 140

Leu Pro Arg Pro Arg Gly Arg Arg Ser Val Asp His Arg Ser Ala Pro
145                 150                 155                 160

Ala His Gly Lys Thr Arg Leu Asp His Ile Gly Phe Asp Glu Leu Arg
                165                 170                 175

Lys Tyr Phe Tyr Met Pro Ile Thr Arg Ala Ala Arg Glu Leu Asn Val
            180                 185                 190

Gly Leu Thr Val Leu Lys Lys Arg Cys Arg Glu Leu Gly Ile Ala Arg
        195                 200                 205

Trp Pro His Arg Lys Met Lys Ser Leu Lys Ser Leu Ile Leu Asn Val
    210                 215                 220

Gln Glu Met Gly Thr Gly Met Asn Pro Ala Ala Val Gln His Glu Leu
225                 230                 235                 240

Ala Ala Leu Glu Thr Tyr Cys Ala Leu Met Glu Glu Asn Pro Ala Ile
                245                 250                 255

Glu Leu Thr Glu Arg Thr Lys Lys Leu Arg Gln Ala Cys Phe Lys Glu
            260                 265                 270

Ser Tyr Lys Arg Arg Ala Ala Ala Val Asn Val Met Asp Arg Ile
        275                 280                 285

Phe Ser Phe Asp Asp His Lys Tyr Arg His Pro Leu Arg Pro Pro Pro
    290                 295                 300

Pro Pro Ser Ser Ala Glu Arg His Gly His Gly Ser Ser Phe Leu Gly
305                 310                 315                 320

Tyr

<210> SEQ ID NO 35
<211> LENGTH: 624
<212> TYPE: PRT
<213> ORGANISM: Saccharum spontaneum
```

```
<400> SEQUENCE: 35

Met Ala Ala Ala Ala Gly Arg Trp Trp Ala Val Val Leu Ala Val Ala
1               5                   10                  15

Val Leu Leu Gly Pro Gly Arg Val Val Ala Asn Thr Glu Gly Asp Ala
            20                  25                  30

Leu Tyr Ser Leu Arg Gln Ser Leu Lys Asp Thr Asn Asn Val Leu Gln
        35                  40                  45

Ser Trp Asp Pro Thr Leu Val Asn Pro Cys Thr Trp Phe His Val Thr
    50                  55                  60

Cys Asn Asn Asp Asn Ser Val Ile Arg Val Asp Leu Gly Asn Ala Gln
65                  70                  75                  80

Leu Ser Gly Val Leu Val Pro Gln Leu Gly Gln Leu Lys Asn Leu Gln
                85                  90                  95

Tyr Leu Glu Leu Tyr Ser Asn Asn Ile Ser Gly Thr Ile Pro Pro Glu
            100                 105                 110

Leu Gly Asn Leu Thr Asn Leu Val Ser Leu Asp Leu Tyr Met Asn Asn
        115                 120                 125

Phe Ser Gly Ile Ile Pro Asp Ser Leu Gly Asn Leu Leu Lys Leu Arg
    130                 135                 140

Phe Leu Arg Leu Asn Asn Asn Ser Leu Val Gly Gln Ile Pro Val Ser
145                 150                 155                 160

Leu Thr Asn Ile Ser Thr Leu Gln Val Leu Asp Leu Ser Asn Asn Asn
                165                 170                 175

Leu Ser Gly Gln Val Pro Ser Thr Gly Ser Phe Ser Leu Phe Thr Pro
            180                 185                 190

Ile Ser Phe Ala Asn Asn Pro Phe Leu Cys Gly Pro Gly Thr Thr Lys
        195                 200                 205

Pro Cys Pro Gly Ala Pro Pro Phe Ser Pro Pro Pro Phe Asn Pro
    210                 215                 220

Pro Ser Pro Pro Thr Gln Ser Thr Gly Ala Ser Ser Thr Gly Ala Ile
225                 230                 235                 240

Ala Gly Gly Val Ala Ala Gly Ala Ala Leu Val Phe Ala Val Pro Ala
                245                 250                 255

Ile Ala Phe Ala Met Trp Arg Arg Arg Lys Pro Glu Glu His Phe Phe
            260                 265                 270

Asp Val Pro Ala Glu Asp Pro Glu Val His Leu Gly Gln Leu Lys
        275                 280                 285

Lys Phe Ser Leu Arg Glu Leu Gln Val Ala Thr Asp Asn Phe Ser Asn
    290                 295                 300

Lys Asn Ile Leu Gly Arg Gly Gly Phe Gly Lys Val Tyr Lys Gly Arg
305                 310                 315                 320

Leu Ala Asp Gly Ser Leu Val Ala Val Lys Arg Leu Lys Glu Glu Arg
                325                 330                 335

Thr Pro Gly Gly Glu Leu Gln Phe Gln Thr Glu Val Glu Met Ile Ser
            340                 345                 350

Met Ala Val His Arg Asn Leu Leu Arg Leu Arg Gly Phe Cys Met Thr
        355                 360                 365

Pro Thr Glu Arg Leu Leu Val Tyr Pro Tyr Met Ala Asn Gly Ser Val
    370                 375                 380

Ala Ser Arg Leu Arg Glu Arg Gln Pro Ser Glu Pro Pro Leu Gln Trp
385                 390                 395                 400

Glu Thr Arg Arg Arg Ile Ala Leu Gly Ser Ala Arg Gly Leu Ser Tyr
                405                 410                 415
```

-continued

Leu His Asp His Cys Asp Pro Lys Ile Ile His Arg Asp Val Lys Ala
              420                 425                 430

Ala Asn Ile Leu Leu Asp Glu Asp Phe Glu Ala Val Val Gly Asp Phe
          435                 440                 445

Gly Leu Ala Lys Leu Met Asp Tyr Lys Asp Thr His Val Thr Thr Ala
      450                 455                 460

Val Arg Gly Thr Ile Gly His Ile Ala Pro Glu Tyr Leu Ser Thr Gly
465                 470                 475                 480

Lys Ser Ser Glu Lys Thr Asp Val Phe Gly Tyr Gly Ile Met Leu Leu
                485                 490                 495

Glu Leu Ile Thr Gly Gln Arg Ala Phe Asp Leu Ala Arg Leu Ala Asn
            500                 505                 510

Asp Asp Asp Val Met Leu Leu Asp Trp Val Lys Gly Leu Leu Lys Glu
        515                 520                 525

Lys Lys Val Glu Met Leu Val Asp Pro Asp Leu Gln Asn Ala Tyr Glu
    530                 535                 540

Glu Ile Glu Val Glu Asn Leu Ile Gln Val Ala Leu Leu Cys Thr Gln
545                 550                 555                 560

Gly Ser Pro Leu Asp Arg Pro Lys Met Ser Glu Val Val Arg Met Leu
                565                 570                 575

Glu Gly Asp Gly Leu Ala Glu Arg Trp Asp Glu Trp Gln Lys Val Glu
            580                 585                 590

Val Val Arg Gln Glu Ala Glu Ser Ala Pro Leu Arg Asn Asp Trp Ile
        595                 600                 605

Val Asp Ser Thr Tyr Asn Leu Arg Ala Val Glu Leu Ser Gly Pro Arg
    610                 615                 620

<210> SEQ ID NO 36
<211> LENGTH: 631
<212> TYPE: PRT
<213> ORGANISM: Setaria italica

<400> SEQUENCE: 36

Met Ala Ala Ala Gly Ala Thr Arg Arg Arg Trp Ala Val Trp Ala
1               5                   10                  15

Leu Leu Leu Leu Arg Leu Leu His Pro Ala Ala Arg Val Leu Ala
            20                  25                  30

Asn Thr Glu Gly Asp Ala Leu His Ser Leu Arg Thr Asn Leu Asn Asp
        35                  40                  45

Pro Asn Asn Val Leu Gln Ser Trp Asp Pro Thr Leu Val Asn Pro Cys
    50                  55                  60

Thr Trp Phe His Val Thr Cys Asn Asn Asp Asn Ser Val Ile Arg Val
65                  70                  75                  80

Asp Leu Gly Asn Ala Ala Leu Ser Gly Thr Leu Val Pro Gln Leu Gly
                85                  90                  95

Gln Leu Lys Asn Leu Gln Tyr Leu Glu Leu Tyr Ser Asn Ser Ile Ser
            100                 105                 110

Gly Thr Ile Pro Ser Glu Leu Gly Asn Leu Thr Asn Leu Val Ser Leu
        115                 120                 125

Asp Leu Tyr Leu Asn Asn Phe Thr Gly Pro Ile Pro Asp Ser Leu Gly
    130                 135                 140

Asn Leu Leu Lys Leu Arg Phe Leu Arg Leu Asn Asn Asn Ser Leu Ser
145                 150                 155                 160

Gly Ser Ile Pro Lys Ser Leu Thr Ala Ile Thr Ala Leu Gln Val Leu

```
                165                 170                 175
Asp Leu Ser Asn Asn Leu Ser Gly Glu Val Pro Ser Thr Gly Ser
            180                 185                 190

Phe Ser Leu Phe Thr Pro Ile Ser Phe Ala Asn Asn Pro Asn Leu Cys
            195                 200                 205

Gly Pro Gly Thr Thr Lys Pro Cys Pro Gly Ala Pro Pro Phe Ser Pro
            210                 215                 220

Pro Pro Pro Tyr Asn Pro Pro Thr Pro Val Gln Ala Gly Ser Ser Ser
225                 230                 235                 240

Ser Ser Thr Gly Ala Ile Ala Gly Gly Val Ala Ala Gly Ala Ala Leu
            245                 250                 255

Leu Phe Ala Val Pro Ala Ile Gly Phe Ala Tyr Trp Arg Arg Arg Lys
            260                 265                 270

Pro Gln Glu His Phe Phe Asp Val Pro Ala Glu Glu Asp Pro Glu Val
            275                 280                 285

His Leu Gly Gln Leu Lys Arg Phe Ser Leu Arg Glu Leu Gln Val Ala
            290                 295                 300

Thr Asp Gly Phe Ser Asn Lys Asn Ile Leu Gly Arg Gly Gly Phe Gly
305                 310                 315                 320

Lys Val Tyr Lys Gly Arg Leu Ala Asp Gly Thr Leu Val Ala Val Lys
            325                 330                 335

Arg Leu Lys Glu Glu Arg Thr Pro Gly Gly Glu Leu Gln Phe Gln Thr
            340                 345                 350

Glu Val Glu Met Ile Ser Met Ala Val His Arg Asn Leu Leu Arg Leu
            355                 360                 365

Arg Gly Phe Cys Met Thr Pro Thr Glu Arg Leu Leu Val Tyr Pro Tyr
            370                 375                 380

Met Ala Asn Gly Ser Val Ala Ser Arg Leu Arg Glu Arg Pro Glu Ser
385                 390                 395                 400

Glu Pro Pro Leu Asp Trp Gln Thr Arg Arg Ile Ala Leu Gly Ser
            405                 410                 415

Ala Arg Gly Leu Ser Tyr Leu His Asp His Cys Asp Pro Lys Ile Ile
            420                 425                 430

His Arg Asp Val Lys Ala Ala Asn Ile Leu Leu Asp Glu Asp Phe Glu
            435                 440                 445

Ala Val Val Gly Asp Phe Gly Leu Ala Lys Leu Met Asp Tyr Lys Asp
            450                 455                 460

Thr His Val Thr Thr Ala Val Arg Gly Thr Ile Gly His Ile Ala Pro
465                 470                 475                 480

Glu Tyr Leu Ser Thr Gly Lys Ser Ser Glu Lys Thr Asp Val Phe Gly
            485                 490                 495

Tyr Gly Ile Met Leu Leu Glu Leu Ile Thr Gly Gln Arg Ala Phe Asp
            500                 505                 510

Leu Ala Arg Leu Ala Asn Asp Asp Val Met Leu Leu Asp Trp Val
            515                 520                 525

Lys Gly Leu Leu Lys Glu Lys Arg Leu Glu Ser Leu Val Asp Glu Asp
            530                 535                 540

Leu Gln His Asn Tyr Ile Asp Val Glu Val Glu Ser Leu Ile Gln Val
545                 550                 555                 560

Ala Leu Leu Cys Thr Gln Ser Ser Pro Met Glu Arg Pro Lys Met Ser
            565                 570                 575

Glu Val Val Arg Met Leu Glu Gly Asp Gly Leu Ala Glu Arg Trp Glu
            580                 585                 590
```

Glu Trp Gln Lys Val Glu Val Arg Gln Glu Val Glu Leu Gly Pro
             595                 600                 605

His Arg Thr Ser Glu Trp Ile Leu Asp Ser Thr Asp Asn Leu His Ala
610                 615                 620

Val Glu Leu Ser Gly Pro Arg
625                 630

<210> SEQ ID NO 37
<211> LENGTH: 356
<212> TYPE: PRT
<213> ORGANISM: Saccharum spontaneum

<400> SEQUENCE: 37

Met Glu Glu Ile Thr His His Phe Gly Val Ala Ala Ser Ser His Ser
1               5                   10                  15

His Gly His Gly Gln His His Pro Trp Ala Ser Ser Leu Ser Ala
            20                  25                  30

Val Val Ala Pro Pro Gln Gln Pro Ser Ala Gly Leu Pro Leu
        35                  40                  45

Thr Leu Asn Thr Val Ala Ala Thr Gly Asn Ser Gly Ala Ser Gly Asn
50                  55                  60

Pro Val Leu Gln Leu Ala Asn Gly Gly Ser Leu Leu Asp Ala Cys Val
65                  70                  75                  80

Asn Val Lys Ala Lys Gly Glu Pro Ser Ser Ser Pro Tyr Ala Gly
                85                  90                  95

Asp Leu Glu Ala Ile Lys Ala Lys Ile Ile Ser His Pro His Tyr Tyr
                100                 105                 110

Ser Leu Leu Ala Ala Tyr Leu Glu Cys Lys Lys Val Gly Ala Pro Pro
            115                 120                 125

Glu Val Ser Ala Arg Leu Thr Ala Met Ala Gln Glu Leu Glu Ala Arg
130                 135                 140

Gln Arg Thr Ala Leu Gly Gly Leu Gly Ala Ala Thr Glu Pro Glu Leu
145                 150                 155                 160

Asp Gln Phe Met Glu Ala Tyr His Glu Met Leu Val Lys Phe Arg Glu
                165                 170                 175

Glu Leu Thr Arg Pro Leu Gln Glu Ala Met Glu Phe Met Arg Arg Val
            180                 185                 190

Glu Ser Gln Leu Asn Ser Leu Ser Ile Ser Gly Arg Ser Leu Arg Asn
            195                 200                 205

Ile Leu Ser Ser Gly Ser Ser Glu Glu Asp Gln Glu Gly Ser Gly Gly
        210                 215                 220

Glu Thr Glu Leu Pro Glu Val Asp Val His Gly Val Asp Gln Glu Leu
225                 230                 235                 240

Lys His His Leu Leu Lys Lys Tyr Ser Gly Tyr Leu Ser Ser Leu Lys
                245                 250                 255

Gln Glu Leu Ser Lys Lys Lys Lys Gly Lys Leu Pro Lys Glu Ala
            260                 265                 270

Arg Gln Gln Leu Leu Ser Trp Trp Asp Leu His Tyr Lys Trp Pro Tyr
            275                 280                 285

Pro Ser Glu Thr Gln Lys Val Ala Leu Ala Glu Ser Thr Gly Leu Asp
            290                 295                 300

Leu Lys Gln Ile Asn Asn Trp Phe Ile Asn Gln Arg Lys Arg His Trp
305                 310                 315                 320

Lys Pro Ser Glu Glu Met His His Leu Met Met Asp Gly Tyr His Thr

```
                    325                 330                 335
Thr Asn Ala Phe Tyr Met Asp Gly His Phe Ile Asn Asp Gly Gly Leu
                340                 345                 350
Tyr Arg Leu Gly
            355

<210> SEQ ID NO 38
<211> LENGTH: 326
<212> TYPE: PRT
<213> ORGANISM: Saccharum spontaneum

<400> SEQUENCE: 38

Met Ala Ala Ala Ile Asp Met Tyr Lys Tyr Phe Asn Ala His Gln Ile
1               5                   10                  15

Ala Ser Ser Pro Ser Asp Gln Glu Leu Ala Lys Ala Leu Glu Pro
                20                  25                  30

Phe Ile Thr Ser Ala Ser Ser Pro Tyr His Arg Tyr Ser Ser Ser
                35                  40                  45

Pro Ser Met Ser Gln Asp Ser Tyr Met Pro Thr Pro Ser Tyr Thr Ser
    50                  55                  60

Phe Ser Thr Ser Pro Leu Pro Thr Pro Ala Ala Ala Thr Ser Ser Ser
65                  70                  75                  80

Ser Pro Phe Ser Gln Leu Pro Pro Leu Tyr Ser Ser Pro Tyr Ala Ala
                85                  90                  95

Pro Gly Met Ala Gly Pro Met Gly Leu Asn Gln Leu Gly Pro Ala Gln
                100                 105                 110

Ile Gln Gln Ile Gln Ala Gln Phe Met Phe Gln Gln Gln Arg Gly
                115                 120                 125

Leu His Ala Ala Phe Leu Gly Pro Arg Ala Gln Pro Met Lys Gln Ser
    130                 135                 140

Gly Ser Pro Pro Leu Ala Pro Ala Gln Ser Lys Leu Tyr Arg Gly Val
145                 150                 155                 160

Arg Gln Arg His Trp Gly Lys Trp Val Ala Glu Ile Arg Leu Pro Lys
                165                 170                 175

Asn Arg Thr Arg Leu Trp Leu Gly Thr Phe Asp Thr Ala Glu Asp Ala
                180                 185                 190

Ala Leu Ala Tyr Asp Lys Ala Ala Phe Arg Leu Arg Gly Asp Met Ala
                195                 200                 205

Arg Leu Asn Phe Pro Ala Leu Arg Arg Asp Gly Ala His Leu Ala Gly
    210                 215                 220

Pro Leu His Ala Ser Val Asp Ala Lys Leu Thr Ala Ile Cys Gln Ser
225                 230                 235                 240

Leu Ala Gly Ser Lys Asn Gly Ser Ser Gly Asp Glu Ser Ala Ala Ser
                245                 250                 255

Pro Pro Asp Ser Pro Lys Cys Ser Ala Ser Thr Glu Gly Glu Gly Glu
                260                 265                 270

Glu Glu Ser Gly Ser Ala Gly Ser Pro Ser Pro Thr Leu Ala Pro
                275                 280                 285

Pro Val Pro Glu Met Ala Lys Leu Asp Phe Thr Glu Ala Pro Trp Asp
                290                 295                 300

Glu Thr Glu Thr Phe His Leu Arg Lys Tyr Pro Ser Trp Glu Ile Asp
305                 310                 315                 320

Trp Asp Ser Ile Leu Ser
                325
```

<210> SEQ ID NO 39
<211> LENGTH: 321
<212> TYPE: PRT
<213> ORGANISM: Brassica napus

<400> SEQUENCE: 39

Met Glu Ala Ala Met Asn Leu Asn Ser Ser Arg Thr Phe Gln Gln Pro
1               5                   10                  15

Asp Ser Phe Gly Gly Gly Glu Leu Met Glu Ala Leu Leu Pro Phe
            20                  25                  30

Ile Lys Ser Val Ser Asp Ser Pro Ser Ala Ser Ala Ser Phe Ile
                35                  40                  45

Asn Pro Ala Ala Ser Ala Phe Pro Leu Pro Thr Phe Arg Asp Tyr Asn
    50                  55                  60

Pro Glu His Tyr Leu Thr Gln Pro Phe Pro Tyr Gly Ser Asp Leu Gln
65                  70                  75                  80

Gln Thr Gly Ser Leu Ile Gly Leu Asn Asn Leu Ser Ser Ser Gln Ile
                85                  90                  95

His Gln Ile Gln Ser Gln Ile His His Asn His Pro Leu Pro Pro Thr
            100                 105                 110

Arg Ser Asn Leu Asn Leu Ser Pro Lys Pro Leu Leu Met Lys Gln Pro
        115                 120                 125

Gly Val Ala Gly Ser Cys Phe Ala Tyr Gly Ala Pro Pro Lys Pro Ala
130                 135                 140

Lys Leu Tyr Arg Gly Val Arg Gln Arg His Trp Gly Lys Trp Val Ala
145                 150                 155                 160

Glu Ile Arg Leu Pro Arg Asn Arg Thr Arg Leu Trp Leu Gly Thr Phe
                165                 170                 175

Asp Thr Ala Glu Glu Ala Ala Leu Ala Tyr Asp Thr Ala Ala Phe Lys
            180                 185                 190

Leu Arg Gly Asp Phe Ala Arg Leu Asn Phe Pro Asn Leu Arg His Asp
        195                 200                 205

Gly Ser Arg Ile Gly Gly Glu Phe Gly Glu Tyr Lys Pro Leu His Ser
210                 215                 220

Thr Val Asp Ala Lys Leu Glu Ala Ile Cys Lys Ser Met Ala Glu Thr
225                 230                 235                 240

Glu Lys Gln Glu Lys Thr Thr Lys Ala Ser Lys Lys Arg Ala Ser Thr
                245                 250                 255

Ala Ala Val Lys Ala Glu Glu Asn Ser Asn Ser Ile Gly Glu Ser Pro
            260                 265                 270

Pro Met Thr Glu Leu Val Glu Ser Ala Gly Ser Ser Pro Leu Ser Glu
        275                 280                 285

Leu Thr Phe Ala Asp Ala Glu Glu Gln Pro Gln Trp Asn Glu Thr Phe
290                 295                 300

Ala Leu Glu Lys Tyr Pro Ser Tyr Glu Ile Asp Trp Asp Ser Ile Leu
305                 310                 315                 320

Pro

<210> SEQ ID NO 40
<211> LENGTH: 317
<212> TYPE: PRT
<213> ORGANISM: Panicum hallii

<400> SEQUENCE: 40

Met Ala Ala Asn Val Gly Gly Lys Ser Val Gly Gly Gly Ala Gly Gly

```
         1               5                  10                 15
Gly Gly Thr Gly Gly Ala Val Thr Ala Cys Arg Ala Ser Gly Ser Arg
                    20                 25                 30

Trp Thr Pro Thr Pro Glu Gln Ile Arg Ile Leu Lys Glu Leu Tyr Tyr
            35                 40                 45

Gly Cys Gly Ile Arg Ser Pro Asn Ser Glu Gln Ile Gln Arg Ile Thr
        50                 55                 60

Ala Met Leu Arg Gln His Gly Lys Ile Glu Gly Lys Asn Val Phe Tyr
65                  70                 75                 80

Trp Phe Gln Asn His Lys Ala Arg Glu Arg Gln Lys Arg Arg Leu Thr
                85                 90                 95

Asn Leu Asp Val Asn Val Pro Ala Ala Val Asp Ala Ser His Leu Gly
                    100                105                110

Ala Leu Ser Leu Ser Ser Pro Ser Gly Ala Ala Pro Pro Ser Ser Pro
                115                120                125

Leu Gly Leu Tyr Pro Ser Asn Gly Gly Ser Thr Leu Gln Leu Asp
            130                135                140

Thr Ser Ser Asp Trp Gly Ser Ala Thr Ala Met Ala Thr Glu Thr Cys
145                 150                155                160

Phe Leu Gln Asp Tyr Met Gly Val Met Arg Ser Thr Gly Gly His His
                    165                170                175

Gly Ser Ser Ala Gly Ala Ala Val Ser Pro Trp Ala Cys Leu Ser Ser
                180                185                190

Ser Asp Ser Trp Ala Ala Val Ala Pro Thr Thr Thr Arg Ala Pro Glu
            195                200                205

Thr Leu Pro Leu Phe Pro Thr Gly Asp Ser Ser His Pro Gln Arg Pro
            210                215                220

Arg His Gly Ala Pro Ala Pro Thr Gly Asp Ala Ile Arg Gly Gly Ser
225                 230                235                240

Ser Ser Gly Tyr Leu Pro Thr Leu Pro Phe Trp Gly Ala Ala Thr
                    245                250                255

Ala Ala Thr Thr Thr Thr Ser Val Thr Ile Gln Gln Gln His His Gln
                    260                265                270

Leu Leu Gln Leu Gln Glu Gln Tyr Ser Phe Asn Thr Thr Thr Ser Gln
                275                280                285

Pro Pro Ser Gln Asp Ala Ser Ala Ala Thr Ala Ser Leu Glu Leu Ser
            290                295                300

Leu Ser Ser Trp Cys Ser Pro Tyr Thr Ala Gly Thr Met
305                 310                315
```